US007811823B2

(12) United States Patent
Ono et al.

(10) Patent No.: US 7,811,823 B2
(45) Date of Patent: Oct. 12, 2010

(54) GENE ENCODING AN ENZYME FOR CATALYZING BIOSYNTHESIS OF LIGNAN, AND USE THEREOF

(75) Inventors: Eiichiro Ono, Nagaokakyo (JP); Yoshikazu Tanaka, Otsu (JP)

(73) Assignee: Suntory Holdings Limited, Osaka (JP)

(*) Notice: Subject to any disclaimer, the term of this patent is extended or adjusted under 35 U.S.C. 154(b) by 835 days.

(21) Appl. No.: 10/573,885

(22) PCT Filed: Sep. 29, 2004

(86) PCT No.: PCT/JP2004/014696

§ 371 (c)(1), (2), (4) Date: Mar. 19, 2007

(87) PCT Pub. No.: WO2005/030944

PCT Pub. Date: Apr. 7, 2005

(65) Prior Publication Data

US 2007/0271624 A1 Nov. 22, 2007

(30) Foreign Application Priority Data

Sep. 30, 2003 (JP) ............................ 2003-341313
Dec. 26, 2003 (JP) ............................ 2003-432383

(51) Int. Cl.
*C12N 15/83* (2006.01)
*C12N 15/11* (2006.01)
*C12N 15/00* (2006.01)
*A01H 5/00* (2006.01)

(52) U.S. Cl. .................... 435/468; 435/320.1; 800/278; 800/295; 536/23.1; 536/23.2; 536/23.6

(58) Field of Classification Search ....................... None
See application file for complete search history.

(56) References Cited

U.S. PATENT DOCUMENTS 5,209,826 A * 5/1993 Ozaki et al. ................... 203/38
5,902,458 A 5/1999 Sugiura et al.
6,376,753 B1 * 4/2002 Batard et al. ................ 800/298

FOREIGN PATENT DOCUMENTS

| | | |
|---|---|---|
| JP | 10-007676 | 1/1998 |
| JP | 2001-139579 | 5/2001 |
| JP | 2001-507931 | 6/2001 |
| WO | WO 98/20113 | 5/1998 |

OTHER PUBLICATIONS

Bevan et al 1999 UniProt TO4730, reference No. Z15382, see SEQ alignment.*

N.G. Lewis et al., "Lignans: Biosynthesis and Function", Comprehensive natural products chemistry vol. 1, 1999, pp. 639-665, and 690-706.

Y. Jiao et al., "Furanofuran Lignan Metabolism As a Function . . . ", Phytochemistry vol. 49, No. 2, 1998, pp. 387-394.

L.B. Davin et al., "Dirigent Proteins and Dirigent Sites Explain . . . ", Plant Physiology vol. 123 pp. 453-461, Jun. 2000.

A.T. Dinkova-Kostova et al., "(+)-Pinoresionl/(+)-Lariciresinol Reductase from Forsythia intermedia", The Journal of Biological Chemistry vol. 271, No. 46, Nov. 15, 1996, pp. 29473-29482.

M. Fujita et al., "Recombinant Pinoresinol-Lariciresinol Reductase form . . . " The Journal of Biological Chemistry vol. 274, No. 2, Jan. 8, 1999, pp. 618-627.

M. Fujita et al., "Recombinant Pinoresinol-Lariciresinol Reductase form . . . " The Journal of Biological Chemistry vol. 274, No. 2, Jan. 8, 1999, pp. 618-627.

Zhi-Qiang Xia et al., "Secoisolariciresinol Dehydrogenase Purification, . . . ", The Journal of Biological Chemistry vol. 276, No. 16, Apr. 20, 2001, pp. 12614-12623.

Xia Z-Q et al. "Dirigent-mediated podophyllotoxin biosynthesis in Llnum flavum and Podophyllum peltatum" Phytochemistry, Pergamon Press, GB, vol. 55, No. 6, Nov. 2000, pp. 537-549, XP004291678.

Gang D R et al. "Regiochemical Control of Monolignol Radical Coupling: A New Paradigm for Lignin and Lignan Biosynthesis" Chemistry and Biology, Current Biology, London , GB, vol. 6, No. 3, Mar. 1999, pp. 143-151, XP000995932 ISSN:1074-5521.

Overkamp Stefan et al. "Cloning and characterization of eight cytochrome p450 cDNAs from chickpea (*Cicer arietinum* L.) cell suspension cultures" Plant Science (Shannon), vol. 155, No. 1, Jun. 2000, pp. 101-108, XP002314013 ISSN:0168-9452.

Dec. 12, 2001, "*Arabidopsis thaliana* cytochrome P450-like protein (F6G17.20) mRNA, complete cds." XP002314014.

Jun. 5, 2002 "*Arabidopsis thaliana* cytochrome P450 protein (At3g28740) mRNA, complete cds." XP002314015.

Aug. 27, 2001, "*Arabidopsis thaliana* cytochrome P450 protein (At3g28740) mRNA, complete cds." XP002314016.

Jun. 14, 2002, "*Arabidopsis thaliana* clone 253698 mRNA, complete cds." XP002314017.

Kato M J et al. "Biosynthesis of antioxidant lignans in *Sesamum indicum* seeds" Phytochemistry, Pergamon Press, GB, vol. 47, No. 4, Feb. 1998 (998-02),, pp. 583-591, XP004293758 ISSN:0031-9422 p. 587, left column.

Ikezawa Nobuhiro et al. "Molecular cloning and characterization of CYP719, a methylenedioxy bridge-forming enzyme that belongs to a novel P450 family, from cultured *Coptis japonica* cells." Journal of Biological Chemistry, vol. 278, No. 40, Oct. 3, 2003, pp. 38557-38565, XP002313984 ISSN:0021-9258.

Suh Mi Chung et al. "Comparative analysis of expressed sequence tags from *Sesamum indicum* and *Arabidopsis thaliana* developing seeds." Plant Molecular Biology, vol. 52, No. 6, Aug. 2003 pp. 1107-1123, XP002313982 ISSN:0167-4412 p. 1115-1119.

International Search Report (PCT/ISA210).

* cited by examiner

*Primary Examiner*—Anne Marie Grunberg
*Assistant Examiner*—Brent Page
(74) *Attorney, Agent, or Firm*—Harness, Dickey & Pierce, P.L.C.

(57) ABSTRACT

The present invention provides an enzyme that catalyzes the reaction producing piperitol from pinoresinol, and a reaction producing sesamin from piperitol. The invention also provides a gene that encodes such enzyme. Further, the invention provides a vector and transformant including a gene encoding the enzyme, and a producing method of the protein using the transformant.

13 Claims, 26 Drawing Sheets

1
CONIPHERYL ALCOHOL
dirigent protein
2
PIPERITOL SYNTHESIZING ENZYME
3
4
SESAMIN SYNTHESIZING ENZYME
5
6
SESAME LIGNAN (FUROFURAN COMPOUNDS)

FIG. 4

> Blastx Search (SST vs PIR)

Reference: Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402.

Query= BXP184.2003.08.12
(1521 letters)

Database: pir1.fst; pir2.fst; pir3.fst; pir4.fst
283,329 sequences; 96,175,589 total letters Searching..................................................done

| Sequences producing significant alignments: | Score (bits) | E Value |
|---|---|---|
| T04730 (PIR) cytochrome P450 homolog F6G17.10 - Arabidopsis thal... | 494 | e-139 |
| C85441 (PIR) cytochrome P450-like protein [imported] - Arabidopsis | 494 | e-139 |
| T52174 (PIR) cytochrome P450 monooxygenase [imported] - Arabidopsis | 487 | e-137 |
| B85441 (PIR) cytochrome P450-like protein [imported] - Arabidopsis | 481 | e-135 |
| T04731 (PIR) cytochrome P450 homolog F6G17.20 - Arabidopsis thal... | 480 | e-135 |
| T10896 (PIR) cytochrome P450 (EC 1.14.-.-) 81B1c - Jerusalem art... | 468 | e-131 |
| A85441 (PIR) cytochrome P450-like protein [imported] - Arabidopsis | 464 | e-130 |
| T00510 (PIR) probable cytochrome P450 At2g23220 [imported] - Ara... | 457 | e-128 |
| T00513 (PIR) cytochrome P450 homolog At2g23190 - Arabidopsis tha... | 453 | e-127 |
| B96691 (PIR) probable cytochrome P450 F28G11.4 [imported] - Arab... | 444 | e-124 |

FIG. 6(a) SrSiP189/ PINORESINOL
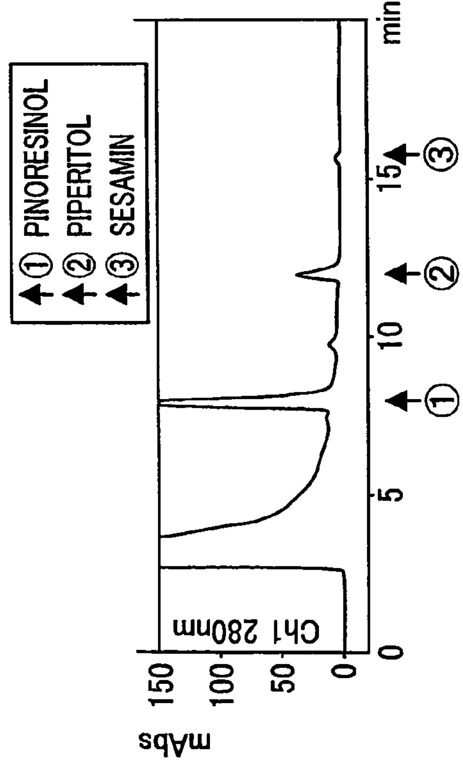
FIG. 6(b) SrSiP189/ PIPERITOL
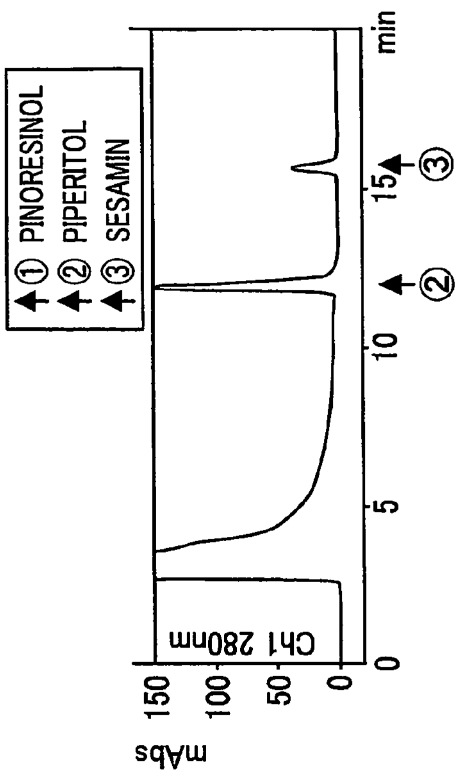
FIG. 6(c) SrSiP189/ PINORESINOL
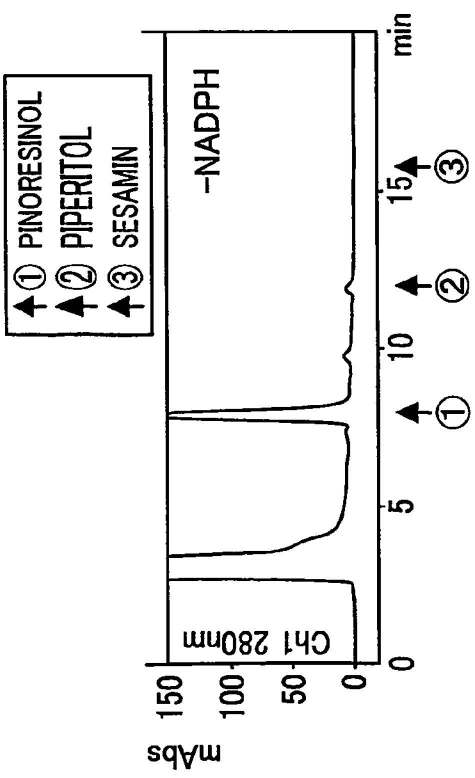
FIG. 6(d) SrSiP189/ PIPERITOL
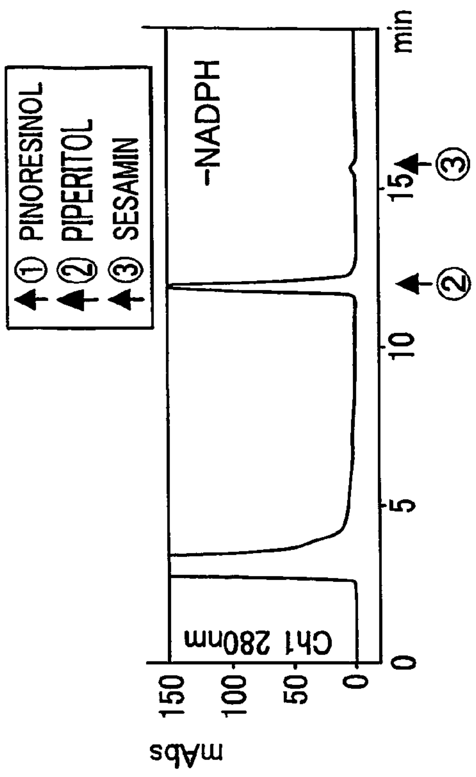

Figure 9A:
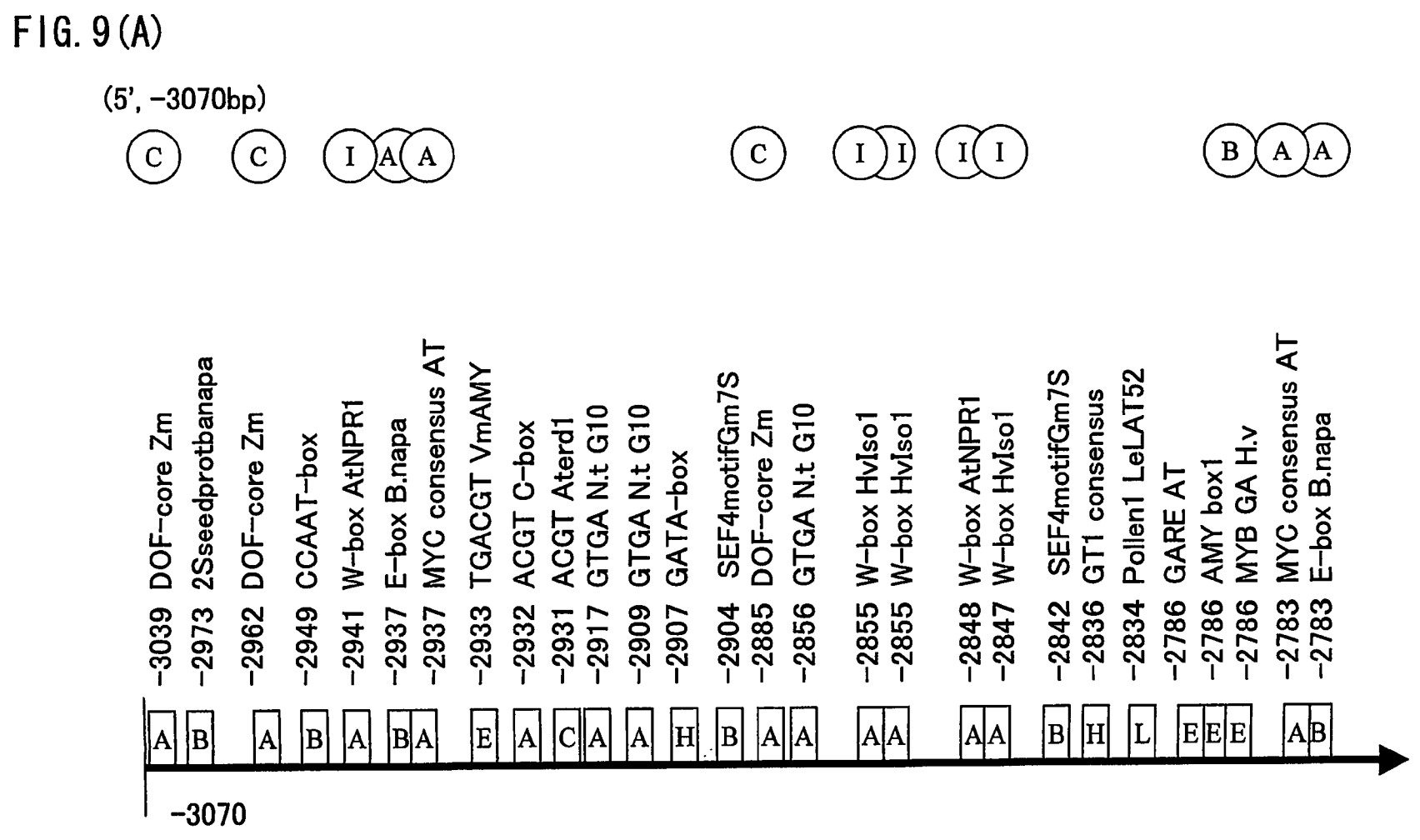

−3039 DOF−core Zm
−2973 2Sseedprotbanapa
−2962 DOF−core Zm
−2949 CCAAT−box
−2941 W−box AtNPR1
−2937 E−box B.napa
−2937 MYC consensus AT
−2933 TGACGT VmAMY
−2932 ACGT C−box
−2931 ACGT Aterd1
−2917 GTGA N.t G10
−2909 GTGA N.t G10
−2907 GATA−box
−2904 SEF4motifGm7S
−2885 DOF−core Zm
−2856 GTGA N.t G10
−2855 W−box HvIso1
−2855 W−box HvIso1
−2848 W−box AtNPR1
−2847 W−box HvIso1
−2842 SEF4motifGm7S
−2836 GT1 consensus
−2834 Pollen1 LeLAT52
−2786 GARE AT
−2786 AMY box1
−2786 MYB GA H.v
−2783 MYC consensus AT
−2783 E−box B.napa

A B A B A B A E A C A A H B A A A A A A B H L E E E A B

−3070

Ex.2
Ex.1
(+1) ATG
-38 CARE OsREP
-49 CAAT-box
-85 TATCCAC OsAMY
-85 TATCCAC HvAL21
-88 CCAAT-box
-93 MYB P Z.m
-95 MYB Plant
-95 REalphaLgLhcb21
-138 SEBFconssPR10A
-168 Pollen1 LeLAT52
-177 CAAT-box
-186 TATCCAC OsAMY
-191 ACGT Aterd1
-215 Pollen1 LeLAT52
-230 NtBBF1-A.r-RolB
-236 SEF4motifGm7S
-279 ACGT Aterd1
-278 CGACG OsAmy3
-316 DOF-core Zm
-322 E-box B.napa
-322 MYC A.t rd22
-322 MYC consensus AT
-327 PAL-box-A P.c

FIG. 10

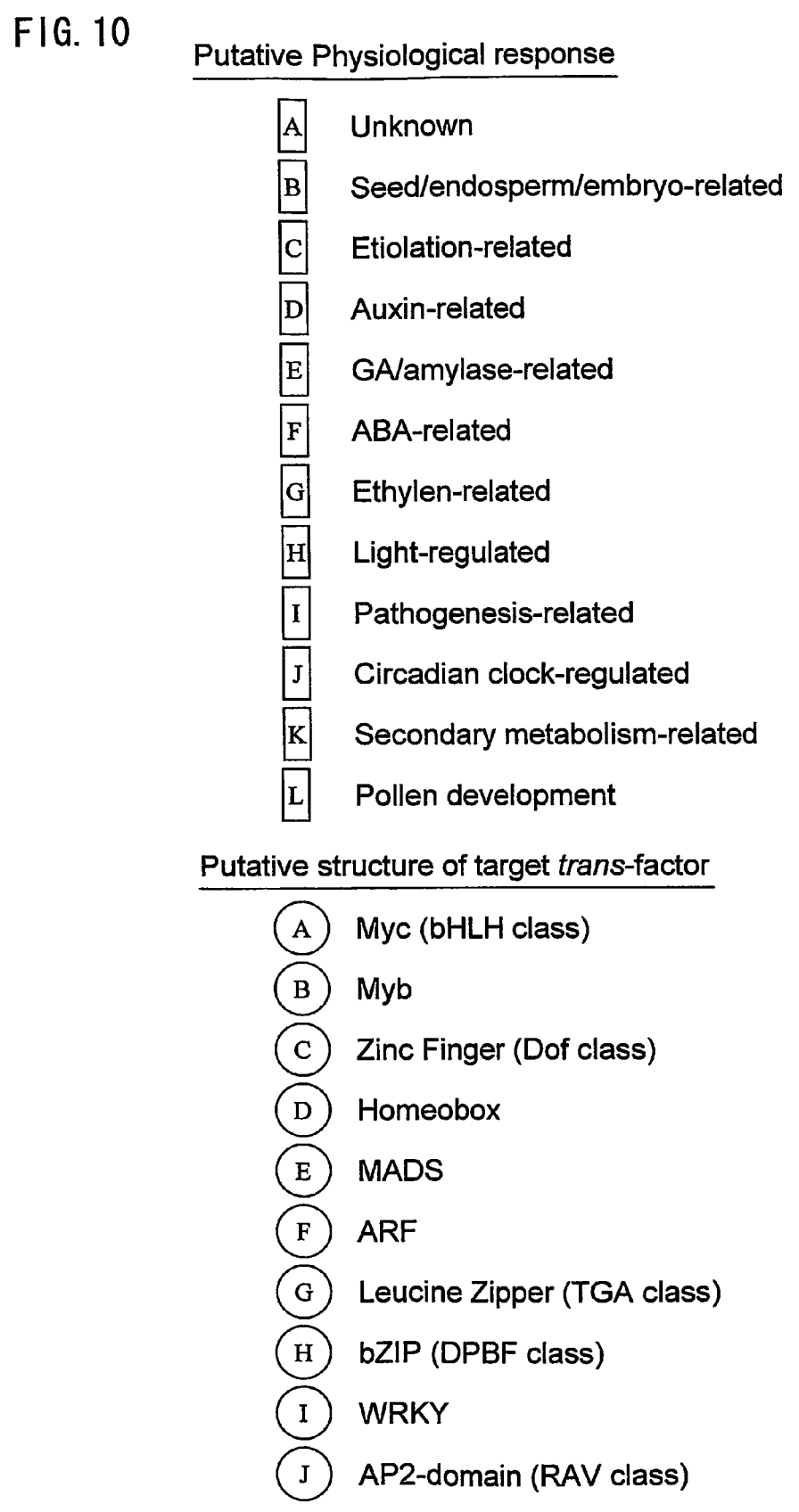

Putative Physiological response

- A Unknown
- B Seed/endosperm/embryo-related
- C Etiolation-related
- D Auxin-related
- E GA/amylase-related
- F ABA-related
- G Ethylen-related
- H Light-regulated
- I Pathogenesis-related
- J Circadian clock-regulated
- K Secondary metabolism-related
- L Pollen development Putative structure of target *trans*-factor

- (A) Myc (bHLH class)
- (B) Myb
- (C) Zinc Finger (Dof class)
- (D) Homeobox
- (E) MADS
- (F) ARF
- (G) Leucine Zipper (TGA class)
- (H) bZIP (DPBF class)
- (I) WRKY
- (J) AP2-domain (RAV class)

FIG. 11 (D)

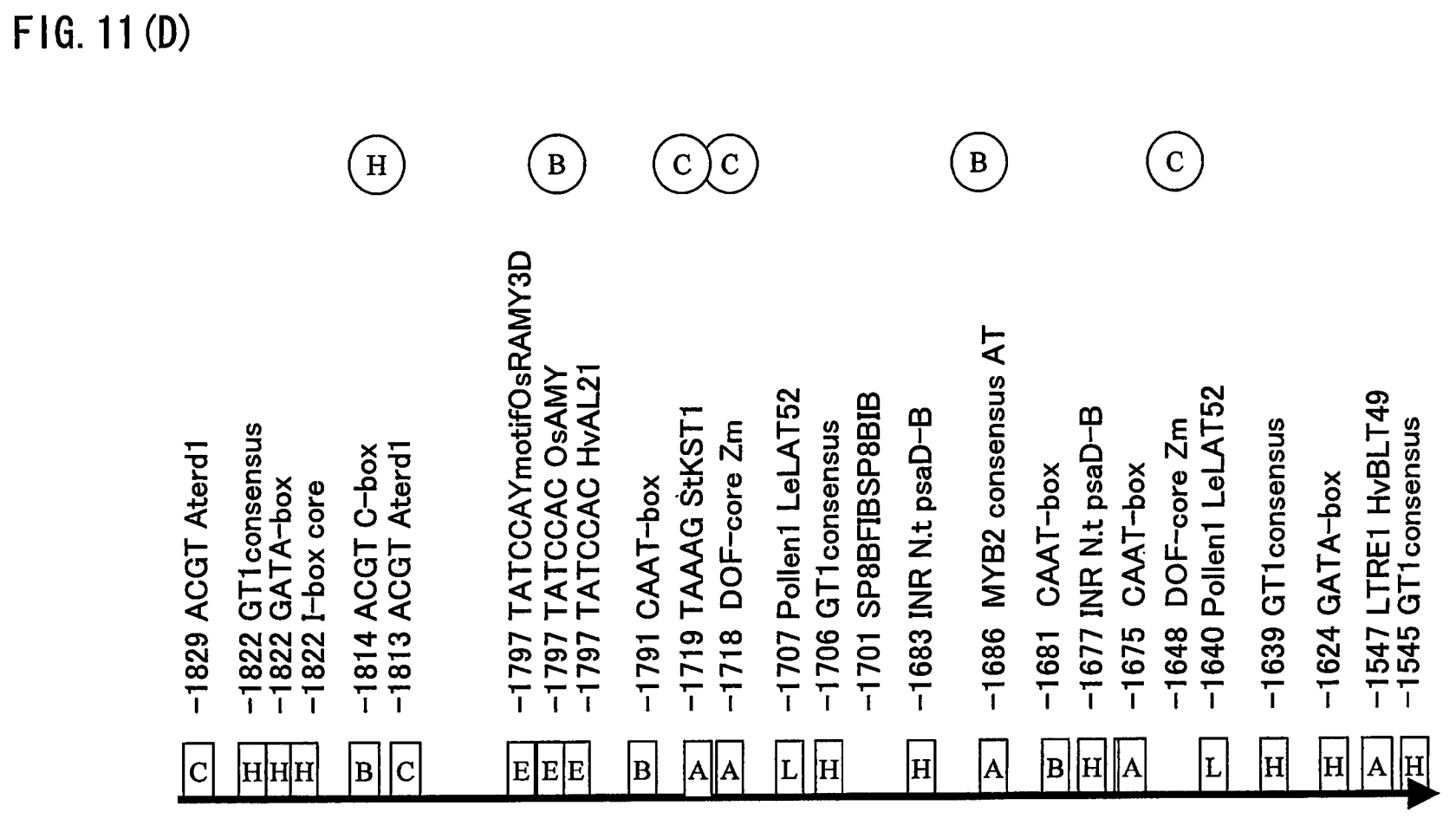

-1829 ACGT Aterd1 C
-1822 GT1 consensus H
-1822 GATA-box H
-1822 I-box core H
-1814 ACGT G-box B
-1813 ACGT Aterd1 C
H
-1797 TATCCAYmotifOsRAMY3D E
-1797 TATCCAC OsAMY E
-1797 TATCCAC HvAL21 E
B
-1791 CAAT-box B
-1719 TAAAG StKST1 A
C
-1718 DOF-core Zm A
C
-1707 Pollen1 LeLAT52 L
-1706 GT1 consensus H
-1701 SP8BFIBSP8BIB
-1683 INR N.t psaD-B H
-1686 MYB2 consensus AT A
B
-1681 CAAT-box B
-1677 INR N.t psaD-B H
-1675 CAAT-box A
-1648 DOF-core Zm
C
-1640 Pollen1 LeLAT52 L
-1639 GT1 consensus H
-1624 GATA-box H
-1547 LTRE1 HvBLT49 A
-1545 GT1 consensus H FIG. 12(a)
1st Intron of SST (S.indicum)
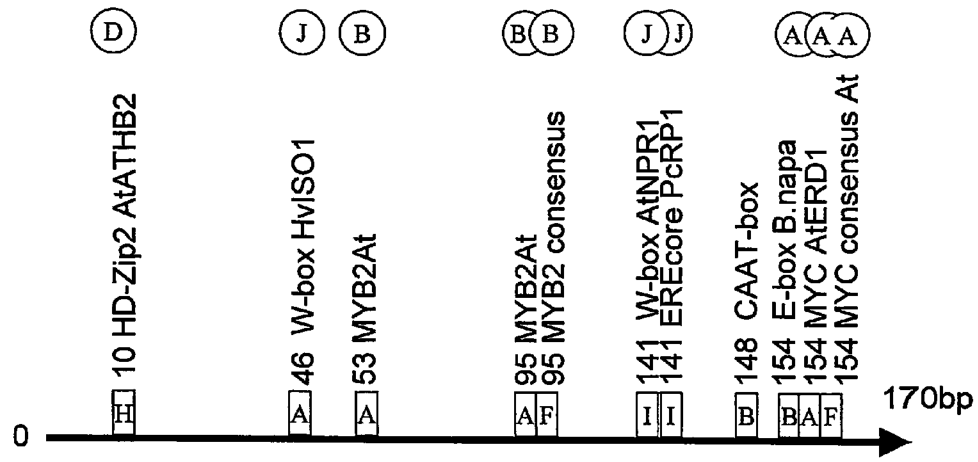
FIG. 12(b)
1st Intron of SrSST (S.radiatum)
FIG. 12(c)
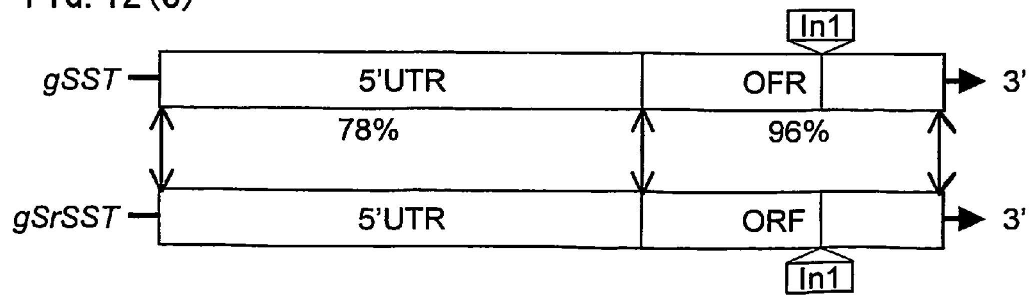

SEQUENCE LISTING

```
<160> NUMBER OF SEQ ID NOS: 79

<210> SEQ ID NO 1
<211> LENGTH: 506
<212> TYPE: PRT
<213> ORGANISM: Sesamum indicum
<220> FEATURE:
<223> OTHER INFORMATION: SiP189

<400> SEQUENCE: 1

Met Glu Ala Glu Met Leu Tyr Ser Ala Leu Ala Leu Thr Phe Ala Ile
  1               5                  10                  15

Phe Met Val Tyr Arg Ile Leu Ser Asn Ser Gln Asp Lys Arg Ser Leu
             20                  25                  30

Thr Lys Leu Pro Pro Ser Pro Pro Gly Trp Leu Pro Val Ile Gly His
         35                  40                  45

Ala His Leu Met Lys Asn Leu Leu His Arg Thr Leu Tyr Asp Phe Ser
     50                  55                  60

Gln Lys Leu Gly Pro Ile Phe Ser Ile Arg Phe Gly Ser Arg Leu Val
 65                  70                  75                  80

Val Val Val Ser Ser Ser Ser Leu Val Glu Glu Cys Phe Thr Lys Tyr
                 85                  90                  95

Asp Ile Val Leu Ala Asn Arg Pro Gln Ala Ser Val Asp Arg Arg Ser
            100                 105                 110

Leu Gly Phe Ser Thr Thr Ser Val Ile Gly Ala Pro Tyr Gly Asp His
        115                 120                 125

Trp Arg Asn Leu Arg Lys Leu Cys Asp Leu Glu Val Phe Ala Pro Thr
    130                 135                 140

Arg Leu Ala Ser Phe Leu Ser Ile Arg Leu Asp Glu Arg Asp Arg Met
145                 150                 155                 160

Ile Ser Ala Leu Tyr Lys Ile Ser Ser Ala Gly Phe Ala Lys Val Asn
                165                 170                 175

Leu Glu Ala Lys Ile Val Glu Leu Thr Phe Asn Asn Ile Met Arg Met
            180                 185                 190

Val Ala Ala Lys Arg Tyr Tyr Gly Glu Glu Ala Glu Asp Asp Glu Glu
        195                 200                 205

Ala Lys Arg Phe Arg Asp Leu Thr Lys Glu Ala Leu Glu Leu Thr Ser
```

-continued

```
    210                 215                 220

Ala Ser Asn Pro Gly Glu Ile Phe Pro Ile Leu Arg Trp Leu Gly Cys
225                 230                 235                 240

Asn Gly Leu Glu Lys Lys Leu Ala Val His Ser Arg Lys Thr Asp Glu
                245                 250                 255

Phe Met Gln Gly Leu Leu Asp Glu His Arg Arg Gly Glu Arg Gln Asn
            260                 265                 270

Thr Met Val Asp His Leu Leu Ser Leu Gln Glu Ser Gln Pro Glu Tyr
        275                 280                 285

Tyr Thr Asp Glu Ile Ile Thr Gly Leu Ile Val Ala Leu Ile Ile Ala
    290                 295                 300

Gly Thr Asp Ala Ser Val Val Thr Thr Glu Trp Ala Met Ser Leu Leu
305                 310                 315                 320

Leu Asn His Pro Lys Val Leu Glu Lys Ala Arg Lys Glu Leu Asp Thr
                325                 330                 335

Leu Val Gly His Glu Arg Met Val Asp Glu His Asp Leu Pro Lys Leu
            340                 345                 350

Arg Tyr Leu His Cys Ile Val Leu Glu Thr Leu Arg Leu Phe Pro Ser
        355                 360                 365

Val Pro Thr Leu Val Pro His Glu Pro Ser Glu Asp Cys Lys Ile Gly
    370                 375                 380

Gly Tyr Asn Val Pro Lys Gly Thr Met Val Leu Val Asn Ala Trp Ala
385                 390                 395                 400

Ile His Arg Asp Pro Lys Val Trp Asp Asp Pro Leu Ser Phe Lys Pro
                405                 410                 415

Asp Arg Phe Glu Ile Met Glu Val Glu Thr His Lys Leu Leu Pro Phe
            420                 425                 430

Gly Met Gly Arg Arg Ala Cys Pro Gly Ala Gly Leu Ala Gln Lys Phe
        435                 440                 445

Val Gly Leu Ala Leu Gly Ser Leu Ile Gln Cys Phe Asp Trp Glu Arg
    450                 455                 460

Thr Ser Pro Glu Lys Ile Asp Leu Asn Glu Gly Ser Gly Ile Thr Leu
465                 470                 475                 480

Pro Lys Ala Lys Thr Leu Glu Ala Met Cys Lys Pro Arg His Val Met
                485                 490                 495

Glu Lys Val Leu Arg Gln Val Ser Asn Val
            500                 505


<210> SEQ ID NO 2
<211> LENGTH: 1518
<212> TYPE: DNA
<213> ORGANISM: Sesamum indicum
<220> FEATURE:
<223> OTHER INFORMATION: SiP189

<400> SEQUENCE: 2

atggaagctg aaatgctata ttcagctctc gctctcacct tcgccatatt catggtttac      60

agaattcttt ctaattcgca ggacaagcgc agcctgacta agctgcctcc gagcccgccc     120

ggttggctgc cggtgatcgg ccacgctcat ctcatgaaaa atctcctcca tagaacacta     180

tacgacttct cccagaaact gggacccata ttttccatcc ggttcgggtc gcgcctcgtg     240

gtggtggtgt cctcctcctc cctggtggag gaatgtttca ccaagtatga cattgtcttg     300

gcaaatcgcc ctcaggcttc tgttgaccgg cgctcacttg ggttcagcac caccagcgta     360

atcggggccc cgtacgggga ccattggcgc aacctgcgaa agttgtgcga tcttgaagta     420
```

-continued

```
ttcgccccga cccgtctcgc ctcgttttta tccatcaggc ttgacgagag ggaccgcatg    480

atttccgcgt tatacaaaat ctcgtccgcc ggtttcgcga aggtgaattt ggaagcgaag    540

attgtggagc tgacgtttaa taacataatg aggatggtgg cggcgaagag atactatggg    600

gaggaggcgg aggacgacga ggaggcgaag aggttcaggg acctgacgaa ggaggctttg    660

gagttgacga gcgcttccaa tcctggtgag atatttccaa tattgcggtg gcttggttgc    720

aatgggctgg agaagaagct ggctgttcac tcgcggaaga cggatgagtt catgcaaggg    780

ctgctggacg aacaccgacg gggcgagcgc cagaacacca tggttgatca tttgctttcg    840

ttgcaggaat ctcaacctga gtactacact gatgaaatca tcactggcct catagttgca    900

ttgataattg cgggaacgga tgcatcggtt gtaactacag aatgggcgat gtccctttta    960

ctaaatcatc ccaaagtact tgaaaaggct agaaaagaac tggacactct agtaggacac   1020

gaacgcatgg ttgatgaaca cgatctcccc aaactacgtt accttcactg catagtcttg   1080

gagaccttaa ggttattccc ttctgttcca actttggtgc cacacgaacc atcagaggat   1140

tgtaaaattg gggatacaa tgtccccaag gggacaatgg tattagtgaa tgcttgggca    1200

atacaccgag accccaaggt gtgggacgac cccttgagct ttaagcccga caggtttgag   1260

ataatggaag tggagacaca caagttgttg ccgttcggaa tgggcaggag agcgtgtcct   1320

ggagctggac tggcgcagaa gtttgtgggg ttggctttgg ggtcgctgat tcagtgtttc   1380

gactgggaga gaacgagtcc cgagaaaatt gacttgaacg aaggttctgg gataaccttg   1440

cctaaagcta agacgttgga agccatgtgc aaacctagac atgtcatgga aaaagttctt   1500

cgtcaggttt ccaacgtt                                                 1518


<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence, Si18SrRNA-FW

<400> SEQUENCE: 3

tatgcttgtc tcaaagatta a                                               21


<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence, Si18SrRNA-RV

<400> SEQUENCE: 4

aacatctaag ggcatcacag a                                               21


<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:
      Artificially Synthesized Primer Sequence, CYP90A-FW

<400> SEQUENCE: 5

ttttccgatg aagagattgt tgac                                            24
```

-continued

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Artificially Synthesized Primer Sequence, CYP90A-RV

<400> SEQUENCE: 6
tgccatctcc aagggttg 18

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Artificially Synthesized Primer Sequence, CYP72B-FW

<400> SEQUENCE: 7
cttaatgttc aaatgataat ggat 24

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Artificially Synthesized Primer Sequence, CYP72B-RV

<400> SEQUENCE: 8
gtaaatcgtt cagggttg 18

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Artificially Synthesized Primer Sequence, CYP71B-FW

<400> SEQUENCE: 9
ttcaccactg atcatctcaa agga 24

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Artificially Synthesized Primer Sequence, CYP71B-RV

<400> SEQUENCE: 10
agaaacctgt cagggtta 18

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Artificially Synthesized Primer Sequence, CYP84A-FW

<400> SEQUENCE: 11
cttacccgtg acaatatcaa agca 24

<210> SEQ ID NO 12

-continued

<211> LENGTH: 18
<212> TYPE: DNA
<213> ORGANISM: Artificial Sequence
<220> FEATURE:
<223> OTHER INFORMATION: Description of Artificial Sequence: Artificially Synthesized Primer Sequence, CYP84A-RV

<400> SEQUENCE: 12
aaaaacctcg atggtcta 18

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Artificially Synthesized Primer Sequence, CYP96A-FW

<400> SEQUENCE: 13
agtcatgata agttcctcag ggac 24

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Artificially Synthesized Primer Sequence, CYP96A-RV

<400> SEQUENCE: 14
atccatctct ctggcttg 18

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Artificially Synthesized Primer Sequence, CYP710A-FW

<400> SEQUENCE: 15
tccgaagacg aagccatcgg cggt 24

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Artificially Synthesized Primer Sequence, CYP710A-RV

<400> SEQUENCE: 16
ctaaaccggt ccggatcg 18

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Artificially Synthesized Primer Sequence, CYP86A-FW

<400> SEQUENCE: 17
cgcgtggcgc tcaacttcat ccta 24

<210> SEQ ID NO 18
<211> LENGTH: 18

-continued

<212> TYPE: DNA
<213> ORGANISM: Artificial Sequence
<220> FEATURE:
<223> OTHER INFORMATION: Description of Artificial Sequence: Artificially Synthesized Primer Sequence, CYP86A-RV

<400> SEQUENCE: 18
atccatctct ctggtttg 18

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Artificially Synthesized Primer Sequence, CYP74-FW

<400> SEQUENCE: 19
cgagaagaag ctactcacaa tctt 24

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Artificially Synthesized Primer Sequence, CYP74-RV

<400> SEQUENCE: 20
acgaatctct ccggcaca 18

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Artificially Synthesized Primer Sequence, CYP75B-FW

<400> SEQUENCE: 21
ttaacggata ctgagattaa agcct 25

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Artificially Synthesized Primer Sequence, CYP75B-RV

<400> SEQUENCE: 22
aagaatctct cgggttta 18

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Artificially Synthesized Primer Sequence, CYP79F-FW

<400> SEQUENCE: 23
gtcacaccag acgaaatcaa agct 24

<210> SEQ ID NO 24
<211> LENGTH: 18
<212> TYPE: DNA

```
<213> ORGANISM: Artificial Sequence
<220> FEATURE:
<223> OTHER INFORMATION: Description of Artificial Sequence:
      Artificially Synthesized Primer Sequence, CYP79F-RV

<400> SEQUENCE: 24

aggtgacgct ccggtttg                                          18


<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:
      Artificially Synthesized Primer Sequence, CYP81D-FW

<400> SEQUENCE: 25

tacatggacc gcatcatcaa agga                                   24


<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence:
      Artificially Synthesized Primer Sequence, CYP81D-RV

<400> SEQUENCE: 26

tcgaacctct ctggcttg                                          18


<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:
      Artificially Synthesized Primer Sequence, CYP705A-FW

<400> SEQUENCE: 27

catatcaagt cgcttctcac ggta                                   24


<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence:
      Artificially Synthesized Primer Sequence, CYP705A-RV

<400> SEQUENCE: 28

agaaacctct ctggttta                                          18


<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence:
      Artificially Synthesized Primer Sequence, CYP83A-FW

<400> SEQUENCE: 29

tttactgatg ataatgtcaa agcc                                   24


<210> SEQ ID NO 30
<211> LENGTH: 18
<212> TYPE: DNA
<213> ORGANISM: Artificial Sequence
```

<220> FEATURE:
<223> OTHER INFORMATION: Description of Artificial Sequence:
      Artificially Synthesized Primer Sequence, CYP83A-RV

<400> SEQUENCE: 30
agaaacctct cgggccta 18

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence, SiP168-FW

<400> SEQUENCE: 31
tttcccttgt tctcctactc t 21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence, SiP168-RV

<400> SEQUENCE: 32
aaataatgat agctaaattt t 21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence, SiP189-FW

<400> SEQUENCE: 33
tcgtttttat ccatcaggct t 21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence, SiP189-RV

<400> SEQUENCE: 34
caaacgttgg aaacctgacg a 21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence, SiP236-FW

<400> SEQUENCE: 35
ggatgttctg tggaagttaa a 21

<210> SEQ ID NO 36
<211> LENGTH: 21
<212> TYPE: DNA
<213> ORGANISM: Artificial Sequence
<220> FEATURE:

-continued

<223> OTHER INFORMATION: Description of Artificial Sequence:
      Artificially Synthesized Primer Sequence, SiP236-RV

<400> SEQUENCE: 36
atctaagttt catgcagttt t 21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence, SiP249-FW

<400> SEQUENCE: 37
ctaagcttca aaatgtcgat a 21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence, SiP249-RV

<400> SEQUENCE: 38
ccaacttact tattacagat a 21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence:
      Artificially Synthesized Primer Sequence, SiP288-FW

<400> SEQUENCE: 39
aaaatggtgg gaattgtgta t 21

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence:
      Artificially Synthesized Primer Sequence, SiP288-RV

<400> SEQUENCE: 40
tacatctcaa tttttctta 19

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence:
      Artificially Synthesized Primer Sequence, GR-SiP168-RV

<400> SEQUENCE: 41
cacgatcctg gagatttccg gggaggatac aa 32

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence:

Artificially Synthesized Primer Sequence, GR-SiP168-Nest-RV

<400> SEQUENCE: 42
gtaggttttg gagagttt 18

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: Artificially Synthesized Primer Sequence, GR-SiP189-RV

<400> SEQUENCE: 43
ctcgtcgtcc tccgcctcct ccccatagta t 31

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Artificially Synthesized Primer Sequence, GR-SiP189-Nest-RV

<400> SEQUENCE: 44
accatcctca ttatgttatt a 21

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Artificially Synthesized Primer Sequence, GR-SiP236-RV

<400> SEQUENCE: 45
ccaggagaga gttgttgctg ttgtgtct 28

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Artificially Synthesized Primer Sequence, GR-SiP236-Nest-RV

<400> SEQUENCE: 46
tataaagctt attgttat 18

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Artificially Synthesized Primer Sequence, SiP168-BamHl-FW

<400> SEQUENCE: 47
ggatccaaaa gagcaaatta tggatctact act 33

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: Artificially Synthesized Primer Sequence, SiP168-Xhol-RV

<400> SEQUENCE: 48
ctcgagaagg gaaaataatg atagctaaat ttt 33

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Artificially Synthesized Primer Sequence, SiP189-BamHl-FW

<400> SEQUENCE: 49
ggatcctttt cagccaacat ggaagctgaa 30

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: Artificially Synthesized Primer Sequence, SiP189-Xhol-RV

<400> SEQUENCE: 50
ctcgagaaaa agagcatcat ttaatcatac act 33

<210> SEQ ID NO 51
<211> LENGTH: 35
<212> TYPE: DNA
<213> ORGANISM: Artificial Sequence
<220> FEATURE:
<223> OTHER INFORMATION: Description of Artificial Sequence: Artificially Synthesized Primer Sequence, SiP236-BamHl-FW

<400> SEQUENCE: 51
ggatccttca cttcacttca ttgctcaatg gcaaa 35

<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence: Artificially Synthesized Primer Sequence, SiP236-Xhol-RV

<400> SEQUENCE: 52
ctcgagaaca gctgagaccc cacagcaatc taa 33

<210> SEQ ID NO 53
<211> LENGTH: 1503
<212> TYPE: DNA
<213> ORGANISM: Sesamum indicum
<220> FEATURE:
<223> OTHER INFORMATION: SiP249

<400> SEQUENCE: 53
atgtcgatac ctctccttat ctctctctca ttaatcatcc ttgttttcct actagtccga 60
cgacgccgca acagcccggc tggtcgaaaa ctccggcgtc ctccggggcc tcctggcctt 120
cccttcctcg ggaacttgct ccaatacaac ccctccgatc tccatctccg cctgacaaaa 180
ctctcagaaa agtacggccc gcttatgtac atgacgttcg tcggaaagcc cgtggttgtg 240
atttcatcgg cccgagtggc caaagaggct ttgaagtaca atgaccttgc attttcgagc 300
aggccttcta ccattgcatc gcgcaaagtg gcttacaaca acagtgacat ctccatgtca 360

-continued

```
ccgtacacag agtactggag agaactgcgg aaaatggtcg ttcttcgcct ctttacggtc    420

aaacaagtga actctttccg ccctgctcga gaagaagaag tggcccgcat ggtgaaagag    480

atttccagac gggccaacgc gcatcagccc gttaacatta atgaaatagc gttgtcgttg    540

tcgagcagga tgatatctag gtttgcactg ggaagaggt acgacgagga gaacgggccg    600

gaaaagagga ggttcgacag gattctgcag ctgcttcagt tggtgtcggt ggaaattttc    660

tttggtgatt attctccatg gctgggctgg attgacagac tgtgtggtaa ggtttctcag    720

cttgagaagg cgttcaagga tttggattca ttgtatgaag agatgatcgc ggagcatctg    780

agcccgaata ggcccgagtc tatgaacgga gacattcttg atatgctaat tcagatgaaa    840

gaagatcggt cgtcgacggt tcaaattgat tgggatcata tcaagggcgt actcatgaac    900

atgttcgtag ccggaacaga cacaactgca gctacaataa catgggcaat gacagctctg    960

atcaagaagc ctcaagtact gaacaaagtg caacaagaaa tcagatctgt ggtcggaaag   1020

aaaggcagcg tagccgaaga tgatatacaa aaacttccct attttaaagc ggtggtgaag   1080

gagactctga gactgtacgc accagctcca ctctcactgc ccagactgac aatcaaaagc   1140

agcgtcatag atggatacga cattgaaccc aacaccatag tttacgtgaa cgtttgggcg   1200

attagccgag acaaggattt ttgggagaac ccggatgagt tcttgcccga aagattcttg   1260

aacagtagcg tggactttaa aggccaagat ttcgggtttc ttccattcgg gtcggggcga   1320

agagtgtgcc ctggaatggc cttggggact gcagaagtgg aggtgtcgct tgctaatatt   1380

ctgtattgct tccactggga attgccgcct ggaatggtag aagatgacgt tgatatggac   1440

tttttgcctg gaattactac tcataagaaa aatgcactct atttgatggc caaaagctat   1500

ctg                                                                 1503
```

```
<210> SEQ ID NO 54
<211> LENGTH: 501
<212> TYPE: PRT
<213> ORGANISM: Sesamum indicum
<220> FEATURE:
<223> OTHER INFORMATION: SiP249

<400> SEQUENCE: 54

Met Ser Ile Pro Leu Leu Ile Ser Leu Ser Leu Ile Ile Leu Val Phe
  1               5                  10                  15

Leu Leu Val Arg Arg Arg Arg Asn Ser Pro Ala Gly Arg Lys Leu Arg
             20                  25                  30

Arg Pro Pro Gly Pro Pro Gly Leu Pro Phe Leu Gly Asn Leu Leu Gln
         35                  40                  45

Tyr Asn Pro Ser Asp Leu His Leu Arg Leu Thr Lys Leu Ser Glu Lys
     50                  55                  60

Tyr Gly Pro Leu Met Tyr Met Thr Phe Val Gly Lys Pro Val Val Val
 65                  70                  75                  80

Ile Ser Ser Ala Arg Val Ala Lys Glu Ala Leu Lys Tyr Asn Asp Leu
                 85                  90                  95

Ala Phe Ser Ser Arg Pro Ser Thr Ile Ala Ser Arg Lys Val Ala Tyr
            100                 105                 110

Asn Asn Ser Asp Ile Ser Met Ser Pro Tyr Thr Glu Tyr Trp Arg Glu
        115                 120                 125

Leu Arg Lys Met Val Val Leu Arg Leu Phe Thr Val Lys Gln Val Asn
    130                 135                 140

Ser Phe Arg Pro Ala Arg Glu Glu Glu Val Ala Arg Met Val Lys Glu
145                 150                 155                 160
```

-continued

```
Ile Ser Arg Arg Ala Asn Ala His Gln Pro Val Asn Ile Asn Glu Ile
                165                 170                 175

Ala Leu Ser Leu Ser Ser Arg Met Ile Ser Arg Phe Ala Leu Gly Lys
            180                 185                 190

Arg Tyr Asp Glu Glu Asn Gly Pro Glu Lys Arg Arg Phe Asp Arg Ile
        195                 200                 205

Leu Gln Leu Leu Gln Leu Val Ser Val Glu Ile Phe Phe Gly Asp Tyr
    210                 215                 220

Ser Pro Trp Leu Gly Trp Ile Asp Arg Leu Cys Gly Lys Val Ser Gln
225                 230                 235                 240

Leu Glu Lys Ala Phe Lys Asp Leu Asp Ser Leu Tyr Glu Glu Met Ile
                245                 250                 255

Ala Glu His Leu Ser Pro Asn Arg Pro Glu Ser Met Asn Gly Asp Ile
            260                 265                 270

Leu Asp Met Leu Ile Gln Met Lys Glu Asp Arg Ser Ser Thr Val Gln
        275                 280                 285

Ile Asp Trp Asp His Ile Lys Gly Val Leu Met Asn Met Phe Val Ala
    290                 295                 300

Gly Thr Asp Thr Thr Ala Ala Thr Ile Thr Trp Ala Met Thr Ala Leu
305                 310                 315                 320

Ile Lys Lys Pro Gln Val Leu Asn Lys Val Gln Gln Glu Ile Arg Ser
                325                 330                 335

Val Val Gly Lys Lys Gly Ser Val Ala Glu Asp Asp Ile Gln Lys Leu
            340                 345                 350

Pro Tyr Phe Lys Ala Val Val Lys Glu Thr Leu Arg Leu Tyr Ala Pro
        355                 360                 365

Ala Pro Leu Ser Leu Pro Arg Leu Thr Ile Lys Ser Ser Val Ile Asp
    370                 375                 380

Gly Tyr Asp Ile Glu Pro Asn Thr Ile Val Tyr Val Asn Val Trp Ala
385                 390                 395                 400

Ile Ser Arg Asp Lys Asp Phe Trp Glu Asn Pro Asp Glu Phe Leu Pro
                405                 410                 415

Glu Arg Phe Leu Asn Ser Ser Val Asp Phe Lys Gly Gln Asp Phe Gly
            420                 425                 430

Phe Leu Pro Phe Gly Ser Gly Arg Arg Val Cys Pro Gly Met Ala Leu
        435                 440                 445

Gly Thr Ala Glu Val Glu Val Ser Leu Ala Asn Ile Leu Tyr Cys Phe
    450                 455                 460

His Trp Glu Leu Pro Pro Gly Met Val Glu Asp Asp Val Asp Met Asp
465                 470                 475                 480

Phe Leu Pro Gly Ile Thr Thr His Lys Lys Asn Ala Leu Tyr Leu Met
                485                 490                 495

Ala Lys Ser Tyr Leu
            500
```

<210> SEQ ID NO 55
<211> LENGTH: 1545
<212> TYPE: DNA
<213> ORGANISM: Sesamum indicum
<220> FEATURE:
<223> OTHER INFORMATION: SiP288

<400> SEQUENCE: 55

```
atggtgggaa ttgtgtatat tgagcttttc ttgtcagtta tgtggtttat ggctttgtgg      60
```

-continued

```
gtgtggttga attacagggc cctggcgtgg aactggcctg tgatcggaat gctgccgacg    120

cttctgcttc acgtgagccg gattcacgac aattgcacgg agattatggg gaagtcccga    180

cggggaactt ttcatttccg ggtccctgg ttggctgata tggacatgat ggggactgct     240

gatcctgaga atgttcacta cattatgagc gcgaacttcc agaatttccc gaaaggcccc    300

aagttcaggg aaatttttga tgttcttgga gatgggattt tcaatgcaga ttcggagtcc    360

tggagggacc agagaagggt tgccagggcc ctgatttctc accatggttt cctccggttt    420

ctggcgaaga tcagccgtga gaaggtagag aaaggcctga ttccagttct tgaaacggtg    480

tgcctggaaa atcgggtggt cgatttgcag gatttgttcc agaggttgac gtttgataca    540

acttgtacat ttgttactgg ttatgatcct ggatgcttgt ctgttgattt gcctgatgtt    600

cctttctcga aagccctaga tgatgccgaa gaagcgatat tcatgcgcca tgtggttcct    660

gaaaagattt ggaaacttca gaggtggttt ggggttggat ctgagagaaa attgagcaag    720

gctcgtgaag tcttggatag cgtcattggc aggtatatcg cgctgaagcg cggcgaaatg    780

agaagccgag gaatttcgat tgattgtgaa aatgaagatg gtgtggatct gctcacgtct    840

tacatgactg tgggagacga tggtactcaa acccatgatt tgaaatgtga tgacaagttc    900

ttgagggaca cgatactgaa tctaatgatt gcagggcggg acacgacgag ttctgctctg    960

acatggttta tatggcttgt gtcgacacat gctgaagtgg aaaagaggat cagggatgaa   1020

ctgaagtcct ttctgccccgc cggagaacgt gaaaagtggc gtgtgtttgg ggttgaagaa  1080

accaagaagt tggtttacat gcatggagca atttgcgaag ccctacgact atatccacca   1140

gtcccgttcc agcataagga gccggtggaa ccagatatcc ttccgagcgg gcattttgtg   1200

gaaccgacaa tgaaagtgat gttctcattg tacgccatgg gacggatgga atccgtttgg   1260

ggcgaggatt gcttggaatt caagccggag aggtggattt ctgatagggg atcgatcaag   1320

cacgagccct catacaagtt cttggctttc aatgctggtc cgaggacttg cttggggaag   1380

gatgtggctt tcgctcaggt gaaggcagtg gccgccacct taatccataa ctaccaagtt   1440

cacgtggcag acggccaccg cgtgctgccc aattgttcca tcatcctcta catgaggaat   1500

ggattgaagg ttagggttgc caatagatgg tctgctaaga aaaat                   1545
```

<210> SEQ ID NO 56
<211> LENGTH: 515
<212> TYPE: PRT
<213> ORGANISM: Sesamum indicum
<220> FEATURE:
<223> OTHER INFORMATION: SiP288

<400> SEQUENCE: 56

```
Met Val Gly Ile Val Tyr Ile Glu Leu Phe Leu Ser Val Met Trp Phe
  1               5                  10                  15

Met Ala Leu Trp Val Trp Leu Asn Tyr Arg Ala Leu Ala Trp Asn Trp
             20                  25                  30

Pro Val Ile Gly Met Leu Pro Thr Leu Leu Leu His Val Ser Arg Ile
         35                  40                  45

His Asp Asn Cys Thr Glu Ile Met Gly Lys Ser Arg Arg Gly Thr Phe
     50                  55                  60

His Phe Arg Gly Pro Trp Leu Ala Asp Met Asp Met Met Gly Thr Ala
 65                  70                  75                  80

Asp Pro Glu Asn Val His Tyr Ile Met Ser Ala Asn Phe Gln Asn Phe
                 85                  90                  95

Pro Lys Gly Pro Lys Phe Arg Glu Ile Phe Asp Val Leu Gly Asp Gly
```

-continued

```
            100                 105                 110

Ile Phe Asn Ala Asp Ser Glu Ser Trp Arg Asp Gln Arg Arg Val Ala
        115                 120                 125

Arg Ala Leu Ile Ser His His Gly Phe Leu Arg Phe Leu Ala Lys Ile
    130                 135                 140

Ser Arg Glu Lys Val Glu Lys Gly Leu Ile Pro Val Leu Glu Thr Val
145                 150                 155                 160

Cys Leu Glu Asn Arg Val Val Asp Leu Gln Asp Leu Phe Gln Arg Leu
                165                 170                 175

Thr Phe Asp Thr Thr Cys Thr Phe Val Thr Gly Tyr Asp Pro Gly Cys
            180                 185                 190

Leu Ser Val Asp Leu Pro Asp Val Pro Phe Ser Lys Ala Leu Asp Asp
        195                 200                 205

Ala Glu Glu Ala Ile Phe Met Arg His Val Val Pro Glu Lys Ile Trp
    210                 215                 220

Lys Leu Gln Arg Trp Phe Gly Val Gly Ser Glu Arg Lys Leu Ser Lys
225                 230                 235                 240

Ala Arg Glu Val Leu Asp Ser Val Ile Gly Arg Tyr Ile Ala Leu Lys
                245                 250                 255

Arg Gly Glu Met Arg Ser Arg Gly Ile Ser Ile Asp Cys Glu Asn Glu
            260                 265                 270

Asp Gly Val Asp Leu Leu Thr Ser Tyr Met Thr Val Gly Asp Asp Gly
        275                 280                 285

Thr Gln Thr His Asp Leu Lys Cys Asp Asp Lys Phe Leu Arg Asp Thr
    290                 295                 300

Ile Leu Asn Leu Met Ile Ala Gly Arg Asp Thr Thr Ser Ser Ala Leu
305                 310                 315                 320

Thr Trp Phe Ile Trp Leu Val Ser Thr His Ala Glu Val Glu Lys Arg
                325                 330                 335

Ile Arg Asp Glu Leu Lys Ser Phe Leu Pro Ala Gly Glu Arg Glu Lys
            340                 345                 350

Trp Arg Val Phe Gly Val Glu Glu Thr Lys Lys Leu Val Tyr Met His
        355                 360                 365

Gly Ala Ile Cys Glu Ala Leu Arg Leu Tyr Pro Pro Val Pro Phe Gln
    370                 375                 380

His Lys Glu Pro Val Glu Pro Asp Ile Leu Pro Ser Gly His Phe Val
385                 390                 395                 400

Glu Pro Thr Met Lys Val Met Phe Ser Leu Tyr Ala Met Gly Arg Met
                405                 410                 415

Glu Ser Val Trp Gly Glu Asp Cys Leu Glu Phe Lys Pro Glu Arg Trp
            420                 425                 430

Ile Ser Asp Arg Gly Ser Ile Lys His Glu Pro Ser Tyr Lys Phe Leu
        435                 440                 445

Ala Phe Asn Ala Gly Pro Arg Thr Cys Leu Gly Lys Asp Val Ala Phe
    450                 455                 460

Ala Gln Val Lys Ala Val Ala Ala Thr Leu Ile His Asn Tyr Gln Val
465                 470                 475                 480

His Val Ala Asp Gly His Arg Val Leu Pro Asn Cys Ser Ile Ile Leu
                485                 490                 495

Tyr Met Arg Asn Gly Leu Lys Val Arg Val Ala Asn Arg Trp Ser Ala
            500                 505                 510

Lys Lys Asn
        515
```

<210> SEQ ID NO 57
<211> LENGTH: 1494
<212> TYPE: DNA
<213> ORGANISM: Sesamum indicum
<220> FEATURE:
<223> OTHER INFORMATION: SiP168

<400> SEQUENCE: 57

```
atggatctac tactttccct tgttctccta ctctgttctg cagcatgcat ttggtttctc     60

cgggtggtcc tgaaacccaa tccagggccc cggaaatcag ccaatctccc tccagggcca    120

aaacctcttc ccataatcgg caacattctt gagcttggtg agaaacccca ccaatctctc    180

gccaaactct ccaaaaccta cgggcccctg atgcgtctca agctgggaac catgacaaca    240

gttgttgtat cctccccgga aatctccagg atcgtgctgc aacaatatga ccaagttttc    300

tccagccgaa cacacgcaga tgccatccga gcacttgacc accacaaaca ttccgtcgcc    360

tggataccgg cggacaatca gtggcggaaa atccgtaaac tgtgcaaaga gaagatgttt    420

tcgggccaaa agcttgatgc gaaccagggc ctgaggaggg agaagttgcg taatttgcaa    480

gactatgtga atgaatgctg cgttagtggc caggtcgtgg atattggtgt agctgccttt    540

acgacgaccc ttaatctgat atcggccact cttttctcgg tggattttgc tgattttggt    600

tctggttcgt ctcaagagct taaggatgtt atgagcggga tagcgtctat catcggccga    660

ccaaattttg ctgattgttt ccctcttctt cggctggttg atccacaggg catcttccgc    720

cagaccacgt tacatttcaa caagtgtttt aagatctttg atgaaattat ccgtcaaagg    780

ctacagacca atgattcggg gacgaaaagt gacatgctga aagagcttct tgaaatcaac    840

cagaaagatg agtctgaatt gagctttgac gagatcaagc atttactcct ggatctactt    900

gtcgcaggaa cggacacaac ttcagttaca gtggaatggg caatgacgga gctagtgcgc    960

caccctgaga aaatgtcgaa agccagaaat gagttaagaa atgtggtggg actgaataaa   1020

gaaattcaag aatcagacat ctcaagactc ccttacctac gagcagtggt gaaagaaagt   1080

ttcaggcttc accctgcaac tcctttatcg gtacctcaca aggccgacga ggaagcagaa   1140

atcaatggct atatagtccc taaaggagca caagttctca tgaacgtgtg ggccatcggc   1200

agagattcaa gcatatggag gaaccctgat gtattcatgc ccgagaggtt cttggagaca   1260

gaaattgatg tccgtggcca acacttcgag ctgcttcctt ttggcggggg gaggaggatt   1320

tgcgtggggc tgccgttagc ctatcgtatg atccatctcg tgcttgccac tttcataagc   1380

gactatgatt ggaaacttga aggagggctg aaaactgaag aaatggacat gagtgaaaag   1440

ttcggcctca ccctgcaaaa agccattcct ctcaaggcac ttccagttaa aatt          1494
```

<210> SEQ ID NO 58
<211> LENGTH: 498
<212> TYPE: PRT
<213> ORGANISM: Sesamum indicum
<220> FEATURE:
<223> OTHER INFORMATION: SiP168

<400> SEQUENCE: 58

```
Met Asp Leu Leu Leu Ser Leu Val Leu Leu Leu Cys Ser Ala Ala Cys
  1               5                  10                  15

Ile Trp Phe Leu Arg Val Val Leu Lys Pro Asn Pro Gly Pro Arg Lys
             20                  25                  30

Ser Ala Asn Leu Pro Pro Gly Pro Lys Pro Leu Pro Ile Ile Gly Asn
         35                  40                  45
```

-continued

```
Ile Leu Glu Leu Gly Glu Lys Pro His Gln Ser Leu Ala Lys Leu Ser
     50                  55                  60

Lys Thr Tyr Gly Pro Leu Met Arg Leu Lys Leu Gly Thr Met Thr Thr
 65                  70                  75                  80

Val Val Val Ser Ser Pro Glu Ile Ser Arg Ile Val Leu Gln Gln Tyr
                 85                  90                  95

Asp Gln Val Phe Ser Ser Arg Thr His Ala Asp Ala Ile Arg Ala Leu
            100                 105                 110

Asp His His Lys His Ser Val Ala Trp Ile Pro Ala Asp Asn Gln Trp
        115                 120                 125

Arg Lys Ile Arg Lys Leu Cys Lys Glu Lys Met Phe Ser Gly Gln Lys
    130                 135                 140

Leu Asp Ala Asn Gln Gly Leu Arg Arg Glu Lys Leu Arg Asn Leu Gln
145                 150                 155                 160

Asp Tyr Val Asn Glu Cys Cys Val Ser Gly Gln Val Val Asp Ile Gly
                165                 170                 175

Val Ala Ala Phe Thr Thr Thr Leu Asn Leu Ile Ser Ala Thr Leu Phe
            180                 185                 190

Ser Val Asp Phe Ala Asp Phe Gly Ser Gly Ser Ser Gln Glu Leu Lys
        195                 200                 205

Asp Val Met Ser Gly Ile Ala Ser Ile Ile Gly Arg Pro Asn Phe Ala
    210                 215                 220

Asp Cys Phe Pro Leu Leu Arg Leu Val Asp Pro Gln Gly Ile Phe Arg
225                 230                 235                 240

Gln Thr Thr Leu His Phe Asn Lys Cys Phe Lys Ile Phe Asp Glu Ile
                245                 250                 255

Ile Arg Gln Arg Leu Gln Thr Asn Asp Ser Gly Thr Lys Ser Asp Met
            260                 265                 270

Leu Lys Glu Leu Leu Glu Ile Asn Gln Lys Asp Glu Ser Glu Leu Ser
        275                 280                 285

Phe Asp Glu Ile Lys His Leu Leu Leu Asp Leu Leu Val Ala Gly Thr
    290                 295                 300

Asp Thr Thr Ser Val Thr Val Glu Trp Ala Met Thr Glu Leu Val Arg
305                 310                 315                 320

His Pro Glu Lys Met Ser Lys Ala Arg Asn Glu Leu Arg Asn Val Val
                325                 330                 335

Gly Leu Asn Lys Glu Ile Gln Glu Ser Asp Ile Ser Arg Leu Pro Tyr
            340                 345                 350

Leu Arg Ala Val Val Lys Glu Ser Phe Arg Leu His Pro Ala Thr Pro
        355                 360                 365

Leu Ser Val Pro His Lys Ala Asp Glu Glu Ala Glu Ile Asn Gly Tyr
    370                 375                 380

Ile Val Pro Lys Gly Ala Gln Val Leu Met Asn Val Trp Ala Ile Gly
385                 390                 395                 400

Arg Asp Ser Ser Ile Trp Arg Asn Pro Asp Val Phe Met Pro Glu Arg
                405                 410                 415

Phe Leu Glu Thr Glu Ile Asp Val Arg Gly Gln His Phe Glu Leu Leu
            420                 425                 430

Pro Phe Gly Gly Gly Arg Arg Ile Cys Val Gly Leu Pro Leu Ala Tyr
        435                 440                 445

Arg Met Ile His Leu Val Leu Ala Thr Phe Ile Ser Asp Tyr Asp Trp
    450                 455                 460
```

-continued

```
Lys Leu Glu Gly Gly Leu Lys Thr Glu Glu Met Asp Met Ser Glu Lys
465                 470                 475                 480

Phe Gly Leu Thr Leu Gln Lys Ala Ile Pro Leu Lys Ala Leu Pro Val
                485                 490                 495

Lys Ile


<210> SEQ ID NO 59
<211> LENGTH: 1545
<212> TYPE: DNA
<213> ORGANISM: Sesamum indicum
<220> FEATURE:
<223> OTHER INFORMATION: SiP236

<400> SEQUENCE: 59

atggcaaacc ccattgattt tctcctcagc ccaacaccat atgtggctac aacccttctt      60

tacgttctct tctctgttct tattgttaga ttcctcagca gaaagctgct cgggaagaag     120

aggtaccatc ccattggtgg taccgtgttc aaccagctgc tgaacttcta taggttgcat     180

gattatatgg ctgatcttgc agggaagtac aagacttaca gactgattgc cccttttcgg     240

actgaggtct atacatctga ccccgctaat gttgagcaca tgttgaaaac gaatttcgaa     300

agttatggca agggacctta caattgcagc attctggggg atttgtttgg tgaaggaatt     360

ttcgcaatcg atggccataa gtggagggag cagagaaaag tgtcaagcct tgagttttct     420

acaagggttc tgagggatta cagtagcatc gtcttcagga aaaacgccgt aaggctcgca     480

aaaattctgt ctggagctgc aacttccaac caaccagtgg atattcaaga tcttttcatg     540

aaatcaactt ttgattctat ttcggaagtt gctttaggag ttgagcttga cagcttgggt     600

ggttcaaatg aagaaggtgc caaatttagc attgctgcag acgacgtgag tatgaggaca     660

ctttggagat acgtggatgt tctgtggaag ttaaagagag ctctaaatgt tggttcagaa     720

gcaaaactga agaaaagcct tcaagtggtt gatgaatttg tgtataagct gattcatagt     780

aggactcagc aaatgaacat gccaggaaat gattctgtta tgcagctgaa gaaagacgac     840

attttgtcaa gattcttgca acttactgag gccactccca agtacttgag ggacataaca     900

ataagcttta tagttgctgg taaagacaca acagcaacaa ctctctcctg gtttatttac     960

atgctttgca agtatcctca tgttcaggaa aaggtggagc aagagataaa agatgcgaca    1020

ggctgcaaag aggtagcaga tatctcagaa ttttcagcct gtgtgacaga agaagctttg    1080

ggcaagatgc attatctcca tgcagcattg acagaaacac tgaggattta tccagcagtt    1140

gcggtggatg caaagcaatg tttgtgtgat gatataatgc cggatgggtt cagtgttaag    1200

aagggggaca tggtggctta tcaaccatat gcaatgggaa ggatgaaatc catatggggt    1260

aatgatgcag aagagttcaa accagagaga tggcttgaca aaaacggttg cttccagcag    1320

gccagccctt ttaagtttac agctttccag gccggccctc gtctttgttt ggggaaagag    1380

tttgcttatc ggcagatgaa gatattctca gccattctgc tgagattctt taccatgaaa    1440

ctaagtgatg aaagaaagac agtaaactac agaccaatgc tcactcttct catcgacggt    1500

ggtctcattg tccgcccctt tcacagaatg gacgagaaaa ctgca                    1545


<210> SEQ ID NO 60
<211> LENGTH: 515
<212> TYPE: PRT
<213> ORGANISM: Sesamum indicum
<220> FEATURE:
<223> OTHER INFORMATION: SiP236

<400> SEQUENCE: 60
```

-continued

```
Met Ala Asn Pro Ile Asp Phe Leu Leu Ser Pro Thr Pro Tyr Val Ala
 1               5                  10                  15

Thr Thr Leu Leu Tyr Val Leu Phe Ser Val Leu Ile Val Arg Phe Leu
            20                  25                  30

Ser Arg Lys Leu Leu Gly Lys Lys Arg Tyr His Pro Ile Gly Gly Thr
        35                  40                  45

Val Phe Asn Gln Leu Leu Asn Phe Tyr Arg Leu His Asp Tyr Met Ala
    50                  55                  60

Asp Leu Ala Gly Lys Tyr Lys Thr Tyr Arg Leu Ile Ala Pro Phe Arg
65                  70                  75                  80

Thr Glu Val Tyr Thr Ser Asp Pro Ala Asn Val Glu His Met Leu Lys
                85                  90                  95

Thr Asn Phe Glu Ser Tyr Gly Lys Gly Pro Tyr Asn Cys Ser Ile Leu
            100                 105                 110

Gly Asp Leu Phe Gly Glu Gly Ile Phe Ala Ile Asp Gly His Lys Trp
        115                 120                 125

Arg Glu Gln Arg Lys Val Ser Ser Leu Glu Phe Ser Thr Arg Val Leu
    130                 135                 140

Arg Asp Tyr Ser Ser Ile Val Phe Arg Lys Asn Ala Val Arg Leu Ala
145                 150                 155                 160

Lys Ile Leu Ser Gly Ala Ala Thr Ser Asn Gln Pro Val Asp Ile Gln
                165                 170                 175

Asp Leu Phe Met Lys Ser Thr Phe Asp Ser Ile Ser Glu Val Ala Leu
            180                 185                 190

Gly Val Glu Leu Asp Ser Leu Gly Gly Ser Asn Glu Glu Gly Ala Lys
        195                 200                 205

Phe Ser Ile Ala Ala Asp Asp Val Ser Met Arg Thr Leu Trp Arg Tyr
    210                 215                 220

Val Asp Val Leu Trp Lys Leu Lys Arg Ala Leu Asn Val Gly Ser Glu
225                 230                 235                 240

Ala Lys Leu Lys Lys Ser Leu Gln Val Val Asp Glu Phe Val Tyr Lys
                245                 250                 255

Leu Ile His Ser Arg Thr Gln Gln Met Asn Met Pro Gly Asn Asp Ser
            260                 265                 270

Val Met Gln Leu Lys Lys Asp Asp Ile Leu Ser Arg Phe Leu Gln Leu
        275                 280                 285

Thr Glu Ala Thr Pro Lys Tyr Leu Arg Asp Ile Thr Ile Ser Phe Ile
    290                 295                 300

Val Ala Gly Lys Asp Thr Thr Ala Thr Thr Leu Ser Trp Phe Ile Tyr
305                 310                 315                 320

Met Leu Cys Lys Tyr Pro His Val Gln Glu Lys Val Glu Gln Glu Ile
                325                 330                 335

Lys Asp Ala Thr Gly Cys Lys Glu Val Ala Asp Ile Ser Glu Phe Ser
            340                 345                 350

Ala Cys Val Thr Glu Glu Ala Leu Gly Lys Met His Tyr Leu His Ala
        355                 360                 365

Ala Leu Thr Glu Thr Leu Arg Ile Tyr Pro Ala Val Ala Val Asp Ala
    370                 375                 380

Lys Gln Cys Leu Cys Asp Asp Ile Met Pro Asp Gly Phe Ser Val Lys
385                 390                 395                 400

Lys Gly Asp Met Val Ala Tyr Gln Pro Tyr Ala Met Gly Arg Met Lys
                405                 410                 415
```

-continued

```
Ser Ile Trp Gly Asn Asp Ala Glu Glu Phe Lys Pro Glu Arg Trp Leu
            420                 425                 430

Asp Lys Asn Gly Cys Phe Gln Gln Ala Ser Pro Phe Lys Phe Thr Ala
        435                 440                 445

Phe Gln Ala Gly Pro Arg Leu Cys Leu Gly Lys Glu Phe Ala Tyr Arg
    450                 455                 460

Gln Met Lys Ile Phe Ser Ala Ile Leu Leu Arg Phe Phe Thr Met Lys
465                 470                 475                 480

Leu Ser Asp Glu Arg Lys Thr Val Asn Tyr Arg Pro Met Leu Thr Leu
                485                 490                 495

Leu Ile Asp Gly Gly Leu Ile Val Arg Pro Phe His Arg Met Asp Glu
            500                 505                 510

Lys Thr Ala
        515


<210> SEQ ID NO 61
<211> LENGTH: 34
<212> TYPE: DNA
<213> ORGANISM: Artificial Sequence
<220> FEATURE:
<223> OTHER INFORMATION: Description of Artificial Sequence:
      Artificially Synthesized Primer Sequence, Bam-SST-FW2

<400> SEQUENCE: 61

tggatcccaa ctcatagagt actcaaaaac gctt                                 34


<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence:
      Artificially Synthesized Primer Sequence, SiP189-Nco-RV

<400> SEQUENCE: 62

gcaaatgatc aaccatggtg ttct                                            24


<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence:
      Artificially Synthesized Primer Sequence, GR-SST-RV1

<400> SEQUENCE: 63

cacatgaacg agacgaactg ggtttgg                                         27


<210> SEQ ID NO 64
<211> LENGTH: 506
<212> TYPE: PRT
<213> ORGANISM: Sesamum radiatum
<220> FEATURE:
<223> OTHER INFORMATION: SrSiP189

<400> SEQUENCE: 64

Met Glu Ala Glu Met Leu Tyr Ser Ala Leu Ala Leu Thr Phe Ala Ile
  1               5                  10                  15

Phe Met Val Tyr Arg Ile Leu Ser Asn Ser Gln Glu Lys Ser Ser Leu
             20                  25                  30

Ile Lys Leu Pro Pro Ser Pro Pro Gly Trp Leu Pro Val Ile Gly His
         35                  40                  45
```

-continued

```
Val His Leu Met Lys Asn Leu Leu His Arg Thr Leu Tyr Asp Phe Ser
     50                  55                  60

Gln Lys Leu Gly Pro Ile Phe Ser Leu Arg Phe Gly Thr Arg Leu Val
 65                  70                  75                  80

Val Val Val Ser Ser Ser Ser Leu Val Glu Glu Cys Phe Thr Lys Tyr
                 85                  90                  95

Asp Ile Val Leu Ala Asn Arg Pro Gln Pro Ser Val Asp Arg Arg Ser
            100                 105                 110

Leu Gly Phe Ser Thr Thr Ser Val Ile Gly Ala Pro Tyr Gly Asp His
        115                 120                 125

Trp Arg Asn Leu Arg Lys Leu Cys Asp Leu Glu Val Phe Ala Pro Thr
    130                 135                 140

Arg Leu Ala Ser Phe Leu Ser Ile Arg Leu Asp Glu Arg Asp Arg Met
145                 150                 155                 160

Ile Ser Ser Leu Tyr Lys Ile Ser Ser Ala Gly Phe Ala Lys Val Asn
                165                 170                 175

Leu Glu Thr Lys Ile Val Glu Leu Thr Phe Asn Asn Ile Met Arg Met
            180                 185                 190

Val Ala Gly Lys Arg Tyr Tyr Gly Glu Glu Ala Glu Asp Asp Glu Glu
        195                 200                 205

Ala Lys Arg Phe Arg Asp Leu Thr Lys Glu Ala Leu Glu Leu Thr Ser
    210                 215                 220

Ala Ser Asn Pro Gly Glu Ile Phe Pro Ile Leu Arg Trp Leu Gly Phe
225                 230                 235                 240

Asn Gly Leu Glu Lys Lys Leu Ala Val His Ala Arg Lys Thr Asp Glu
                245                 250                 255

Phe Met Gln Gly Leu Leu Asp Glu His Arg Arg Gly Glu Arg Gln Asn
            260                 265                 270

Thr Met Val Asp His Leu Leu Ser Leu Gln Glu Ser Gln Pro Glu Tyr
        275                 280                 285

Tyr Thr Asp Glu Ile Ile Thr Gly Leu Ile Val Ala Leu Ile Ile Ala
    290                 295                 300

Gly Thr Asp Ala Ser Val Val Thr Thr Glu Trp Ala Met Ser Leu Ile
305                 310                 315                 320

Leu Asn His Pro Gln Val Leu Glu Lys Ala Arg Lys Glu Leu Asp Thr
                325                 330                 335

Leu Val Gly His Glu Arg Met Val Asp Glu His Asp Leu Pro Lys Leu
            340                 345                 350

Arg Tyr Leu His Cys Ile Val Leu Glu Thr Leu Arg Leu Phe Pro Ser
        355                 360                 365

Val Pro Thr Leu Val Pro His Glu Pro Ser Glu Asp Cys Lys Ile Gly
    370                 375                 380

Gly Tyr Asn Val Pro Lys Gly Thr Met Ile Leu Val Asn Ala Trp Ala
385                 390                 395                 400

Ile His Arg Asp Pro Lys Val Trp Asp Asp Pro Leu Ser Phe Lys Pro
                405                 410                 415

Asp Arg Phe Glu Thr Met Glu Val Glu Thr His Lys Leu Leu Pro Phe
            420                 425                 430

Gly Met Gly Arg Arg Ala Cys Pro Gly Ala Gly Leu Ala Gln Lys Phe
        435                 440                 445

Val Gly Leu Ala Leu Gly Ser Leu Ile Gln Cys Phe Glu Trp Glu Arg
    450                 455                 460

Met Ser Ala Glu Lys Ile Asp Leu Asn Glu Gly Ser Gly Ile Thr Leu
```

-continued

```
465                 470                 475                 480

Pro Lys Ala Lys Thr Leu Glu Ala Met Cys Lys Pro Arg His Ile Met
                485                 490                 495

Glu Arg Val Leu Arg Gln Val Ser Asn Val
            500                 505


<210> SEQ ID NO 65
<211> LENGTH: 1518
<212> TYPE: DNA
<213> ORGANISM: Sesamum radiatum
<220> FEATURE:
<223> OTHER INFORMATION: SrSiP189

<400> SEQUENCE: 65

atggaagctg aaatgctata ttcagctctc gctctcacct tcgccatatt catggtttac     60

agaattcttt ctaattcgca ggagaaaagc agcctgatta agctgccgcc gagcccgccg    120

ggttggctcc cggtgatcgg ccacgttcat ctcatgaaaa atctcctcca tagaacacta    180

tacgacttct cccagaaact gggacccata ttttccctcc ggttcggcac ccgcctcgtg    240

gtagtggtgt cctcctcctc cctggtcgag gaatgtttca ccaagtacga cattgtcttg    300

gccaaccgcc ctcagccctc tgtcgaccgg cgctcactcg ggttcagcac caccagcgta    360

atcggcgccc cgtacgggga ccattggcgc aacctgcgaa agttgtgcga tcttgaagta    420

ttcgccccga cccgtctcgc ctcgttttta tccatcaggc ttgacgagag ggaccgcatg    480

atttcgtcgt tgtacaaaat ctcgtccgcc ggtttcgcga aggtgaattt ggagacgaag    540

attgttgagc tgacgtttaa taacataatg aggatggtgg cggggaagag atactatggg    600

gaggaggcgg aggacgacga ggaggcgaag aggttcaggg acctgacgaa ggaggctttg    660

gagttgacga gcgcttccaa tcctggtgag atatttccaa tattgcggtg gcttggtttc    720

aatgggttgg agaagaagct ggctgttcac gcgcggaaga cggatgagtt catgcaaggg    780

ctgctggacg aacaccgacg gggcgagcgc cagaacacca tggttgatca tttgctttcg    840

ttgcaggaat ctcaacctga gtactacact gatgaaatca tcactggcct catagttgca    900

ttgataattg cgggaacgga tgcatcggtt gtaactacag aatgggcgat gtcccttata    960

ctaaatcatc cccaagtact tgaaaaggct agaaaagaac tggacactct agtaggacac   1020

gaacgcatgg tcgatgaaca tgatctgccc aaactacgtt accttcactg catagtcttg   1080

gagaccttaa ggttatttcc ttctgttcca acgttggtgc cacacgaacc atcggaggat   1140

tgtaaaattg gggatacaa tgtccccaag ggacaatga tactggtgaa tgcttgggca     1200

atacaccgag accccaaggt gtgggacgac cccttgagct ttaagcccga caggtttgag   1260

acaatggaag tggagacaca caagctgttg ccgttcggga tgggcaggag agcgtgtccc   1320

ggagctggat tggcgcagaa gtttgtgggg ttggctttgg ggtcgctgat tcagtgtttc   1380

gagtgggaga gaatgagtgc ggagaaaatt gacttgaacg aaggttctgg gataaccttg   1440

cctaaagcta agacgttgga agccatgtgc aaacctagac atatcatgga gagagttctt   1500

cgtcaggttt cgaacgtc                                                 1518


<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence:
      Artificially Synthesized Primer Sequence, NtUBQ-FW
```

```
<400> SEQUENCE: 66

ggaatgcaga tcttcgtcaa                                                   20


<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence:
      Artificially Synthesized Primer Sequence, NtUBQ-RW

<400> SEQUENCE: 67

cctagaaacc accacgga                                                     18


<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence:
      Artificially Synthesized Primer Sequence, SiP189-bam-FW

<400> SEQUENCE: 68

ttttcagcca acatggaagc tgaa                                              24


<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence:
      Artificially Synthesized Primer Sequence, SiP189-nco-RV

<400> SEQUENCE: 69

gcaaatgatc aaccatggtg ttct                                              24


<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence:
      Artificially Synthesized Primer Sequence, STAR-LF1

<400> SEQUENCE: 70

acgaagttat gcggccaatt aaccc                                             25


<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence:
      Artificially Synthesized Primer Sequence, STAR-LR1

<400> SEQUENCE: 71

ccacctgacg tcgcggccta atacg                                             25


<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence:
      Artificially Synthesized Primer Sequence, M13-47(F)

<400> SEQUENCE: 72
```

```
cgccagggtt ttcccagtca cgac                                          24


<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence:
      Artificially Synthesized Primer Sequence, RV-M(R)

<400> SEQUENCE: 73

gagcggataa caatttcaca cagg                                          24


<210> SEQ ID NO 74
<211> LENGTH: 3069
<212> TYPE: DNA
<213> ORGANISM: Sesamun indium

<400> SEQUENCE: 74

tacgtggttg taaattaagg tggcatagtc aaagctgtgt aggatggagg aattagacac     60

ttccccagtc ccccacagac tattcccgag ctgaccaaac acagtcgaaa gtgtggggcc    120

caatgaaatt gacagatgac gtctagtgta gtgtgaatgt gtgatatttt tgcagaatat    180

tgtaaaagag ggttcaccaa atctcactag tttgtgacta attgactatt tttgcagaaa    240

attcgtattt agtatagggt cttggtcaaa ttaattaatt atataacaaa tgtgatatat    300

ttaatttgtt attaattttt ttatatttgt tgtgtaatta gttaggattt tatataagaa    360

tttgaaaaaa tgagatgttt ttttgtaaat caaattacac aatatcatgt attgggtttt    420

tcgtcctgaa gtcgcttgaa aattgattag atcggcggac ttgaacagac gagtgaatgg    480

acatgattta aaattttaag gataaatata tatagtatca gttatcaaaa taaaaaattt    540

ccttcaaaat catggtcttg tttaagatag ttttttgagt aatgtggcac cataattccc    600

aagcactaga agtgcaattg taaatccaac ggtacctagt ttaattgata aaattaaagt    660

ccaaaaattt tcctgagaaa ccaattcgag caagggtaca tcaaaggtgc caccagggag    720

ttaagcaaga aatgtcccct aaactttagg catgaggtat ccctataaaa taaattgacc    780

taaaaagatt caaatggctt agagtcgaga aaaagactaa gtagaccatt agggaagccc    840

acatgcctaa gatcctccag ccgaagtaga ggcctatgcg gcagtcagcc tagtgacttg    900

ggattcccta gctctgaaag aattaatatt gtcccaagaa tctaaggcta catagtagaa    960

atgaaaacaa agcgaattta aatttgaagc cagcatgatt gaattttttt ttttttttc    1020

aggtgtttaa gcactcaaac atgtacaata aataaacgtg tggctaattt aaagaacatt   1080

gaaagctggc caagaattat accttttaaa gcgagtggag tttccgatgt ttgagctctc   1140

attcaatccg ttcacatcta gatgaacaaa cgtctctttt aatggtatcc acgatacctt   1200

tgtcgagggg atttctcgtc tccttgctag aggattcaat attaccaagg ggtcaaaact   1260

atactaactt aaagaagatt gagaacacac tattaaattc tcgatcccaa ttttcaagcc   1320

tttgcaccta gttgaaagct tgtgcgtaga gatgcttttg agagagtgtc ggggaggaga   1380

ggggatggaa cacaaaattt taggcttatt ttttcttttt tttttttgtc aaaaatgtct   1440

ctgttaaagt tttgtgcatg tcctctatat gccaaatatt tggtggtaag cacgacaaag   1500

gtatgccaaa tgaagttgta ttaactatgt tgaataagat ggtcctatac taatagatta   1560

cataggccaa cccattagct tgtaggtcac atattccaac ataatgtaga ggtctaagca   1620

caagcagacc catgccatat ggcgtccatg gggtagtcca ggtgatattg acgtaagttc   1680
```

ttttaagcca catcaacaaa cttcagccgt ccaagcaagg acatgtggcc gcctcaaaag 1740
aaggcctcaa tgcttcctta tccctaaaac aactctagct ttggaaacca gatcagatga 1800
ggatatcccc taagctattt caaaaaatct aggaacctta tctgtagcag actttgttaa 1860
tttttcaaat caagggactc caacagccaa gcgataaccc tcaccaaatt tgtgaaggat 1920
tcgatattat ccaaccagtt gatgatttgc ttataaagtg caatcttccc ccaacaaaaa 1980
agccaattcc aacttttact ttcaaattat agctttaatt tctgacttaa aatttcatat 2040
tataaatttc aatctcttaa gtgtacacaa aatacaagat atttcactct tttgtatttt 2100
tctaattccc ataattttat ctttattttg tattttgatt gaacccgagc acatctttga 2160
cttgcatcaa caatattagc tctaaattaa acatagaatt taatgttaaa atgagaaaag 2220
gaactcatac agatcggact caaaacctta acacctaata aagtatgcat cctaataaaa 2280
agttattacc aaagtgaaat tatgcttaat gaaaatcgaa atcagaagta gttcttaatt 2340
ggagagtttc gagacggcaa gaatattgca actcatcctc acacctaccc atctatttca 2400
tactcttaaa ttataatcta attcaatata cacaacaacc tatcacatta atatacaata 2460
tgaaaggtca ataaaatatt tacgctggca aacctcccca gtagaattcg ggcacatatg 2520
aagtgttaac cattcaaata tggacaaagg aacactagag acacgaagtt tatttcaaag 2580
gaaaattttg tctaaaattg aatttaatta aatttaaatt aattatataa taaatataat 2640
gtattttaca tcatgattga tatataattt taaaaaaaat aattattcca actattaaca 2700
ttaattaata aataactttt acaagaccca ggccaccaac tcccgtccac atgaaagaat 2760
gggtaaccgc taagtctata ttttagtact acgacgtatg caaatacgct ttttccacaa 2820
aaatcaaatt ttaattttta ctttatccaa ggcaagaaaa caaaaaatgc ataaattcac 2880
gttctaattc atcaatactc aagaaatagc atacttgatt tgaactgaga tttgtcactt 2940
tcctacaaat tctgcagact atgaaaacga catcaaccaa ccaatatcca ctctctatat 3000
aaatagcatc acttcactag caatttctca tcaactcata gagtactcaa aaacgctttt 3060
tcagccaac 3069

<210> SEQ ID NO 75
<211> LENGTH: 29
<212> TYPE: DNA
<213> ORGANISM: Artificial Sequence
<220> FEATURE:
<223> OTHER INFORMATION: Description of Artificial Sequence: Artificially Synthesized Primer Sequence, gSST-FW1

<400> SEQUENCE: 75
aatgaaattg acagatgacg tctagtgta 29

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Artificially Synthesized Primer Sequence, gSST-RV2

<400> SEQUENCE: 76
ctgcgaatta gaaagaattc tgtaaaccat 30

<210> SEQ ID NO 77
<211> LENGTH: 2815
<212> TYPE: DNA

<213> ORGANISM: Sesamum radiatum
<220> FEATURE:
<221> NAME/KEY: misc_feature
<222> LOCATION: (2199)..(2199)
<223> OTHER INFORMATION: n stands for any base

<400> SEQUENCE: 77

```
tagtgtagtg tgaatgtgtg atatttttgc agtatatata ttgtaaaaga ggattaacca      60

aatctctcta gttcgtgatt atgactattt ttgcagaaaa tttgtattta gtttagggtt     120

ggtaaaatct aatttataga gtaaatatga tgtatttatt ttgtgattga ttacttttat     180

atttattgta taattagtta taatttgata aagtgtgata ttttttataa attagattac     240

atattattat gtactgagtt tttcgttctg atgccattta aaaattggtt aggtcggcga     300

cttgaactga cgagtgaagg gacttgattt aacattttaa ggatatatat atatagtacc     360

agttatcaaa ataaaagttt tctttcaaaa tcatagtttt gtttaagata attttgtgag     420

tatatgttgc accacaattc ccaagcacta taagtgcaac tgtaggtcta attggaccta     480

gtttagttga caaaattgaa gtccaagaat atcttcaaga agccaattcg tgtaatggta     540

cgtcaaaggt gccaccaggg aatcaagtag gaaatttccc ctaaatgtta ggcatgaggt     600

gccactataa agaaaattga cccaaagaga tacaagtatc ttagagtcga gaagaagact     660

acgtagacca ttagggaagt ccacatgcct aagattctgc agctgaagca caggcctagg     720

tacggtcagc ccagggactc gagatcccct agctctcaaa gaattggtat tggcccagga     780

atctaaggct acatagcaaa aacgaaaata aaacaaactt aaatttgaag tcaacgggat     840

tgaatcctat tttctcgggt gttcaaactc aagcatgtaa aataaataaa cgtgtgacta     900

atttacaaaa cactgaaaac taattacaaa ttatacctta aaagcatgtg tagtttttaa     960

cgtttgagct ttcgtcaatc cattcacgta gagataaacg gacgtctcct ctaagggtat    1020

ccacaatacc attggcgagg agatttcttg tctattagag gattcgagat taccatggag    1080

ttagaactat aaacctaaag aagatcgaga aaatactatt agattagtgt tctcaatctc    1140

aattctcaag ccttcaaacc tagttaaaag cttgagaaaa tttgtgcgta gatatgtttt    1200

ggagagagtg tcggagagaa gaggggatcg agcacaaact cttagcccta ttcttttctc    1260

ttctttgccg aaaaatgtct ttgttagagt ccttgtgcat gttttctata tgccaaatat    1320

gtggtggtaa gcacaacaaa gttatgtgaa aagaaattgt attagcacta cgttgaataa    1380

gattgtcttc tactaataga tgatagaggg caaccattgg cttgtcggtt acttattcca    1440

acataatgta gaggcccaag catgataaga cctatgccac aggacgtcct tgggtggtcc    1500

aagtgatatt gacgtaagac cttttaacct acttcggcag gctttagcca taacctccag    1560

cctgtgaaac ccgatcagat gaggatatcc cctcagcccc tccaaaaatc taggaatctc    1620

atccgcagca gatttcggta tcttttccta gaagatcaaa aaactctaac cactaagaga    1680

taaccccccc cacaaaatta atggaaaatt tggccttatc taactggcta ataggttgcc    1740

cataaattgc gagctccccc aacataaaaa gccaatccaa ctttactttt aaattatagg    1800

tttagtttct aacttaaaat ttcatattat gaatatcaac ctcttatgta tacacaaagt    1860

aacaagatat tttactcatt tgttttctct tagttcctat aattttatct ttcttgcatc    1920

aacaatattt gctctaaatt aaatatagaa tttaatgtta aaatgagaaa acggactcaa    1980

aaccagaaca cctaataaag tatgcatctt aataaaaagt tattacgaag gagaaaaata    2040

tgcttaataa aaatcgaaat cagaagtagt tcttaattgg agagtctgaa aacggcaaga    2100

atattgcaag tcatcctcac tttctcatcc atagacagtc acacctaccc cacatatttc    2160
```

```
atacttttaa attattatct aatttaatat acgcatcant tcataatata taatacgaaa   2220

ggttaataaa atatttacgc tagcaaactt cttcagtaga attcatgtac ataagaagtg   2280

ttgaccattc aaatatggaa aaagaaacac tagagataag aaacttagtt gtgaagcaga   2340

aaatatttaa gttggttggt tggatttgaa ctaattaata taataaatat aatatatcgt   2400

gtaaattgaa aaacgactat taacatcaat taataaataa ttttctgtta gtgaagatgg   2460

actacaagac ctaggccacc aacccccatc cacctgaatg aatgggtaac cgctaagtcc   2520

atatttcagt actccggcgt ctgcaaaaac gctttttcca caaaaatcaa attttaagtt   2580

tttactttat cctaggcaag aaaacaaaat atgcatagat tcacgttcaa attcatcaat   2640

gctcaagaaa tagcatactt gatttgaact gagatttgtc actatcctac aaattctgca   2700

cactatgaaa acgacatcaa ccaaccaaaa tccactctct ataaatacca tcacttcact   2760

agcaatttct catcaactca taacgtactc aaataaacac gctttttcag ccaac        2815
```

<210> SEQ ID NO 78
<211> LENGTH: 507
<212> TYPE: PRT
<213> ORGANISM: Sesumum alatum

<400> SEQUENCE: 78

```
Met Glu Ala Glu Met Leu Tyr Ser Ala Leu Ala Leu Thr Phe Ala Ile
  1               5                  10                  15

Ile Met Val His Arg Ile Leu Ser Asn Ser Gln Asn Lys Arg Ser Leu
             20                  25                  30

Ile Asn Leu Pro Pro Ser Pro Pro Gly Trp Leu Pro Ile Ile Gly His
         35                  40                  45

Leu His Leu Ile Lys Asn Pro Leu His Arg Thr Leu Tyr Asp Cys Ser
     50                  55                  60

Gln Lys Leu Gly Ser Ile Phe Ser Val Trp Phe Gly Ser Arg Leu Val
 65                  70                  75                  80

Val Val Val Ser Ser Ser Ser Leu Val Glu Glu Cys Phe Thr Lys Tyr
                 85                  90                  95

Asp Ile Val Leu Ala Asn Arg Pro Asp Leu His Leu Asp Leu Arg Ser
            100                 105                 110

Leu Gly Ala Ser Thr Ile Ser Val Ile Gly Ala Pro Tyr Gly Asp His
        115                 120                 125

Trp Arg Asn Leu Arg Lys Leu Cys Asp Leu Glu Val Phe Ala Pro Thr
    130                 135                 140

Arg Leu Ala Ser Phe Leu Ser Ile Arg Arg Asp Glu Arg Asp Arg Met
145                 150                 155                 160

Ile Ser Gly Leu Tyr Lys Ile Ser Ser Ala Gly Leu Ala Lys Val Asn
                165                 170                 175

Leu Glu Ala Lys Ile Ala Glu Leu Thr Phe Asn Asn Leu Met Arg Met
            180                 185                 190

Leu Ala Gly Lys Ile Tyr Tyr Gly Glu Glu Ala Glu Asp Glu Glu Glu
        195                 200                 205

Ala Lys Arg Phe Arg Asp Met Thr Lys Glu Ala Leu Glu Leu Met Asn
    210                 215                 220

Thr Phe Asn Leu Ala Glu Ile Phe Pro Ile Leu Arg Trp Ile Gly Cys
225                 230                 235                 240

Asn Gly Phe Glu Lys Gln Leu Pro Val His Ser Arg Lys Thr Asp Glu
                245                 250                 255
```

-continued

```
Ile Met Gln Gly Leu Leu Asp Glu His Arg Arg Gly Glu Arg Gln Asn
            260                 265                 270

Thr Met Val Gly His Leu Leu Ser Leu Gln Glu Ser Gln Pro Asp Tyr
        275                 280                 285

Tyr Thr Asp Glu Ile Ile Thr Gly Leu Ile Ile Ser Leu Ile Ile Ala
    290                 295                 300

Gly Thr Asp Ala Ser Val Val Thr Thr Glu Trp Ala Met Ser Leu Leu
305                 310                 315                 320

Leu Asn His Pro Lys Val Leu Glu Lys Ala Arg Gln Glu Met Asp Thr
                325                 330                 335

Leu Val Gly His Glu Arg Met Val Glu Glu Asp Asp Leu Pro Lys Leu
            340                 345                 350

Arg Tyr Leu His Tyr Ile Ile Leu Glu Thr Leu Arg Leu Phe Pro Ser
        355                 360                 365

Val Pro Thr Leu Val Pro His Glu Pro Ser Glu Asp Cys Asn Ile Gly
    370                 375                 380

Gly Tyr Asn Val Pro Lys Gly Thr Met Ile Ile Val Asn Ala Trp Ala
385                 390                 395                 400

Ile His Arg Asp Pro Lys Val Trp Asp Asp Pro Met Ser Phe Lys Pro
                405                 410                 415

Asp Arg Phe Glu Thr Leu Glu Val Glu Thr His Lys Leu Leu Pro Phe
            420                 425                 430

Gly Met Gly Arg Arg Gly Cys Pro Gly Ala Gly Leu Ala Lys Lys Phe
        435                 440                 445

Val Gly Leu Ala Leu Ala Ser Leu Ile Gln Cys Phe Asp Trp Glu Arg
    450                 455                 460

Ile Ser Ala Glu Lys Ile Asp Leu Lys Glu Gly Ala Ser Arg Ile Thr
465                 470                 475                 480

Leu Pro Lys Ala Thr Thr Leu Glu Ala Met Cys Lys Pro Arg His Val
                485                 490                 495

Met Glu Lys Val Leu Arg Gln Val Ser Asn Val
            500                 505
```

```
<210> SEQ ID NO 79
<211> LENGTH: 1524
<212> TYPE: DNA
<213> ORGANISM: Sesumum alatum

<400> SEQUENCE: 79

atggaagctg aaatgctata ttcagctctc gctctcacct tcgccataat catggttcac      60

agaattcttt caaattcaca gaacaagcgc agcctgatca atctgccgcc gagcccgcct     120

ggttggctgc cgattatcgg ccaccttcat ctcataaaaa atccactcca tagaacacta     180

tacgactgct cccagaaact gggatccata ttctccgtct ggttcgggtc ccgcctcgtg     240

gtggtggtgt cctcctcctc cctggtggag gaatgtttca ccaagtacga cattgtcttg     300

gccaaccgcc ctgacctcca tctggacctg cgatcactcg gggccagcac catcagcgta     360

atcggggccc cttacgggga ccactggcgc aacctgcgaa agttgtgcga tcttgaagta     420

ttcgccccga cccgtctcgc ctccttctta tccatcagac gagacgagag ggaccgcatg     480

atttccgggt tatacaaaat ctcgtcggcc ggtttggcga aggtgaattt ggaggcgaag     540

attgcggagc tgacgtttaa taacttaatg aggatgttgg cggggaaaat atactatggg     600

gaggaggcgg aggacgagga ggaggccaag aggttccggg acatgacgaa ggaggctttg     660

gagttgatga acaccttcaa tcttgctgag atatttccga tattgcggtg gattgggtgc     720
```

-continued

```
aatgggttcg agaagcagct gcccgttcac tcgcggaaga cggatgagat catgcaaggg    780

ctgctggacg aacaccgacg cggcgagcgc cagaacacca tggttggtca tttgctttcc    840

ttgcaggaat ctcaacctga ctactacact gatgaaatca tcactggcct cataatttca    900

ttgataatcg cggggacgga tgcatccgtt gtaactacag aatgggcgat gtctctttta    960

ctaaatcatc ccaaagtact tgaaaaggct agacaagaaa tggacacgct ggtaggacat   1020

gaacgcatgg tcgaagaaga cgatctcccc aaactacgtt accttcacta cataatcttg   1080

gagaccttaa ggttattccc ttctgttcca acgttggtgc cacacgaacc gtcggaggac   1140

tgtaatattg ggggatacaa cgtccccaag ggcacaatga tcatcgtgaa tgcatgggca   1200

atacacagag accccaaggt gtgggacgac cccatgagct ttaagcccga caggtttgag   1260

acattggagg tggagacaca caagttgttg ccatttggga tgggcaggag aggttgtccc   1320

ggagctggat tggcgaagaa gttcgtggga ttggctttgg catcgctgat ccagtgcttc   1380

gactgggaga gaattagtgc cgagaaaatt gacttgaagg aaggtgcttc taggataacc   1440

ttgcctaaag ctacgacgtt ggaagccatg tgcaaacctc gacatgtcat ggaaaaagtt   1500

cttcgtcagg tttcgaacgt ctga                                          1524
```

GENE ENCODING AN ENZYME FOR CATALYZING BIOSYNTHESIS OF LIGNAN, AND USE THEREOF

TECHNICAL FIELD

The present invention relates to enzymes for catalyzing the biosynthesis of piperitol and sesamin in sesame, and to genes encoding the enzymes. The invention also relates to use of such enzymes and genes.

BACKGROUND ART

Sesame plants, generally known as sesame (*Sesamum indicum*), belong to family *Pedaliaceae* and genus *Sesamum*. Sesame is native to central Africa and is the oldest cultivated oil plant with the history of over 6000 years. Sesame has been cultivated in various parts of the world.

Sesame seeds contain about 50% lipid and about 20% protein, in addition to various vitamins including vitamin B1, B2, and E. The main lipid component of sesame seed is triglyceride whose chief constituents are oleic acid and linoleic acid. Sesame also contains secondary metabolites generally known as sesamin, sesamolin, and lignan, which are characteristic components of the sesame plant.

Previous research has revealed various physiological activities of sesamin, which are found to be effective in improving cholesterol metabolism, and liver and immune functions (see Publication 1, for example). A separation and purification method of sesamin from the sesame seeds or wrung residues of sesame seeds has already been put to actual applications (see Patent Publications 1 and 2, for example). Sesamin is also commercially available as a medicament that enhances the liver function by promoting alcohol metabolism, etc. Other than sesamin, sesame lignans (sesaminol, sesamolin, etc.) have also been reported to have various physiological activities (see Publication 2, for example).

There has been some study on the biosynthesis of lignan (see Publication 3, for example). FIG. 1 is a schematic representation of a common biosynthesis pathway of lignan. The lignan is synthesized from a phenyl propanoid compound used as a starting material. In plants, lignan is believed to play role in the defense mechanism. As illustrated in FIG. 1, polymerization of conipheryl alcohol yields pinoresinol as the “first” lignan in the biosynthesis pathway. From pinoresinol, a wide variety of lignans are synthesized through distinct biosynthesis pathways of different plant species.

In the biosynthesis of sesamin, as shown in FIG. 1, piperitol is synthesized by the enzymatic action of a piperitol synthetase catalyzing (+)-pinoresinol, forming a methylene dioxybridge (circled in FIG. 1). Sesamin is synthesized by a sesamin synthetase forming another methylene dioxybridge in the piperitol. Experiments using membrane fractions of sesame seeds have shown that the enzymes catalyzing these reactions were two different kinds of cytochromes P450 (see Publication 4, for example).

The formation of methylene dioxybridge is often seen in the biosynthesis of alkaloid or flavonoid. For example, membrane fractions from cultured cells of *Eschscholtzia calfornica* are known to include cytochromes P450 that catalyze the biosynthesis of (S)-cheilanthifoline from (S)-scoulerine, and (S)-stylopine from (S)-cheilanthifoline, by forming a methylene dioxybridge in these compounds (see Publication 5, for example).

There have also been reported that membrane fractions from cultured cells of chickpea (*Cicer arietinum*) contain enzymes that catalyze the synthesis of Pseudobaptigenin and 5'-hydroxy Pseudobaptigenin produced by formation of a methylene dioxybridge in calycosin and pratensein, respectively. These enzymes have been identified as cytochromes P450 (see Publication 6, for example).

Others report the possibility that the deoxypodophyllotoxin 6-hydroxylase in cultured cells of *Linum flavum* may be cytochrome P450 (see Publication 7, for example).

The cytochrome P450 has also been found as an enzyme involved in the biosynthesis of berberine, which is a benzylisoquinoline alkaloid, in which (S)-tetrahydroberberine is synthesized by forming a methylene dioxybridge in (S)-tetrahydrocolimbamine. A gene that encodes this enzyme has been cloned from *Coptis japonica* (see Publication 8, for example).

The cytochromes P450 that catalyze various types of reactions as above comprise a superfamily of diverse molecular species, which are categorized based on the homology of their amino acid sequences. Different molecular species of cytochrome P450 belong to the same family if their identity is 40% or greater, and to the same sub family if their identity is 55% or greater. In the notation used in this classification, numbers denote family, and alphabets denote sub family (see Publication 9, for example). The tree diagram shown in FIG. 3 represents families and their interrelations. For example, the cytochrome P450 involved in the biosynthesis of berberine has been categorized as “CYP719.”

A single plant species include several hundred molecular species of cytochrome P450. However, as shown in FIG. 4, only a few of them have been identified based on their biochemical and physiological functions.

As a sesame-derived cytochrome P450, a gene (AY065995) that encodes p-coumarate 3-hydroxylase has been cloned, though it does not directly relate to the synthesis of sesamin or piperitol concerning the present invention.

Cloning of cytochrome P450 genes and their functional analysis have also been reported for various species of other organisms, as noted below.

For example, some of the cloned genes include:

A gene coding for petunia-derived flavonoid 3',5' hydroxylase (F3',5'H) (see Publication 10, for example);

A gene coding for flavonoid 3'-hydroxylase (F3'H: CYP75B) (see Publication 11, for example);

A gene coding for sweetroot-derived (2S)-flavanon 2-hydroxylase (F2H: CYP93B1) (see Publication 12, for example);

A gene coding for 2-hydroxy-isoflavanon synthetase (IFS: CYP93C2) (see Publication 13, for example); and A gene coding for isoflavon 2'-hydroxylase (I2'H: CYP81E1) (see Publication 14, for example).

In addition, a gene coding for flavon synthetase II (FNSII: CYP93B3) has also been cloned from *Antirrhinum majus*, using I2'H (see Publication 15, for example).

Amino acid sequences of various cytochromes P450 that belong to the CYP81 family are found in Nelson, DR, The Cytochrome P450 Homepage, Human Genomics 4, 59-65. Among different functions of these cytochromes P450, *Helianthus tuberosus*-derived CYP81B1 is known to catalyze the hydrogenation of fatty acids (see Publication 16, for example). It is also known that the enzyme I2'H belongs to CPY81E.

However, none of these cytochromes P450 is involved in the formation of methylene dioxybridge.

As a gene that encodes an enzyme involved in the biosynthesis of lignan, a gene encoding a dirigent protein involved in the synthesis of pinoresinol in *Forsythia intermedia* has been reported (see Publication 17, and Patent Publication 3, for example). There have also been reports on a gene encoding a Pinoresinol-Lariciresinol reductase in *Forsythia intermedia* (see Publication 18, and Patent Publication 3, for example), and a gene encoding a Pinoresinol-Lariciresinol reductase in *Thuja plicata* (see Publication 19, for example). In other reports, a recombinant secoiso lariciresinol dehydrogenase and its use are discussed (see Publication 20, for example).

[Patent Publication 1]

Japanese laid-open publication No. 139579/2001 (published on May 22, 2001)

[Patent Publication 2]

Japanese laid-open publication No. 7676/1998 (published on Jan. 13, 1998)

[Patent Publication 3]

Japanese PCT laid-open publication No. 507931/2001 (published on Jun. 19, 2001)

[Patent Publication 4]

Japanese PCT laid-open publication No. 512790/2002 (published on May 8, 2002)

[Publication 1]

Mitsuo, Namiki, "Sesame, science and its functions," published by Maruzen Planet

[Publication 2]

Publication of Japan Society for Bioscience, Biotechnology, and Agrochemistry, 76 805-813 2002

[Publication 3]

Lignans: bio synthesis and function, Comprehensive natural products chemistry vol. 1. 640-713, 1999

[Publication 4]

Phytochemisity, 49, 387, 1998

[Publication 5]

Phytochemisity, 30, 2953, 1991

[Publication 6]

Phytochemisity, 41, 457, 1996

[Publication 7]

Planta, 214, 288, 2001

[Publication 8]

J Biol Chem. 2003, May 5 [Epub ahead of print]

[Publication 9]

Nelson et al. Pharmacogenetics 6, 1-42, 1996

[Publication 10]

Nature 366 276-279, 1993

[Publication 11]

Plant J. 19, 441-451, 1999

[Publication 12]

FEBS Letters, 431, 287, 1998

[Publication 13]

Plant Physiology, 121, 821, 1999

[Publication 14]

Biochemical and Biophysical Research Communications, 251, 67, 1998

[Publication 15]

Plant and Cell Physiology, 40, 1182, 1999

[Publication 16]

J. Biol. Chem. 273, 7260, 1998

[Publication 17]

Plant Physiol. 123, 453, 2000

[Publication 18]

J. Biol. Chem. 271, 29473, 1996

[Publication 19]

J. Biol. Chem. 271, 618, 1999

[Publication 20]

J. Biol. Chem. 2001 Apr. 20; 276(16):12614-23, Epub 2001 Jan. 18

As described above, sesamin has a variety of physiological activities, which are known to be effective in improving various deficiencies. However, conventional sesamin production solely relied on a method using sesame seeds alone. In other words, sesamin production is completely dependent on sesame seeds. Consequently, it has been difficult to improve productivity or reduce the cost of sesamin production.

The problem can be solved effectively by genetic engineering techniques. However, to this date, no enzyme has been purified for the two kinds of cytochromes P450 that are known to be involved in the biosynthesis of sesamin in sesame seeds, and no gene for encoding these enzymes has been cloned. The situation is the same for the cytochromes P450 that form the methylene dioxybridge in different species of other organisms, or for the other kinds of cytochromes P450. There have been cloned genes encoding enzymes involved in the biosynthesis of lignan in different species of other organisms. However, none of them is involved in the synthesis of sesamin and/or piperitol.

Some of the genes derived from sesame seeds have been cloned, examples of which include AF240004, AF240005, and AF240006 encoding globulins as deposit proteins of seeds. Other examples include genes or enzymes involved in the synthesis or storage of lipids, including oleosin (J. Biochem. 122: 819-24, 1997), an acyl carrier protein desaturase (Plant Cell Physiol. 1996, 37, 201-5), Steroleosin (Plant Physiol. 2002, 128: 1200-11), and a fatty acid unsaturase (Plant Sci. 161 935-941 (2001)). However, none of these genes or enzymes is involved in the synthesis of lignan.

In other words, there has not been found a gene that encodes an enzyme involved in the synthesis of lignan. Accordingly, there is a strong need for identification of such enzymes, and genes encoding these enzymes.

The present invention was made in view of the foregoing problems, and an object of the invention is to provide a producing method of sesamin and/or piperitol with a gene encoding a sesame-derived enzyme, using, for example, recombinant organisms. The object is achieved by identifying a gene encoding an enzyme that catalyzes the formation of methylene dioxybridge between the hydroxyl group and methyl group of lignan, or more preferably a gene encoding an enzyme that catalyzes a reaction forming piperitol from pinoresinol, and/or a reaction forming sesamin from piperitol.

DISCLOSURE OF INVENTION

The inventors of the present invention diligently worked to solve the foregoing problems. In achieving the object, a group of sesame-derived cytochrome P450 genes (hereinafter "SiP genes") was obtained from a cDNA library of sesame seed, and these genes were expressed in yeasts. Microsome fractions were collected from the recombinant yeasts, and were allowed to react with pinoresinol or piperitol. The presence or absence of piperitol from pinoresinol, or sesamin from piperitol was examined by HPLC analysis after the reaction. From the result of HPLC analysis, a protein, or a gene encoding it, that catalyzes the reaction producing piperitol from pinoresinol, and sesamin from piperitol was identified.

Specifically, the present invention provides industrially useful substances and methods, as set forth in (1) through (21) below.

(1) A gene encoding a protein that catalyzes biosynthesis of piperitol and/or sesamin. (A gene encoding a protein that catalyzes the biosynthesis of piperitol from pinoresinol, and/or sesamin from piperitol.)

(2) A gene encoding a protein that catalyzes a reaction forming a methylene dioxybridge in pinoresinol and/or piperitol.

(3) A gene encoding a protein that catalyzes biosynthesis of piperitol and/or sesamin, and that consists of (a) an amino acid sequence of SEQ ID NO: 1, 64 or 78, or (b) an amino acid sequence that has been modified by substitution, deletion, insertion, and/or addition of one or more amino acids of SEQ ID NO: 1, 64 or 78.

(4) A gene encoding a protein that catalyzes biosynthesis of piperitol and/or sesamin, and that consists of an amino acid sequence which is at least 50% homologous to an amino acid sequence of SEQ ID NO: 1, 64 or 78.

(5) A gene including a base sequence of SEQ ID NO: 2, 65 or 79 as an open reading frame region.

(6) A gene encoding a protein that catalyzes biosynthesis of piperitol and/or sesamin, and hybridizing under stringent conditions with (a) a polynucleotide consisting of a base sequence of SEQ ID NO: 2, 65 or 79, (b) a polynucleotide encoding a protein consisting of an amino acid sequence of SEQ ID NO: 1, 64 or 78, or (c) a fragment of the polynucleotide (a) or (b).

(7) A gene as set forth in any one of (1) through (6), which is derived from sesame.

(8) A protein encoded by a gene as set forth in any one of (1) through (7).

(9) A protein catalyzing biosynthesis of piperitol and/or sesamin, and consisting of (a) an amino acid sequence of SEQ ID NO: 1, 64 or 78, or (b) an amino acid sequence that has been modified by substitution, deletion, insertion, and/or addition of one or more amino acids of SEQ ID NO: 1, 64 or 78.

(10) An antibody that recognizes a protein as set forth in (8) or (9).

(11) A recombinant expression vector including a gene of any one of (1) through (7).

(12) A transformant comprising a recombinant expression vector including a gene of any one of (1) through (7).

(13) A producing method of a protein, comprising the steps of:

incubating or growing a transformant of (12); and obtaining from the transformant a protein that catalyzes biosynthesis of piperitol and/or sesamin.

(14) A plant, its offspring, and a tissue of the plant and its offspring, into which a gene of any one of (1) through (7) has been introduced.

(15) A producing method of piperitol and/or sesamin, comprising the step of using a gene of any one of (1) through (7), or a protein of (8) or (9).

(16) A producing method of a transformant containing a large amount of lignan, comprising the step of using a gene of any one of (1) through (7).

(17) A producing method of a plant containing a large amount of piperitol and/or sesamin, comprising the step of using a gene of any one of (1) through (7).

(18) A producing method of a transformant containing a small amount of lignan, comprising the step of using a gene of any one of (1) through (7).

(19) A producing method of a plant containing a small amount of piperitol and/or lignan, comprising the step of using a gene of any one of (1) through (7).

(20) A method of cultivating sesame, comprising the step of using a gene of any one of (1) through (7).

(21) A gene detecting device comprising a polynucleotide probe whose base sequence is at least part of a base sequence of a gene set forth in any one of (1) through (7).

BRIEF DESCRIPTION OF DRAWINGS

FIG. 4 is a diagram showing a result of homology search with a protein encoded by SiP189 gene.

FIG. 6*a* through FIG. 6*d* are diagrams showing a result of HPLC analysis measuring activity of a protein encoded by SrSiP189 gene.

FIG. 9A through FIG. 9H are diagrams showing a result of analysis on a promoter region of SiP189 gene in search for an expression regulatory element.

FIG. 10 is a diagram showing expression regulatory elements present in the promoter region of SiP189 gene.

FIG. 12A through FIG. 12C are diagrams representing homology between SiP189 gene and SrSiPgene.

BEST MODE FOR CARRYING OUT THE INVENTION

Figure 1:
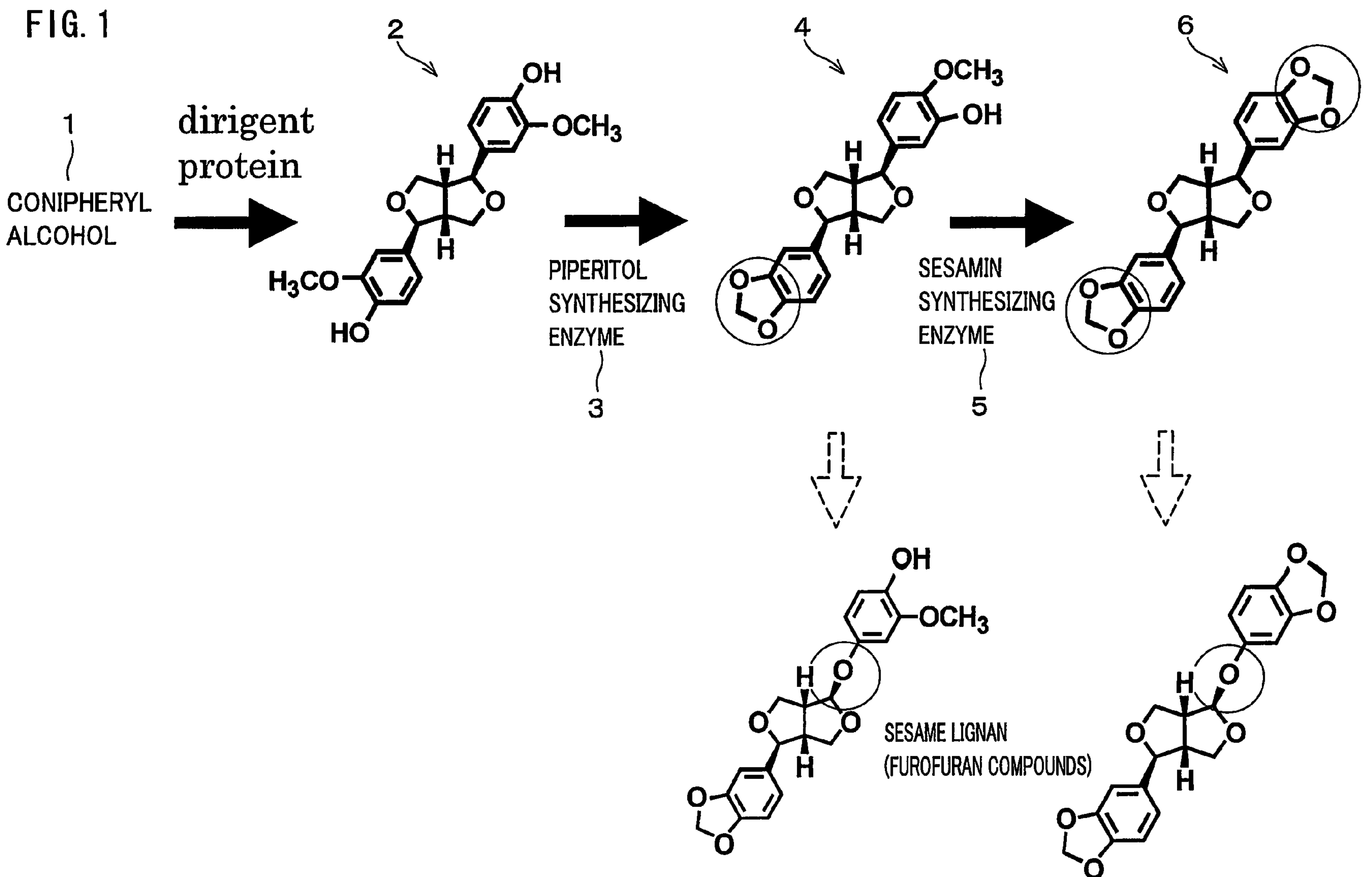
FIG. 1 is a schematic diagram showing a typical synthesis path of sesame lignan, wherein 1 is conipheryl alcohol, 2 is pinoresinol, 3 is piperitol synthetase, 4 is piperitol, 5 is sesamin synthetase, and 6 is sesamin.

The following will describe an embodiment of the present invention. It should be appreciated that the present invention is not limited in any way by the following descriptions.

(1) Genes According to the Present Invention, and Structures of Proteins Encoded by the Genes A gene according to the present invention encodes a protein for catalyzing the biosynthesis of piperitol and/or sesamin. As used herein, the "biosynthesis of piperitol and/or sesamin" means biosynthesis of piperitol from pinoresinol, and/or sesamin from piperitol. More specifically, it refers to a reaction forming a methylene dioxybridge in the pinoresinol and/or piperitol. In the embodiment, the invention will be described through gene SiP189 (with a base sequence of SEQ ID NO: 2) that encodes a seed-derived protein for catalyzing the biosynthesis of piperitol and sesamin. In the present invention, the open reading frame is the region from the start codon to the end codon, excluding the end codon.

(1-1) Genes According to the Present Invention

As used herein, the term "gene" is interchangeable with "polynucleotide", "nucleic acids", or "nucleic acid molecule". That is, the meaning of "gene" includes a polymer of nucleotides. Further, as used herein, the term "base sequence" is interchangeable with "nucleic acid sequence" or "nucleotide sequence", and it is represented by a sequence of deoxyribonucleotides (denoted by A, G, C, and T).

A gene of the present invention may code for the amino acid sequence of SEQ ID NO: 1, 64 or 78, for example. It should be noted here that proteins are generally known to retain their enzyme activities even if their amino acid sequences were modified by addition, deletion, and/or substitution of several amino acids. In this connection, a gene of the present invention, which encodes a protein that catalyzes the biosynthesis of piperitol and sesamin, may encode (a) a protein consisting of the amino acid sequence of SEQ ID NO:

1, 64 or 78, or (b) a protein consisting of the amino acid sequence modified by substitution, deletion, insertion, and/or addition of one or more amino acids of SEQ. ID NO: 1, 64 or 78 yet retains its catalytic action in the biosynthesis of piperitol and/or sesamin. For example, the present invention includes a gene having an open reading frame (ORF) with the base sequence of SEQ ID NO: 2, 65 or 79. As will be described later in Examples, a gene according to the present invention may also encode a cytochrome P450 protein.

As used herein, the "substitution, deletion, insertion, and/or addition of one or more amino acids" means the substitution, deletion, insertion, and/or addition of preferably no more than 10, more preferably no more than 7, and further preferably no more than 5 amino acids, as enabled by a conventional mutant protein producing method (e.g., site-directed mutagenesis inducing method, Hashimoto-Gotoh, Gene 152, 271-275 (1995)). Therefore, it can be said that protein (b) is encoded by a gene that encodes a mutant of protein (a). As used herein, "mutant protein" generally refers to mutant proteins that are artificially prepared by a conventional mutant protein producing method. However, the mutant protein may be isolated and purified from a natural source as well.

A gene of the present invention is not limited to double-stranded DNA, and may be the sense strand or anti-sense strand of double-stranded DNA or RNA. The anti-sense strand may be used as a probe or anti-sense medicament. For DNA, cDNA or genomic DNA obtained by cloning techniques, chemical synthesis techniques, or a combination of these different techniques may be used. Further, a gene according to the present invention may include a sequence of an untranslated region (UTR), or a vector sequence (including expression vector sequence), in addition to the sequences coding for the amino acids of proteins (a) and (b).

Further, a gene of the present invention may encode a protein that has no less than 20%, preferably no less than 50%, and more preferably no less than 60% or 70% homology to the amino acid sequence of SEQ ID NO: 1, 64 or 78, and that catalyzes the biosynthesis of piperitol and/or sesamin. The gene may be used to control a lignan level or cultivate plants. As the term is used herein, "homology" refers to a proportion of matched amino acid sequences. A higher homology means a closer relation between the amino acid sequences compared.

Further, a gene of the present invention may include a polynucleotide consisting of a base sequence of SEQ ID NO: 2, 65 or 79, a polynucleotide coding for a protein consisting of an amino acid sequence of SEQ ID NO: 1, 64 or 78, or fragments of these polynucleotides. For example, a gene of the present invention may hybridizes under stringent conditions with a polynucleotide having a base sequence coding for six or more amino acids (i.e., 18 bases), and may encode a protein that catalyzes the biosynthesis of piperitol and/or sesamin. As used herein, "under stringent conditions" means that hybridization takes place only when there is at least 80% identity, preferably at least 95% identity, and more preferably at least 97% identity. Specifically, hybridization may take place under 5×SSC at 50° C., for example.

Hybridization may be carried out by a conventional method, as described in J. Sambrook et al. Molecular Cloning, A Laboratory Manual, 2nd Ed., Cold Spring Harbor Laboratory (1989), for example. Generally, the level of stringency increases with increase in temperature and/or decrease in salt concentration (more difficult to hybridize). A suitable hybridization temperature depends on the base sequence or the length of the base sequence. For example, when a DNA fragment consisting of 18 bases coding for 6 amino acids is used, temperatures of not more than 50° C. are preferable.

The hybridization may select a gene derived from a natural source, for example, such as plants belonging to family Bryophyta. Genes derived from other natural sources may be used as well. Further, a gene selected by hybridization may be cDNA or genomic DNA.

(1-2) Proteins According to the Present Invention

A protein according to the present invention is encoded by a gene of the present invention described in (1-1) above. Encoded by a gene of the present invention, the protein catalyzes the biosynthesis of piperitol from pinoresinol, or sesamin from piperitol. The present invention also includes a protein that catalyzes the reaction forming a methylene dioxybridge in the pinoresinol or piperitol. For example, a protein of the present invention may include (a) the amino acid sequence of SEQ ID NO: 1, 64 or 78, or (b) the amino acid sequence modified by substitution, deletion, insertion, and/or addition of one or more amino acids of SEQ ID NO: 1, 64 or 78 yet retains its catalytic action in the biosynthesis of piperitol and/or sesamin.

Using a gene of the present invention described in (1-1) above, a protein according to the present invention may be obtained by introducing the gene into a host cell and expressing the gene therein. Alternatively, a protein may be obtained by isolating and purifying from cells or tissues. Further, a protein according to the present invention may be a fusion protein with other proteins. Further, a protein according to the present invention may be chemically synthesized.

It should be noted that a protein according to the present invention is not limited to polypeptides as chains of amino acids forming peptide bonds. The protein may be a complex protein of a structure other than the polypeptide, or a protein with additional polypeptides. Examples of additional polypeptides include various epitopes such as His, Myc, and Flag, tagged to a protein of the present invention.

(2) Method of Obtaining Genes and Proteins of the Present Invention

A method of obtaining (producing) a gene and protein of the present invention is not particularly limited. The following describes some representative methods.

(2-1) Method of Obtaining Genes

For genes with natural base sequences, a gene according to the present invention may be obtained by screening of cDNA libraries for example, as will be described in detail later in Examples.

Alternatively, a gene according to the present invention may be obtained with the use of amplification means such as PCR. For example, PCR may be carried out with primers designed according to the sequences at the 5' end and 3' end of a cDNA sequence (or the complementary sequences thereof) of a gene according to the present invention, using the genomic DNA (or cDNA) as a template, for example. The PCR amplifies a region of DNA flanked by the primers, thereby obtaining a large amount of DNA fragments containing a gene of the present invention.

In another method, a polynucleotide having a desired sequence is synthesized by conventional chemical synthesis procedures, based on gene sequence information.

DNA encoding an enzyme having a modified sequence of amino acid may be synthesized by PCR or ordinary site-directed mutagenesis, using DNA with a natural base sequence. For example, in order to obtain modified DNA fragments of interest, natural cDNA or genomic DNA is treated with restriction enzymes to obtain DNA fragments. Using the DNA fragment as a template, PCR or site-directed mutagenesis is carried out with primers that have been mutated to desired sequences. The mutated DNA fragments are then joined to polynucleotides (DNA) which encode an enzyme of interest and from which regions of the corresponding DNA fragments have been removed. For example, DNA that encodes an enzyme with a shorter amino acid sequence may be obtained with the use of certain restriction enzymes that cuts DNA encoding an amino acid sequence (e.g., full length amino acid sequence) longer than an amino acid sequence of interest. If the resulting DNA fragments do not encode the entire amino acid sequence of the enzyme of interest, a DNA fragment that makes up the deficient sequence may be synthesized and joined.

The resulting gene is expressed in the gene expression system of *Escherichia coli* or yeasts to obtain a protein it encodes. The enzyme activity of the protein may be evaluated to confirm whether the gene has encoded a protein that catalyzes the biosynthesis of piperitol from pinoresinol, or sesamin from piperitol. Further, with the gene introduced into a cell, the protein catalyzing the biosynthesis of piperitol from pinoresinol, or sesamin from piperitol can be obtained.

Further, with an antibody against a protein consisting of the amino acid sequence of SEQ ID NO: 1, 64 or 78, the gene encoding the enzyme for catalyzing the synthesis of piperitol and sesamin can be also cloned from other organisms.

(2-2) Method of Obtaining Proteins

A method of obtaining (producing) a protein of the present invention is not particularly limited. For example, simple purification from cells or tissues expressing the protein may be used. The cells or tissues expressing a protein of the present invention may be self-generating. For example, cells or tissues infected with a recombinant baculovirus may be used. Purification is not limited to a particular method, and may be carried out as follows. After a transformed host by an expression vector including a gene of the present invention is cultured, cultivated, or bred, a protein of interest may be collected and/or purified from the culture according to ordinary procedures, including filtration, centrifugation, cell-disruption (cell lysis), gel chromatography, and ion exchange chromatography, for example.

Another way to obtain a protein of the present invention is to use recombinant techniques. As one example, a gene according to the present invention is inserted in a carrier such as a vector, introduced into host cells by a conventional method, and expressed therein. The translated protein is purified. Specific methods of gene transfer (transformation) and gene expression will be described later.

The protein for catalyzing the synthesis of piperitol and sesamin can also be obtained with the use of an antibody against a protein consisting of the amino acid sequence of SEQ ID NO: 1, 64 or 78. Further, with the antibody, the enzyme catalyzing the biosynthesis of piperitol and sesamin, and the gene encoding the enzyme can also be cloned from other organisms.

Note that, in introducing the foreign gene into a host, various types of hosts and expression vectors can be used. Here, the expression vectors have been integrated with a promoter that functions to express the gene in the host. A type of host or expression vector used is suitably selected according to intended use. Different purification methods are available for the product proteins, depending on the type of host used and the characteristics of the protein of interest. Regardless of the type of purification method used, use of a tag or the like helps purification of the protein of interest with relative ease.

A method of preparing a mutant protein is not particularly limited either. For example, a mutant protein may be generated by introducing a point mutation in the base sequence using conventional mutant protein inducing methods, including a site-directed mutagenesis (see Hashimoto-Gotoh, Gene 152, 271-275 (1995), for example) or PCR. Alternatively, a mutant protein may be generated by a method in which mutant strains are produced by insertion of transposons. With any of these methods, the base sequence of cDNA encoding the protein (a) can be altered by substitution, deletion, insertion, and/or addition of one or more bases, so as to produce a mutant protein. For the preparation of mutant proteins, a commercially available kit may be used as well.

Other than the foregoing methods, a protein according to the present invention may be obtained by chemical synthesis using a commercially available peptide synthesizer, for example. Alternatively, a protein according to the present invention may be synthesized from a gene according to the present invention, using a cell-free protein synthesis solution as described in Proc. Natl. Acad. Sci. USA, 78, 5598-5602 (1981), J. Biol. Chem., 253, 3753-3756 (1978).

(3) Antibody According to the Present Invention

An antibody according to the present invention (polyclonal antibody or monoclonal antibody) is obtained according to a conventional method, by using a protein of the present invention described in Section (1-2) above as an antigen (for example, protein (a), (b), or fragments of these proteins). Examples of the conventional method include Harlow et al.; Antibodies: A laboratory manual (Cold Spring Harbor Laboratory, New York (1988), and Iwasaki et al.; Monoclonal antibody, hybridoma and ELIZA, Kodansha (1991). The antibody may be used in the detection and/or measurement of a protein according to the present invention.

(4) Recombinant Vectors According to the Present Invention

A recombinant expression vector according to the present invention include a gene of the present invention described in Section (1-1) above (e.g., gene encoding protein (a) or (b)). A recombinant expression vector that has incorporated cDNA is one example of a recombinant expression vector of the present invention. The recombinant expression vector may be generated using a plasmid, phage, or cosmid as non-limiting examples. Further, the recombinant expression vector may be generated by a convention method.

The type of vector is not particularly limited as long as it is expressed in a host cell. Specifically, such vectors are prepared by incorporating a gene of the present invention in a plasmid along with a promoter sequence that has been suitably selected to ensure gene expression. The promoter sequence depends on the type of host cell.

Various markers may be used to confirm whether a gene of the present invention has been introduced in a host cell, or whether the protein encoded by the gene has been successfully expressed in the host cell. The marker (e.g., a gene lacking in the host cell) is integrated with a carrier, such as a plasmid, together with a gene of the present invention, and is introduced into the host cell as an expression vector. Successful uptake of the gene of the present invention may be confirmed by checking the expression of the marker in the host cell that has incorporated the expression vector. Alternatively, a protein according to the present invention may be expressed in the form of a fusion protein in the host cell. For example, a protein according to the present invention may be expressed as a fusion protein with a green fluorescence protein (GFP) derived from *Aequorea victoria*. In this case, the GFP is used as a marker.

The host cell is not particularly limited, and various conventionally available cells may be used. Specifically, as a prokaryotic host, bacteria belonging to genus *Escherichia* (for example, *Escherichia coli*), or genus *Bacillus* (for example, *Bacillus subtilis*) may be used. As a eukaryotic host, lower eukaryotes (for example, eukaryotic bacteria including true fungi (e.g., yeasts, filamentous fungi)) may be used. Yeasts may be microorganisms that belong to genus *Saccharomyces* (for example, *Saccharomyces cerevisiae*). Examples of molds (filamentous fungi) include microorganisms that belong to genus *Aspergillus* (for example, *Aspergillus oryzae, Aspergillus niger*), or genus *Penicillum*. Further, the host cell may be an animal cell or a plant cell. The plant cell may be obtained from various plants, including those belonging to family *Pedaliaceae* or Poaceae. As for animal cells, animal cell lines obtained from mice, hamsters, monkeys, or human may be used, for example. Insect cells (for example, silkworm cell or adult silkworm itself) may be used as well.

A recombinant expression vectors according to the present invention includes expression control regions (for example, promoter, terminator, and/or origin of replication), which vary depending on the type of target host cell. For bacteria expression vectors, ordinary promoters, for example, such as trc promoter, tac promoter, or lac promoter are used. As yeast promoters, a glycelaldehyde triphosphate dehydrogenase (GAPDH) promoter, or PH05 promoter is used, for example. Amylase promoter or trpC promoter may be used as a filamentous fungi promoter, for example. For animal cell hosts, viral promoters (for example, SV40 early promoter, SV40 late promoter) are used. The expression vector may be prepared according to ordinary method, for example, using restriction enzymes and/or ligase. Transformation of hosts by the expression vector may also be carried out according to ordinary method.

A method of introducing the expression vector into the host cell (method of transformation) is not particularly limited and various conventional methods may be used, including an electroporation method, calcium phosphate method, liposome method, DEAE dextran method, and micro injection method, for example.

(5) Transformants According to the Present Invention

A transformant according to the present invention has incorporated a gene of the present invention described in Section (1-1) above (for example, a gene encoding protein (a) or (b)). As used herein, "incorporation of a gene" means transfer of a gene into a target cell (host cell) by conventional genetic engineering techniques. Further, as the term is used herein, "transformant" means not only cells, tissues, or organs, but also living organisms themselves.

A transformant according to the present invention may be prepared (produced) using a recombinant expression vector of the present invention described in Section (4) above. The organisms to be transformed are not particularly limited, and may be microbes or plants as exemplified above. With a suitable promoter or vector, animals and insects can be transformed as well.

In preferred embodyment, a sesame is used to generate a transformant according to the present invention. The method of generating a sesame transformant include a known method described in, for example, T. Asamizu: Transformation of sesame plants using MAT vector system: introduction of fatty acid desaturase genes. Sesame Newsletter 16: 22-25 (2002).

Further, as the term is used herein, "transformant" also includes plants into which genes of the present invention have been transferred, and their offspring having the same characteristics. Tissues of these plants also fall within the meaning of "transformant".

(6) Gene Detecting Device According to the Present Invention

A gene detecting device according to the present invention comprises a polynucleotide as a probe consisting of a base sequence, or its complementary sequence, which is at least a portion of a gene according to the present invention. A gene detecting device of the present invention can be used under a variety of conditions for the detection and/or measurement of expression pattern of a gene of the present invention.

One example of a gene detecting device according to the present invention is a DNA chip, in which a probe that specifically hybridizes with a gene of the present invention is immobilized on a substrate (carrier). As used herein "DNA chip" generally means a synthetic DNA chip that uses a synthetic oligonucleotide as a probe. However, it also includes an adhesion DNA microarray that uses cDNA as a probe produced by PCR, for example.

As used herein, the term "oligonucleotide" means a chain of several to several ten nucleotides joined together, and it is used interchangeably with "polynucleotide". The oligonucleotide may be generated or chemically synthesized as a fragment of a longer polynucleotide.

The base sequence of the polynucleotide used as a probe may be determined by a conventional method of specifying a characteristic sequence of cDNA sequences. (For example, a SAGE (Serial Analysis of Gene Expression) method, as described in Science 276:1268, 1997; Cell 88: 243, 1997; Science 270: 484, 1995; Nature 389: 300, 1997; U.S. Pat. No. 5,695,937 may be used.)

The DNA chip may be made by a conventional method. For example, when a synthetic oligonucleotide is used, it may be synthesized on a substrate by a combination of photolithography and solid phase DNA synthesis technique. On the other hand, when the oligonucleotide is cDNA, it is stuck on a substrate using an array device.

Further, as in common DNA chips, the accuracy of gene detection can be improved by placing a perfect-match probe (oligonucleotide) with a mismatch probe that has been prepared by substituting a single base of the perfect-match probe. Further, in order to detect different genes simultaneously, a DNA chip may be prepared in which different types of oligonucleotides are immobilized on a single substrate.

(7) Use (Effectiveness) of Genes and Proteins According to the Present Invention The foregoing descriptions mainly discussed the enzyme that catalyzes the biosynthesis of piperitol and/or sesamin in sesame. However, the present invention is not just limited to sesame-derived genes, and it also relates to use of the enzyme that catalyzes the biosynthesis of piperitol and/or sesamin. The enzyme for catalyzing the biosynthesis of piperitol and/or sesamin may be derived from plants, animals, or microorganisms. Regardless of where the enzyme derives from, the enzyme can be used to control lignan level as long as it has the enzyme activity in the biosynthesis of piperitol and/or sesamin. Further, the invention concerns plants with a controlled lignan level, and their offspring and tissues, obtained by transferring a gene that encodes an enzyme for catalyzing the biosynthesis of piperitol and/or sesamin. The plant may be in the form of cut flowers. A gene of the present invention that encodes an enzyme for catalyzing the biosynthesis of piperitol and/or sesamin can be used to generate piperitol or sesamin, or suppress formation of piperitol or sesamin. With the current technology, it is perfectly possible to transfer the gene in plants and express it constitutively or tissue-specifically. It is also possible to suppress expression of a gene of interest using an anti-sense method, co-suppression method, RNAi method, or the like. Non limiting examples of plants that can be transformed include: sesame, rice, *Forsythia suspenta*, tabaco, *Arabidopsis thaliana*, bird's-foot trefoil, barley, wheat, rapeseed, potatoes, tomatoes, poplar, bananas, eucalyptus, sweet potatoes, soy, alfalfa, lupin, corns, cauliflower, roses, chrysanthemum, carnation, *Antirrhinum majus*, cyclamen, orchid, *Eustome russellianum*, freesia, gerbera, gladiolus, Baby's Breath (*Grypsophila elegans*), kalanchoe, lily, pelargonium graveolen, geranium, petunia, torenia, tulips, and the like.

The present invention provides a protein producing method including the step of incubating or breeding a transformant described in Section (5) above, and the step of obtaining from the transformant a protein that catalyzes the biosynthesis of piperitol and/or sesamin. The method allows for easy and mass production of the protein that catalyzes the biosynthesis of piperitol and/or sesamin. The method only requires the foregoing steps, and other conditions are not particularly limited and may be suitably set (for example, type of host, materials used, and settings).

A gene and protein according to the present invention may be used in a producing method of piperitol and/or sesamin in which piperitol and/or sesamin are biosynthesized. The method allows for easy and mass production of piperitol and/or sesamin, and therefore may be used in manufacture of food (health food in particular) and pharmaceuticals containing piperitol and/or sesamin. Note that, as used herein "using a gene or protein" means use of a gene or protein under various conditions, including in vivo, in vitro, and ex vivo. In one example of a producing method of piperitol and/or sesamin, a gene is transferred into a plant cell, and piperitol and/or sesamin are biosynthesized in the transformant plant in vivo. In another example, a protein of the present invention is allowed to react with a precursor of piperitol or sesamin ex vivo for the biosynthesis of piperitol and/or sesamin. Further, piperitol and/or sesamin may be produced using a bioreactor, for example. It should be noted here that the gene itself does not possess the enzyme activity for the biosynthesis. It is therefore preferable that the gene be used in the form of a protein it encodes.

The present invention also provides a producing method of a transformant with a high lignan content or low lignan content, using genes of the present invention. The method can be used to produce a transformant with a controlled lignan level, both easily and conveniently. The lignan may be extracted, or the transformant itself may be used as a food or pharmaceutical, or as a precursor of these products.

As used herein, "plants with a high piperitol and/or sesamin content" means plants containing a large amount of piperitol and/or sesamin. As used herein, "plants with a low piperitol and/or sesamin content" means plants containing a small amount of piperitol and/or sesamin.

A gene according to the present invention may be used in a method of cultivating sesame. For example, the method can be used to transfer a gene of the present invention into sesame and cultivate sesame containing a large amount of piperitol and/or sesamin. The transformant sesame produces seeds that contain lipids with a high piperitol and/or sesamin level, which can then be collected.

While the invention is susceptible to various modifications and alternative forms, a specific embodiment thereof will be described below in more detail by way of Examples with reference to the attached drawings. It should be understood, however, that it is not intended to limit the invention to the particular forms disclosed, but on the contrary, the invention is to cover all modifications, equivalents, and alternatives falling within the scope of the invention as defined in the appended claims.

EXAMPLES

The invention is now described in detail based on the following Examples. Unless otherwise noted, the molecular biological techniques used in these Examples are based on Molecular Cloning (Sambrook et al.).

Example 1

Preparation of lignan from *Forsythia intermedia*

Sixty grams of dried *Forsythia intermedia* leaves was boiled in 3 L water for 30 minutes, and the extract was filtered with a filter (circle; 300 mm; Tokyo roshi Kaisha). After reducing the solvent volume of a filtrate dispensed with an evaporator, the sample was freeze-dried (30/N), and an extracted freeze-dried sample was obtained (21.6837 g).

Seven grams of the extracted freeze-dried sample was re-dissolved in 100 ml water and was homogenized by ultrasonic wave. Then, a column filled with 400 ml Diaion HP-20 resin (Mitsubishi Chemical Corporation) was washed with 800 ml of 50% acetone and equilibrated with 2 L water. Using the column, the homogenized sample was crudely purified. Specifically, after loaded with the sample, the column was washed with 800 ml water, followed by first elution with 800 ml of 50% methanol, and second elution with 800 ml of 100% methanol.

Each sample obtained from the first elution and second elution was analyzed by HPLC under the following conditions to determine the presence or absence of lignan. For the mobile phase, solution A (0.1% trifluoroacetic acid (TFA)) and solution B (0.1% TFA, 90% acetonitrile) were used. For the column, Develosil C30-UG-5 (Nomura Chemical Co., Ltd., 4.6 mm×150 mm) was used. After equilibrating the column with a mixture containing 60% solution A and 40% solution B (20 minutes), the sample was eluted for 15 minutes at a flow rate of 0.6 ml/minute through a linear gradient of 60% solution A and 40% solution B to 10% solution A and 90% solution B. The sample was further eluted for another 10 minutes with 10% solution A and 90% solution B. Proteins were detected at an absorption wavelength of 287 nm and were fractionated every minute (crude fractionation analysis). Using the SPD-10AV (Shimazu Corporation), each fraction was measured in a spectral range of 220 nm to 400 nm to search for a substance with two absorption maxima, which are characteristic absorption patterns of lignan (230 nm and 280 nm). The result of measurement showed that a substance with the characteristic absorption maxima of lignan was contained mainly in the second elute.

To separate lignan, fractionation was carried out under the following conditions (main fractionation). The second elute was concentrated with an evaporator, and was freeze-dried (dry weight 1.0325 g). One gram of the extracted freeze-dried sample was dissolved first in 1 ml dimethyl sulfoxide (DMSO), and then in 6 ml of 30% solution B, using sonication both times. The elute was separated by centrifugation at 15000 rpm, and about 6 ml of the supernatant was loaded onto a column (Develosil ODS-UG-15/30; C-18 (Nomura Chemical Co., Ltd., 50 mm×500 mm)). For the mobile phase, solution A (0.05% TFA) and solution B (0.05% TFA, 90% acetonitrile) were used. After equilibrating the column for 20 minutes at a flow rate of 32 ml/minute with 70% solution A and 30% solution B, the sample was loaded onto the column and was eluted for 60 minutes with a linear gradient of 70% solution A and 30% solution B to 10% solution A and 90% solution B. The sample was further eluted for 30 minutes with 10% solution A and 90% solution B. Detection was made at an absorption wavelength of 280 nm, and the elute was fractionated every minute (32 ml) (detector: 115UV detector, the Gilson product). At the end of the procedure, eight fractions with an absorption peak at 280 nm were obtained. These fractions were concentrated with an evaporator, and were freeze-dried. Each fraction was analyzed by HPLC under the same conditions as in the crude fractionation analysis. Among these fractions with the characteristic spectrum of lignan, fractions believed to be pure lignan were analyzed by $^1H$ NMR analysis so as to identify pinoresinol. As a result, 49.7 mg of pinoresinol was obtained.

Example 2

Lignan Analysis in Sesame Seeds

Immature sesame seeds were collected out of the sheath of cultivated sesame, and were freeze-dried to extract lignans with acetone. The following describes a preparation method of acetone extract.

About 100 mg of freeze-dried sample of crushed sesame seeds was dissolved in 1 ml of acetone to obtain an acetone extract. 100 μl of acetone extract was dried and re-dissolved in 20 μl DMSO, followed by addition of 80 μl of 50% acetonitrile containing 0.1% TFA. The solution was filtered with the Millex-LH filter (Millipore Corporation, 0.45 μm/4 mm) to prepare a sample for HPLC analysis. The result of HPLC analysis confirmed the presence of lignans, with their retention times matching the retention times of piperitol (a standard sesame lignan (control)) (retention time of about 12 minutes), sesamin (retention time of about 16 minutes), and sesamolin (retention time of about 18 minutes).

The sesame seeds were divided into four stages according to their growth stages.

Stage 1: Seed sheath no longer than 1.5 cm

Stage 2: Seed sheath between 1.5 cm and 2 cm

Stage 3: Seed sheath 2 cm or greater, yellowish green sheath

Stage 4: Seed sheath 2 cm or greater, dark green sheath

The result of HPLC analysis under these conditions confirmed accumulation of piperitol, sesamin, and sesamolin in Stage 3 and Stage 4.

That is, the result indicates the presence of an enzyme, and a gene encoding it, involved in the production of piperitol and sesamin in the sesame used in this Example.

Example 3

Preparation of Sesame cDNA library

From the sesame seeds used in Example 2, total RNA was extracted with the RNeasy Plant Mini Kit (QIAGEN) according to the method recommended by the manufacturer. From the extracted RNA, 5 μg of poly A(+) RNA was obtained using the oligotex-MAG mRNA purification kit (TaKaRa). Using the poly A(+) RNA as a template, cDNA library was constructed with the ZAP Express cDNA Synthesis Kit and ZAP Express cDNA Gigapack3 Gold Cloning Kit (Stratagene) according to the method recommended by the manufacturer. The cDNA library was obtained in $1\times10^7$ pfu/ml.

Example 4

Cloning of Sesame-Derived Lignan Biosynthetic Gene

About 300,000 pfu of cDNA library were screened. As probes, the sequences of cytochrome P450 gene of *Arabidopsis thaliana* of a known genome sequence were used.

Specifically, a superfamily of cytochrome P450 genes of *Arabidopsis thaliana* was phylogenetically classified based on the primary sequences (see FIG. 3), and 13 kinds of *Arabidopsis thaliana* cytochrome P450 genes (CYP90A, CYP72B, CYP71B, CYP84A, CYP96A, CYP710A, CYP86A, CYP74, CYP75B, CYP79F, CYP81D, CYP705A, and CYP83A) were used as probes for screening the sesame seed library. The DNA was amplified with primers of SEQ ID NOs: 5 to 30 to introduce DIG-label into the probes. The PCR was carried out as follows. After extracting total RNA from *Arabidopsis thaliana* with the RNeasy Plant Mini Kit (QIAGEN), cDNA was obtained by reverse transcription using 1 μg of total RNA as a template. The synthesis of cDNA was carried out with the Superscript™ First-Strand Synthesis System for RT-PCR (Invitrogen) under the conditions recommended by the manufacturer. The reaction mixture of PCR (50 μl) contained 1 μl of the *Arabidopsis* genomic DNA, 1×Taq buffer (TaKaRa), 0.2 mM dNTPs, primers (SEQ ID NOs: 5 to 30, 0.4 μmol/μl each), and 2.5 U rTaq polymerase. The reaction was carried out at 94° C. for 5 minutes, and then in 28 cycles at 94° C. for 1 minute, at 53° C. for 1 minute, and at 72° C. for 2 minutes. The probes were DIG-labeled under the same PCR condition. Screening and the detection of positive clones were carried out with the DIG-DNA labeling & detection kit (Roche).

The detection of positive clones was carried out under reduced stringent hybridization conditions, based mainly on the method recommended by the manufacturer. Specifically, after 2-hour pre-hybridization of membrane at 37° C. using a hybridization buffer containing 5×SSC, 30% formaldehyde, 50 mM sodium phosphate buffer (pH 7.0), 1% SDS, 2% blocking reagent (Roche), 0.1% lauroyl sarcosine, and 80 μg/ml sperm DNA of salmon, DIG-labeled mix probes were added in the buffer and the membrane was incubated overnight. The membrane was washed at 58° C. for 1 hour in a 5×SSC washing solution containing 1% SDS.

After the second screening, 96 independent positive clones were obtained. The 96 clones were inserted in the pBK-CMV plasmid (Stratagene) according to the method recommended by the manufacturer, and the nucleotide sequences at the 5' end and 3' end of the insert region were determined with M13RV primer and M13M4(−20) primer, respectively. As a result, 46 clones had sequences similar to the sequences of the cytochrome P450. The entire nucleotide sequence of the insert region was determined. The resulting clones were classified into 5 independent P450 homologs (Sesamum indicum P450; SiP) SiP168, SiP189, SiP236, SiP249, and SiP288. Thereafter, RT-PCR was carried out using primers (SEQ ID NOs: 31 to 40) specific to these five SiP genes. As a template, cDNA obtained by reverse transcription of RNA prepared from the leaves and seeds of sesame was used. The result showed that the five SiP genes were expressed in the seeds. The reaction mixture of PCR (25 μl) used in RT-PCR contained 1 μl of each cDNA, 1×Ex-Taq buffer (TaKaRa), 0.2 mM dNTPs, primers (0.2 μmol/μl each), and 1.25 U Ex-Taq polymerase. The reaction was carried out at 94° C. for 3 minutes, and then in 26 cycles at 94° C. for 1 minute, at 53° C. for 1 minute, and at 72° C. for 2 minutes. Ribosomal 18SRNA (AJ236041) was used as a sesame internal control gene to compare expression levels. Primers of SEQ ID NOs: 3 and 4 were used for amplification.

Example 5

Generation of Transformants Including Expression Vector for the Sip Gene

Among the 5 SiP genes, SiP249 (pSPB2031) and SiP288 (pSPB2034) were believed to encode the full open reading frame (SEQ ID NOs: 53 to 56). A 1.8 kb cDNA fragment containing the SiP249 ORF obtained by digesting pSPB2031 with BamHI and XhoI was inserted at the BamHI and SalI sites of the yeast expression vector pYE22m (Holton, T. A et al., Nature 366, 276-279, 1993). As a result, pSPB2046 was obtained. The multiple cloning site of the yeast expression vector pYE22m is flanked by the glyceraldehydes-3-phosphate dehydrogenase gene (GAPDH) promoter and the GAPDH terminator, and the insert inserted in the multiple cloning site is constitutively expressed in yeasts under the regulation of the GAPDH promoter. The selection marker for the vector is tryptophan. Meanwhile, a 1.8 kb cDNA fragment containing the SiP288 obtained by digesting pSPB2034 with BamHI and XhoI was inserted at the BamHI and SalI sites of the yeast expression vector pYE22m. As a result, pSPB2047 was obtained. The two kinds of yeast expression vector were used to transform the yeast INVsc strain (Invitrogen) according to ordinary method, so as to obtain INVsc/pYE22m/SiP249 and INVsc/pYE22m/SiP288.

The genes of SiP168, SiP189, and SiP236 had incomplete open reading frames. In order to obtain sequences with complete open reading frames (SEQ ID NOs: 1 and 2, and 57 to 60), the 5' end of each gene was amplified with the GeneRacer kit (Invitrogen) according to the method recommended by the manufacturer. Primers of SEQ ID NOs: 41 to 46 were used for amplification. The sequences amplified the 5' end of each SiP gene were determined.

In order to amplify the full length open reading frames of these 3 kinds of SiP genes, the genes were amplified by PCR. As a template, cDNA derived from sesame seeds was used. The primers used the PCR had restriction enzyme sites as noted below. The PCR was carried out as follows. The reaction mixture of PCR (50 µl) contained 1 µl of template cDNA derived from sesame seed, 1×KOD plus buffer (TOYOBO), 0.2 mM dNTPs, primers (SEQ ID NOs: 47 to 52, 0.4 pmol/µl each), 1 mM $MgSO_4$, and 1 U KOD plus DNA polymerase. The reaction was carried out at 94° C. for 5 minutes, and then in 30 cycles at 94° C. for 1 minute, at 55° C. for 1 minute, and at 72° C. for 2 minutes. The amplified fragment containing the full length SiP was inserted in the multiple cloning site of the pCR-blunt II TOPO vector (Invitrogen), so as to obtain TOPO-SiP168 (pSPB2064), TOPO-SiP189 (pSPB2055), and TOPO-SiP236 (pSPB2048).

A DNA fragment containing cDNA of about 1.5 kb obtained by digesting the restriction enzyme sites of the primers used in the amplification of pSPB2064, pSPB2055, and pSPB2048 was inserted at the BamHI and SalI sites of the yeast expression vector pYE22m. As a result, pYE22m/SiP168 (pSPB2052), pYE22m/SiP189 (pSPB2053), and pYE22m/SiP236 (pSPB2049) were obtained.

The three kinds of yeast expression vectors were used to transform the yeast INVsc strain (Invitrogen), so as to obtain INVsc/pYE22m/SiP168, INVsc/pYE22m/SiP189, and INVsc/pYE22m/SiP236.

Example 6

Biosynthesis of Sesame Lignan in the Transformants

In addition to the INVsc/pYE22m/SiP249 and INVsc/pYE22m/SiP288, the three transformants INVsc/pYE22m/SiP168, INVsc/pYE22m/SiP189, and INVsc/pYE22m/SiP236 were incubated at 30° C. for 36 hours in a 400 mL YNBDglc medium (0.67% yeast nitrogen base, 2% glucose, and 20 mg/L of various amino acids excluding tryptophan). From the culture solutions of the yeast transformants, microsome fractions were collected by a known ultracentrifugation method (Holton, T. A et al., Nature 366, 276-279, 1993).

The microsome sediments were suspended in 1 ml of suspension buffer (0.1M potassium phosphate buffer (pH 7.4), 20% glycerol, 0.3 µl/ml mercaptoethanol) to obtain a microsome solution. To 240 µl of the microsome solution was added 30 µl of 1M potassium phosphate buffer (pH 7.4), 6 µl of 50 mM NADPH, and 24 µl of 267 µM pinoresinol or piperitol. The mixture was reacted at 30° C. for 1 hour. To the reaction mixture of enzyme, an equal amount of 100% acetonitrile containing 0.1% TFA was added (50% final concentration). The mixture was centrifuged at 15000 rpm at 4° C. for 3 minutes, and 150 µl of supernatant was purified with a Millex-LH filter (Millipore Corporation, 0.45 µm/4 mm). The purified sample was then analyzed by HPLC under the same conditions as in the crude fractionation analysis described in Example 1.

The result of HPLC analysis for INVsc/pYE22m/SiP189 is described below with reference to FIG. 2(*a*) through FIG. 2(*e*). In the INVsc/pYE22m/SiP189, the pinoresinol (FIG. 2(*a*), retention time of about 8 minutes) converted into two products with a lignan-like absorption spectrum with retention times of about 12 minutes and about 16 minutes, respectively (FIG. 2(*b*)). Further, in the INVsc/pYE22m/SiP189, the piperitol (FIG. 2(*d*), retention time of about 12 minutes) was converted into a product with a lignan-like absorption spectrum with a retention time of about 16 minutes (FIG. 2(*e*)). From these retention times, they were considered to be piperitol (retention time of about 12 minutes) and sesamin (retention time of about 16 minutes), respectively.

By the LC-MS/MS analysis (LC: Waters 2790, the Waters product; MS: QUATRO micro, the Micromass product), the two peaks (retention times of about 12 minutes and 16 minutes) were compared with a standard based on their molecular weights and fragment patterns. The result showed that their molecular weights matched that of the standard, thereby identifying the two SiP189 products as piperitol and sesamin. The LC-MS/MS analysis was carried out under the following conditions. For LC, the Develosil C30-UG-5 (Nomura Chemical Co., Ltd., 2.0×50 mm) was used. As the mobile phase, solution A ($H_2O$), solution B (methanol), and solution C (10 mM $CH_3COONH_4$) were used. The flow rate was 0.25 ml/min with 10% solution C. Under these conditions, piperitol and sesamin were detected after 8.4 minutes and 10.1 minutes. MS was carried out in a POSITIVE measurement mode. It was found as a result that SiP189 encodes an enzyme that synthesizes sesamin from pinoresinol via piperitol. Initially, it was believed that different enzymes were involved in the synthesis of piperitol from pinoresinol, and the synthesis of sesamin from piperitol. The present invention proved the contrary, showing that a single enzyme encoded by a gene of the present invention is involved in the both reactions.

Figure 2:
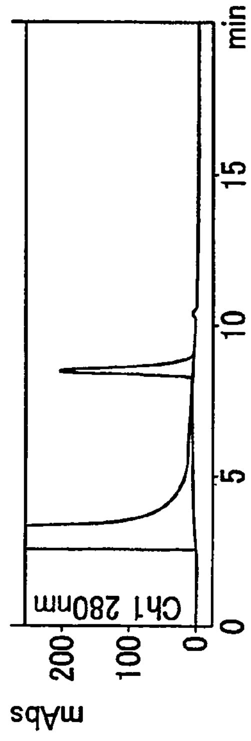
FIG. 2*a* through FIG. 2*f* are diagrams showing results of HPLC measuring activity of an enzyme encoded by SiP189 gene.
Figure 2:
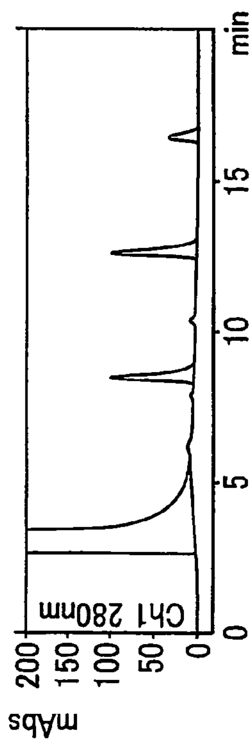
Figure 2:
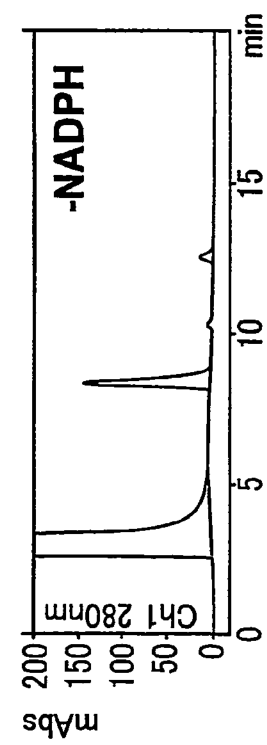
Figure 2:
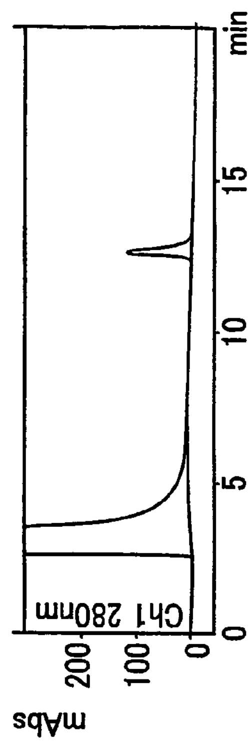
Figure 2:
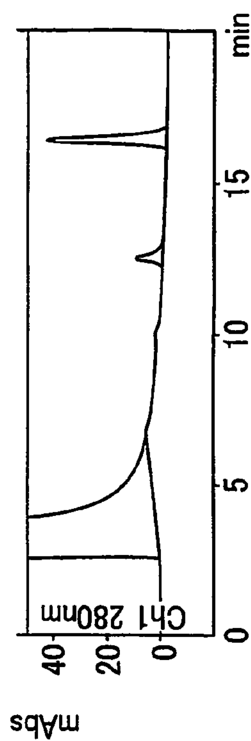
Figure 2:
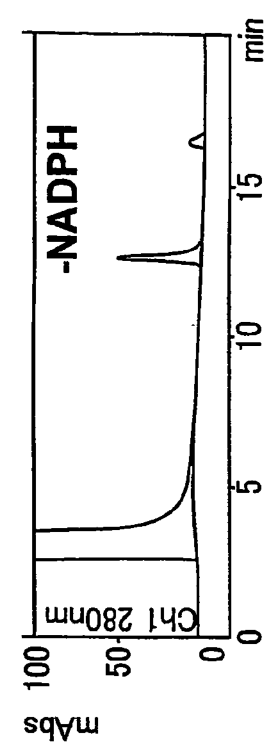

From the result of analysis using the reaction system that did not contain NADPH in the reaction mixture of enzyme, it was found that the activity of INVsc/pYE22m/SiP189 to produce piperitol was dependent on NADPH (FIGS. 2(*b*) and 2(C)). The same was the case for sesamin (FIGS. 2(*e*) and 2(*f*)). In the absence of NADPH, the activities for producing piperitol and sesamin dropped to about 14% and about 18%, respectively, from the levels in the presence of NADPH.

Thereafter, the microsome fraction of the INVsc/pYE22m/SiP189 was reduced by CO, and its absorption spectrum was measured with a spectrophotometer (the Hitachi product U-3000P Spectrophotometer). The result showed that the microsome fraction had absorption at 450 nm, compared with the transformant yeast INVsc/pYE22m used as a control. The result therefore confirmed production of cytochrome P450 protein in the microsome fraction of the INVsc/pYE22m/SiP189.

According to the method described in Example 2, RNA was extracted from the sesame seeds separated into 4 stages according to their growth in Example 2. RT-PCR was carried out using a primer set (SEQ ID NOs: 49 and 50) for amplifying SiP189, and a primer set (SEQ ID NOs: 3 and 4) for amplifying Si18SrRNA. The reaction mixture of PCR (25 μl) contained 1 μl of each cDNA, 1×Ex-Taq buffer (TaKaRa), 0.2 mM dNTPs, primers (0.2 pmol/μl each), and 1.25 U Ex-Taq polymerase. The reaction was carried out at 94° C. for 5 minutes, and then in 2-6 cycles at 94° C. for 1 minute, at 53° C. for 1 minute, and at 72° C. for 2 minutes. The result confirmed strong expression of SiP189 in Stage 4, in which accumulation of sesamin in the seed becomes notable. From the fact that the growth-stage dependent lignan accumulation coincides with the time of SiP189 gene expression, the SiP189 gene was found to encode the enzyme for producing piperitol and sesamin in the sesame seeds.

Figure 3:
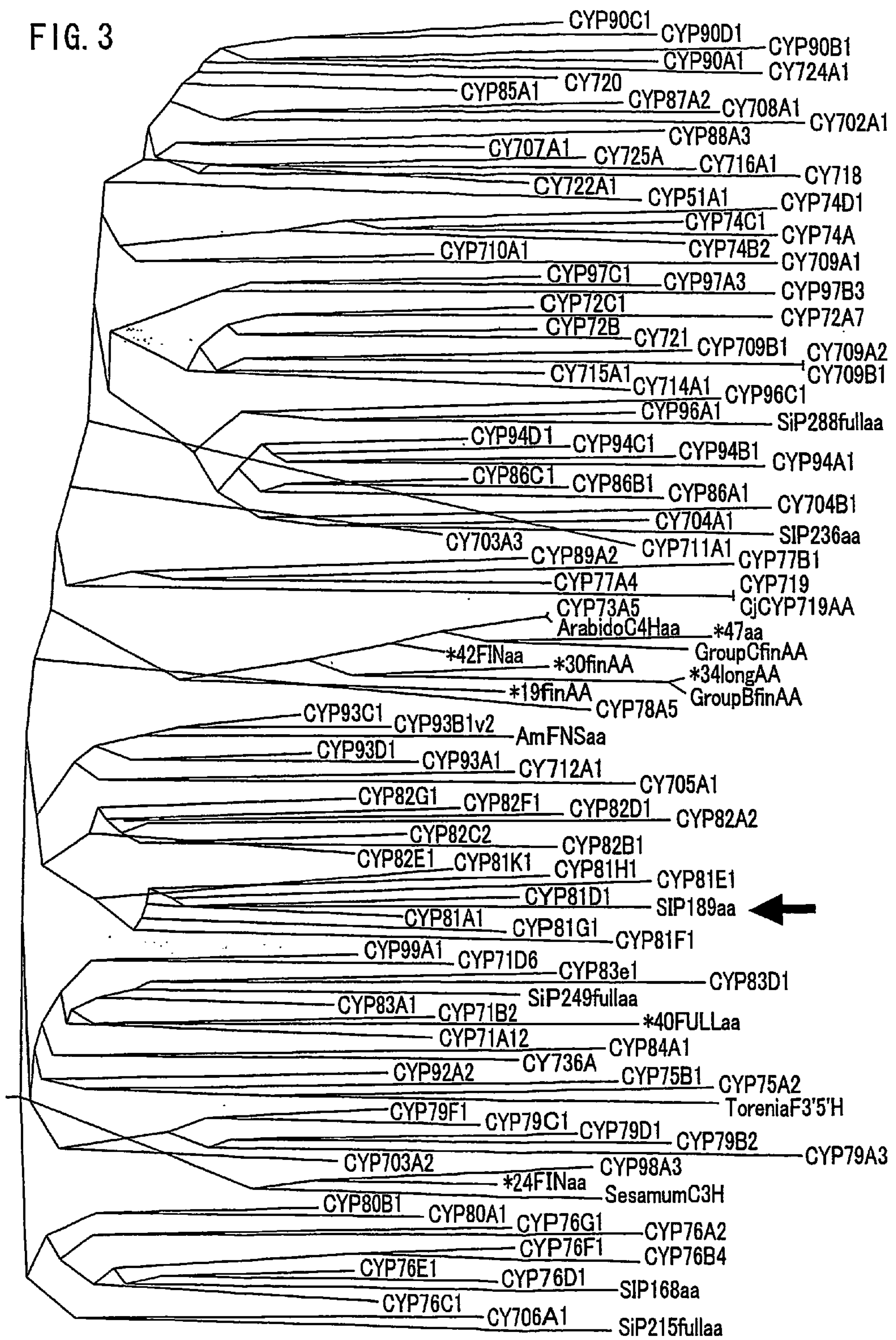
FIG. 3 is a tree diagram obtained from the analysis of the primary structure of amino acids encoded by cytochrome P450.

The foregoing results show that the SiP189 gene encodes cytochrome P450 that catalyzes the reaction producing piperitol from pinoresinol, and the reaction producing sesamin from piperitol. In FIG. 3, SiP189 is indicated by arrow. It can be seen from FIG. 3 that SiP189 belongs to the CYP81 family in the cytochrome P450 superfamily.

The gene enables synthesis of sesamin and piperitol using various organisms including sesame and other plants, or a system such as a bioreactor.

Example 7

Genomic Analysis of SiP189 Gene in Cultivated Sesame *Sesamum indicum*

In order to find the number of copies of SiP189 gene in the *S. indicum* genome, a genomic Southern analysis was carried out.

Using the Nucleon Phytopure for Plant Extraction Kit (Amersham), genomic DNA was extracted from the leaves of *S. indicum* (cultivar Masekin) according to the method recommended by the manufacturer. Ten micrograms of the genomic DNA so extracted was completely digested by three kinds of restriction enzymes EcoRI, NcoI, and XbaI, and each sample was separated by electrophoresis on an agarose gel. The agarose gel was hydrolyzed for 15 minutes using 0.25 M HCl, denatured for 30 minutes using a solution containing 1.5 M NaCl and 0.5 M NaOH, and neutralized with a solution containing 1.5 M NaCl and Tris-HCl (pH 7.5). The genomic DNA was then transferred onto a membrane (Hybribond-N, Amersham) in 20×SSC, and was bound to the membrane by irradiation of ultraviolet light. The membrane was subjected to pre-hybridization at 42° C. for 1 hour in a hybridization buffer (high SDS buffer) containing 7% SDS, 50% formamide, 5×SSC, 2% blocking reagent, 0.1% lauroyl sarcosine, and 50 mM sodium phosphate buffer (pH 7.0).

As a hybridization probe, an ORF region of about 900 bp starting from a start methionine of the cDNA of the SiP189 was used. This region of the cDNA was DIG-labeled by PCR, using primers of SEQ ID NO: 61 (Bam-SST-FW2) and SEQ ID NO: 62 (SiP189-Nco-RV). The reaction mixture of PCR contained 1 ng of plasmid (pSPB2055) containing the cDNA of SiP189, 1×PCR buffer, 1×DIG-dNTP mixture (PCR DIG Labeling Mix, Roche), 0.2 pmol/μl of each primer, and 1U rTaq polymerase (TAKARA BIO INC.). The PCR was carried out in 30 cycles at 95° C. for 30 seconds, at 53° C. for 30 seconds, and at 72° C. for 1 minute.

The PCR product was purified with the Sephadex G-50 quick spin column (Boehringer), and was heat denatured and immediately placed on ice. As a hybridization probe, 10 μl of the denatured product was added to a prehybridization solution, and the mixture was incubated overnight at 42° C.

The membrane was washed twice at 65° C. for 30 minutes in a 0.2×SSC solution containing 0.1% SDS (high stringent hybridization condition). Hybridization signals were obtained with the DIG-labeling & detection kit (Roche) according to the DIG application manual (Roche).

Figure 5:
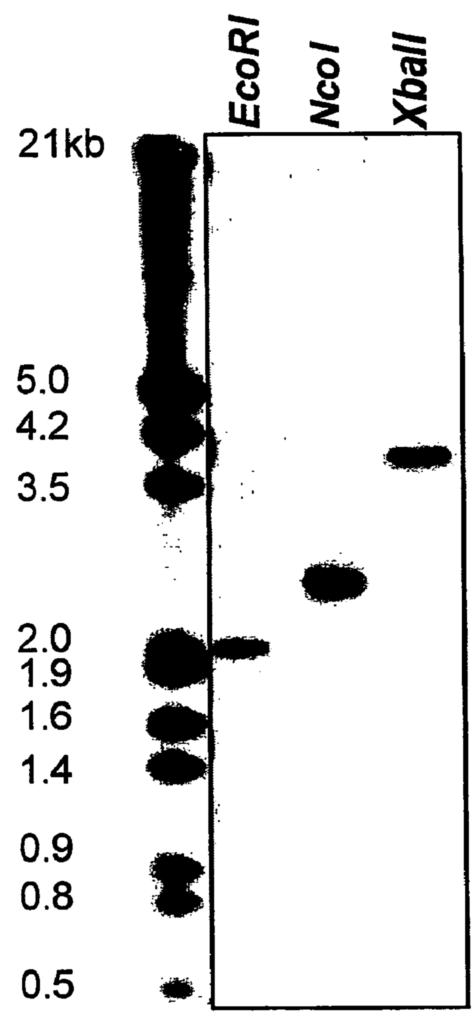
FIG. 5 is a diagram showing a result of Southern analysis on SiP189 gene.

FIG. 5 shows the result of detection. As shown in FIG. 5, the SiP189 gene was detected as a single band for all of the three restriction enzyme treatments. The result indicates that the SiP189 gene exists as a single gene in the *S. indicum* genome, and that no other genes in the genome have strong homology to the SiP189 gene. Therefore, it can be said that the catalytic activity for synthesizing piperitol and sesamin in sesame plants is conferred by the SiP189 gene.

Example 8

Isolation of SiP189-Like Gene from *Sesamum radiatum*

*Sesamum radiatum* is a sesame plant found in Africa. A cytogenetic analysis has revealed that the number of chromosomes in this particular species of sesame plant was 2n=64, indicating a cytogenetically different lineage from the *S. indicum* (2n=26) (Mitsuo Namiki, Teisaku Kobayashi, Science of sesame, Asakura Shoten). A lignan content has also been analyzed in the seeds of *S. radiatum*, and accumulation of sesamin has been reported (Bedigian, D., et al. Biochemical Systematics and Ecology 13, 133-139, 1985). This suggests that *S. radiatum* should have a gene (SrSiP189) encoding an enzyme corresponding to the SiP189 of *S. indicum*. In addition, it is expected that the sequence of the SrSiP189 gene of the *S. radiatum* is highly homologous to the sequence of SiP189.

According to the procedure of Example 4, cDNA was prepared from the seeds of *S. radiatum*. Using 1 μl of the cDNA as a template, RT-PCR was carried out according to the method of Example 4, using primers of SEQ ID No: 61 (Bam-SST-FW2) and SEQ ID NO: 63 (GR-SST-RV1). The primers were designed according to the sequence of SiP189, so as to amplify fragments probably containing a full length ORF. The RT-PCR produced a fragment of about 1.5 kb, which was believed to contain SrSiP189. The fragment was inserted in the pCR-blunt II TOPO vector (Invitrogen), and pSPB2068 was obtained. The entire nucleotide sequence of the inserted fragment was determined. The result showed 96% sequence homology on the DNA level, and 95% sequence homology on the amino acid level, as compared with SiP189 derived from *S. indicum* (SEQ ID NO: 64 shows the amino acid sequence of SrSiP189, and SEQ ID NO: 65 shows the nucleotide sequence of SrSiP189). According to the procedure of Example 4, RT-PCR was carried out using the primers (SEQ ID NOs: 61 and 63). As a template, cDNA prepared from the seeds and leaves of *S. radiatum* was used. The result found strong SrSiP189 expression in seeds but hardly any in leaves. The analysis of SrSiP189 expression by RT-PCR therefore indicated that SrSiP189 was functional in seeds.

Example 9

Functional Analysis of SrSiP189 Gene in *Sesamum radiatum*

In order to determine the biochemical function of SrSiP189, a recombinant SrSiP189 protein was expressed in yeasts, and the activity of the recombinant SrSiP189 protein for the biosynthesis of lignan was examined. First, pSPB2068 was digested with restriction enzymes BamHI and XhoI, and a resulting fragment of about 1.5 bp containing cDNA with a full length SrSiP189 was inserted at the BamHI site and SalI site of a yeast expression vector pYE22m. As a result, pSPB2069 was obtained. According to the procedure of Example 6, a microsome was prepared from the yeast transformants, and biosynthesis activities for lignan were measured. FIG. 6 shows a result of HPLC analysis. As shown in FIG. 6, The recombinant SrSiP189 protein had a NADPH dependent catalytic activity for converting pinoresinol into piperitol, and piperitol into sesamin, as with the SiP189 derived from *S. indicum* (FIG. 6(*a*) and FIG. 6(*b*)). In an enzyme reaction mixture containing no NADPH, the catalytic activities for piperitol and sesamin dropped to 16.9% and 8.4%, respectively (FIG. 6(*c*) and FIG. 6(*d*)). The result therefore showed that the SrSiP189 was indeed a counterpart gene of the SiP189 in *S. indicum*.

The foregoing result confirmed that a gene with an SiP189-like sequence is found across species, and that the gene encodes an enzyme that catalyzes the reaction converting pinoresinol into piperitol, and piperitol into sesamin.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

Example 10

Functional Analysis of SiP189 Protein in Plant Cells

In order to confirm the biological functions of SiP189 protein in plant cells, tabaco (*N. tabaccum*) was transformed with the SiP189 gene.

With the restriction enzymes BamHI and XhoI, pSPB2055 including SiP189 was digested. A resulting DNA fragment of about 1.5 kb including ORF of the SiP189 was ligated with the BamHI site and SalI site of a plant transforming binary vector pSPB176, so as to obtain a binary vector pSPB2057. The multiple cloning site of the pSPB176 is flanked by the CaMV35S promoter and the NOS terminator. The insert inserted in these sites is constitutively expressed in excess in the plant cells under the control of CaMV35S promoter.

The pSPB2057 was transformed into *agrobacterium* (strain: Aglo) according to a conventional method (Shimonishi et al., New Introductions to Biological and Chemical Experiments 3, Kagaku Doujin (pp. 122-124)). The agrobacterium transformant was used to infect a tabaco leaf disk.

Figure 7:
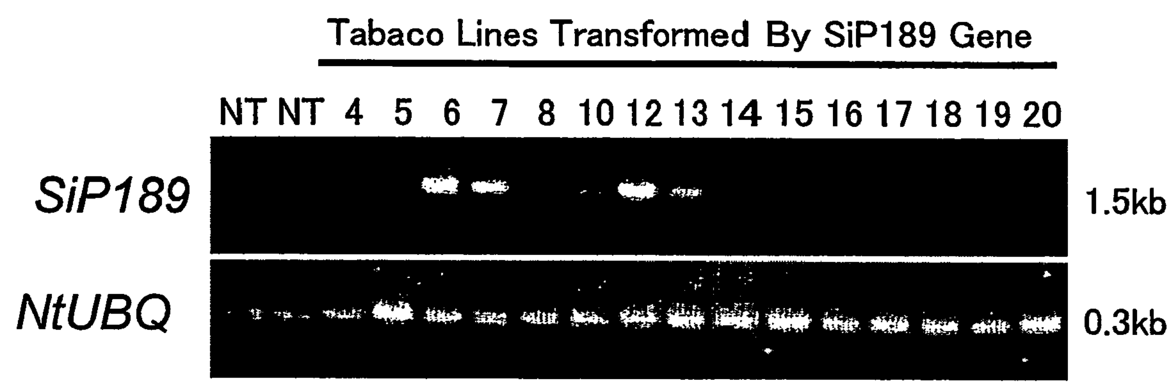
FIG. 7 is a diagram showing a result of expression analysis on SiP gene in transformant tabaco.
Figure 8A:
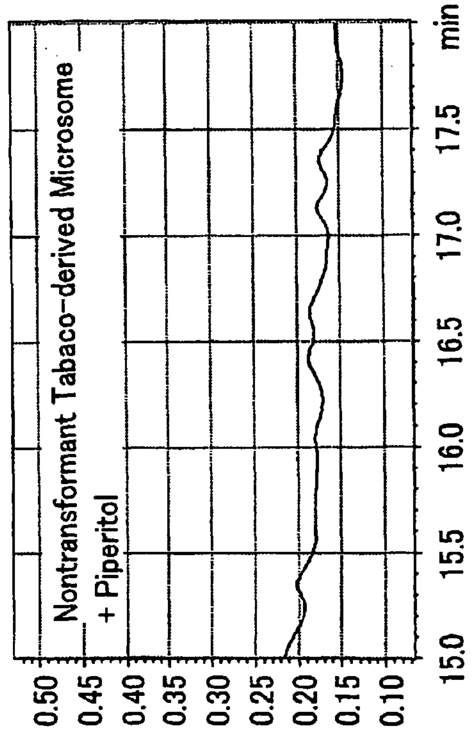
FIG. 8*a* through FIG. 8*d* are diagrams showing a result of functional analysis on SiP protein in plant cells.
Figure 8B:
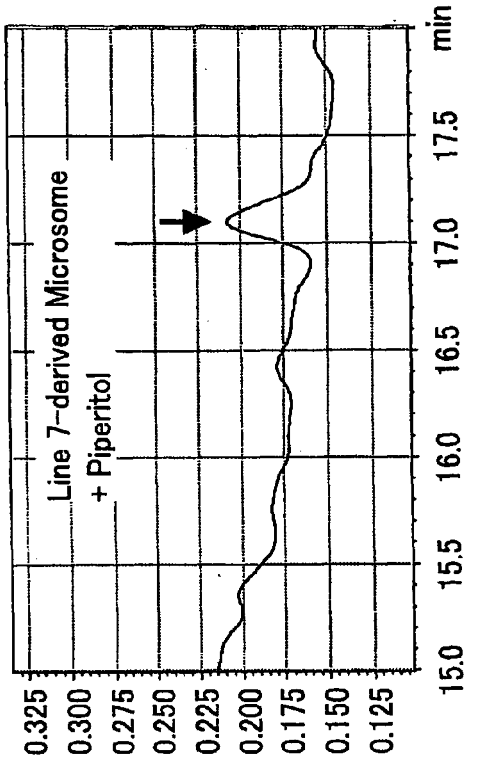
Figure 8C:
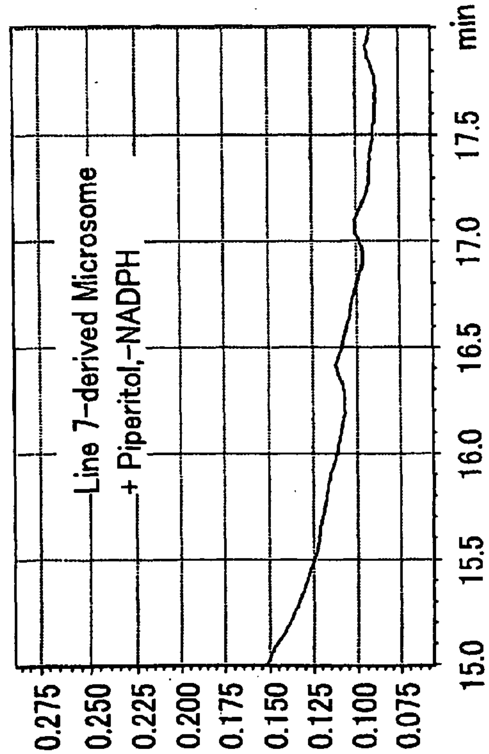
Figure 8D:
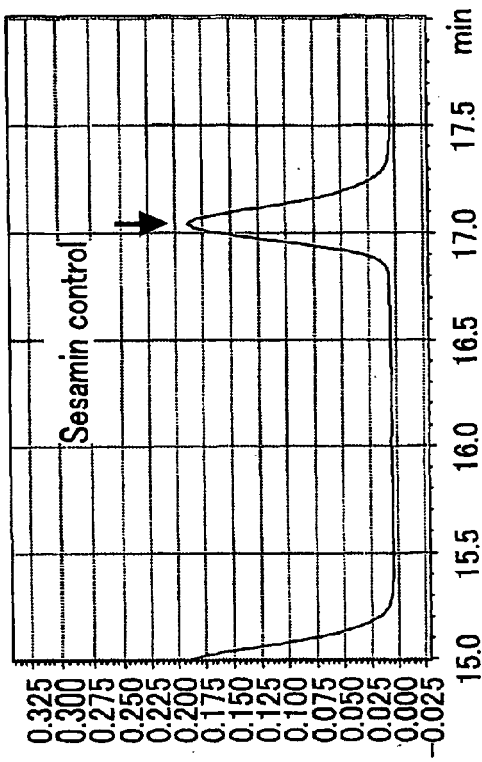
Figure 9B:
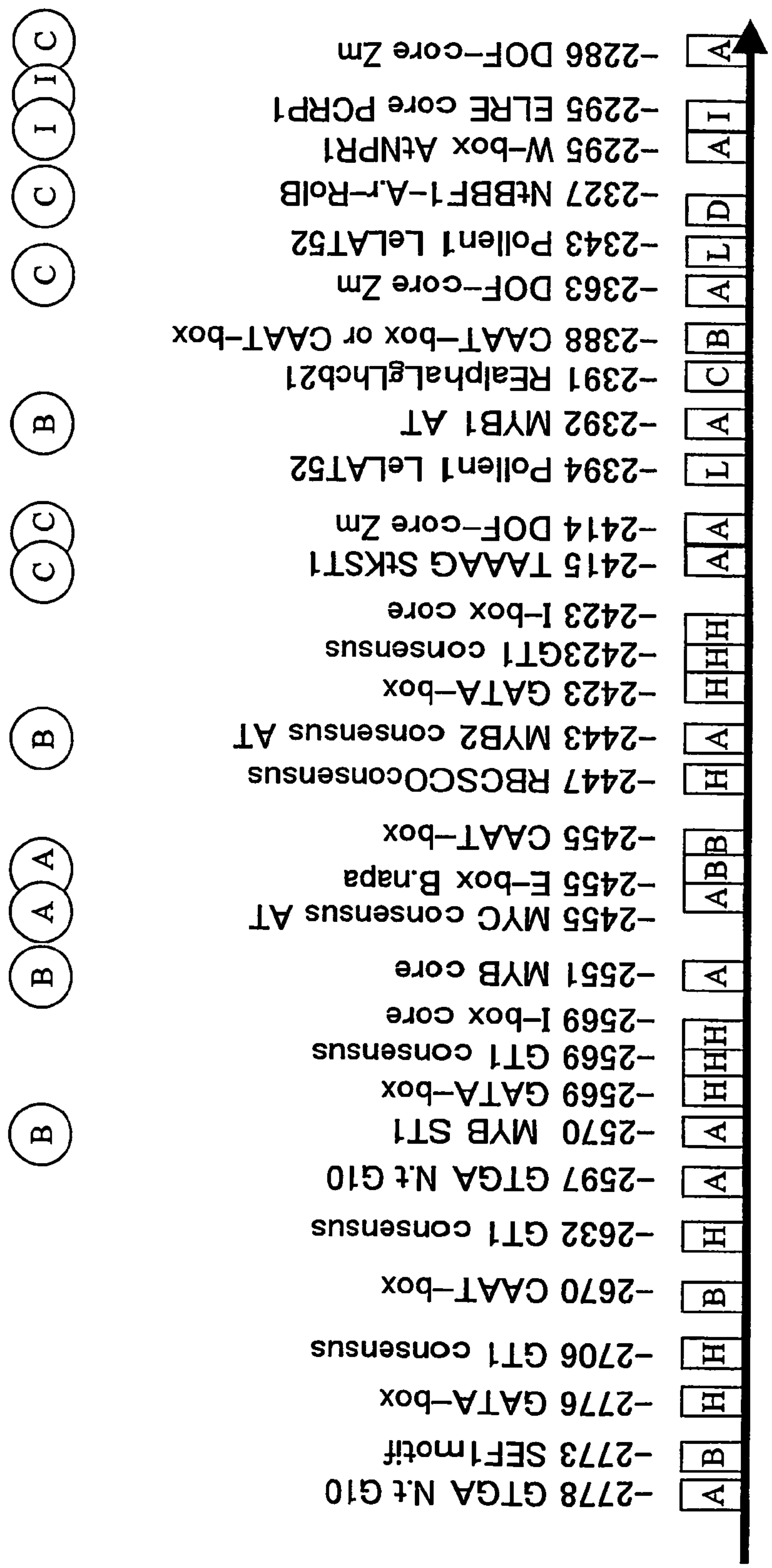
Figure 9C:
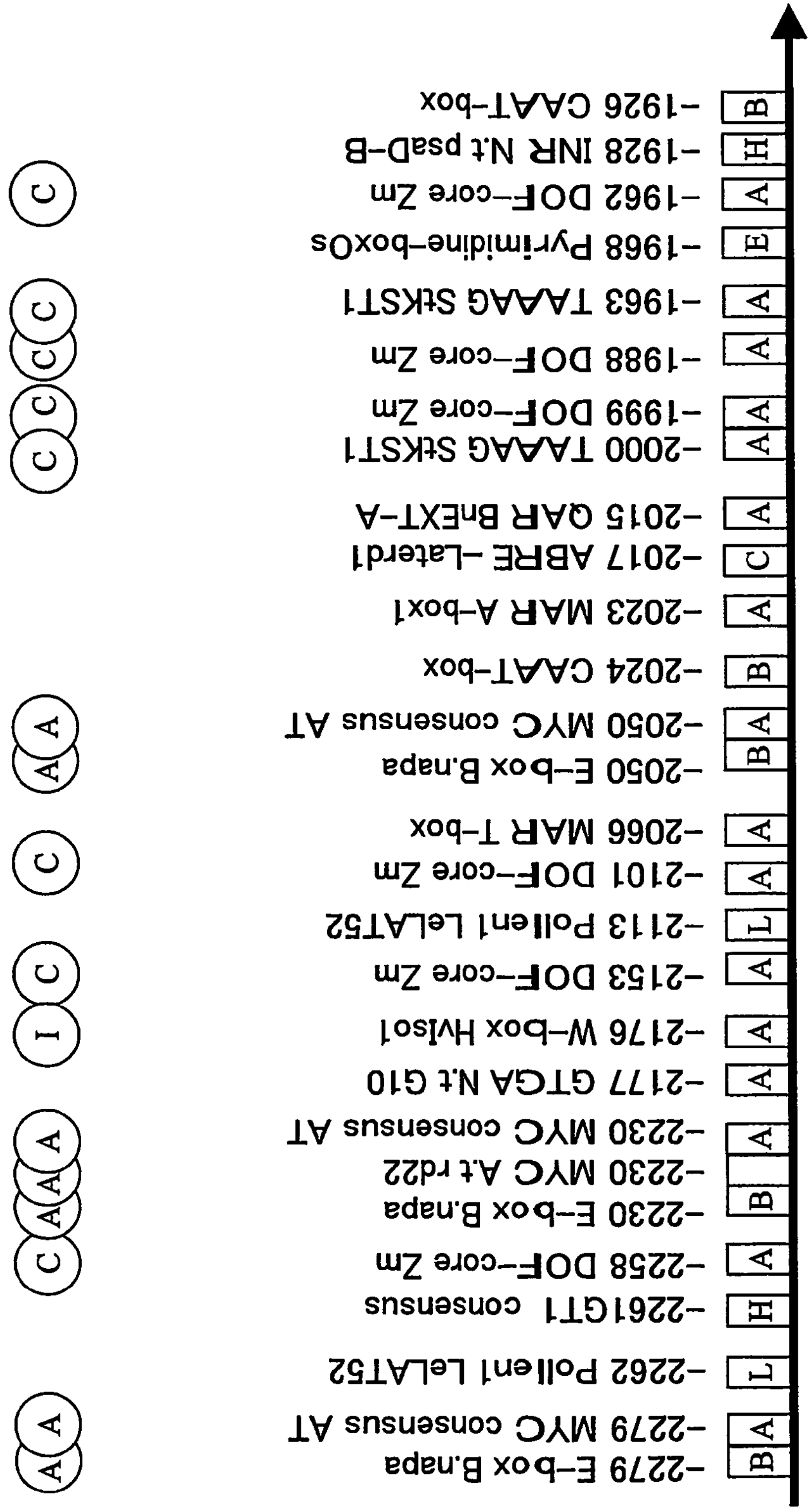
Figure 9D:
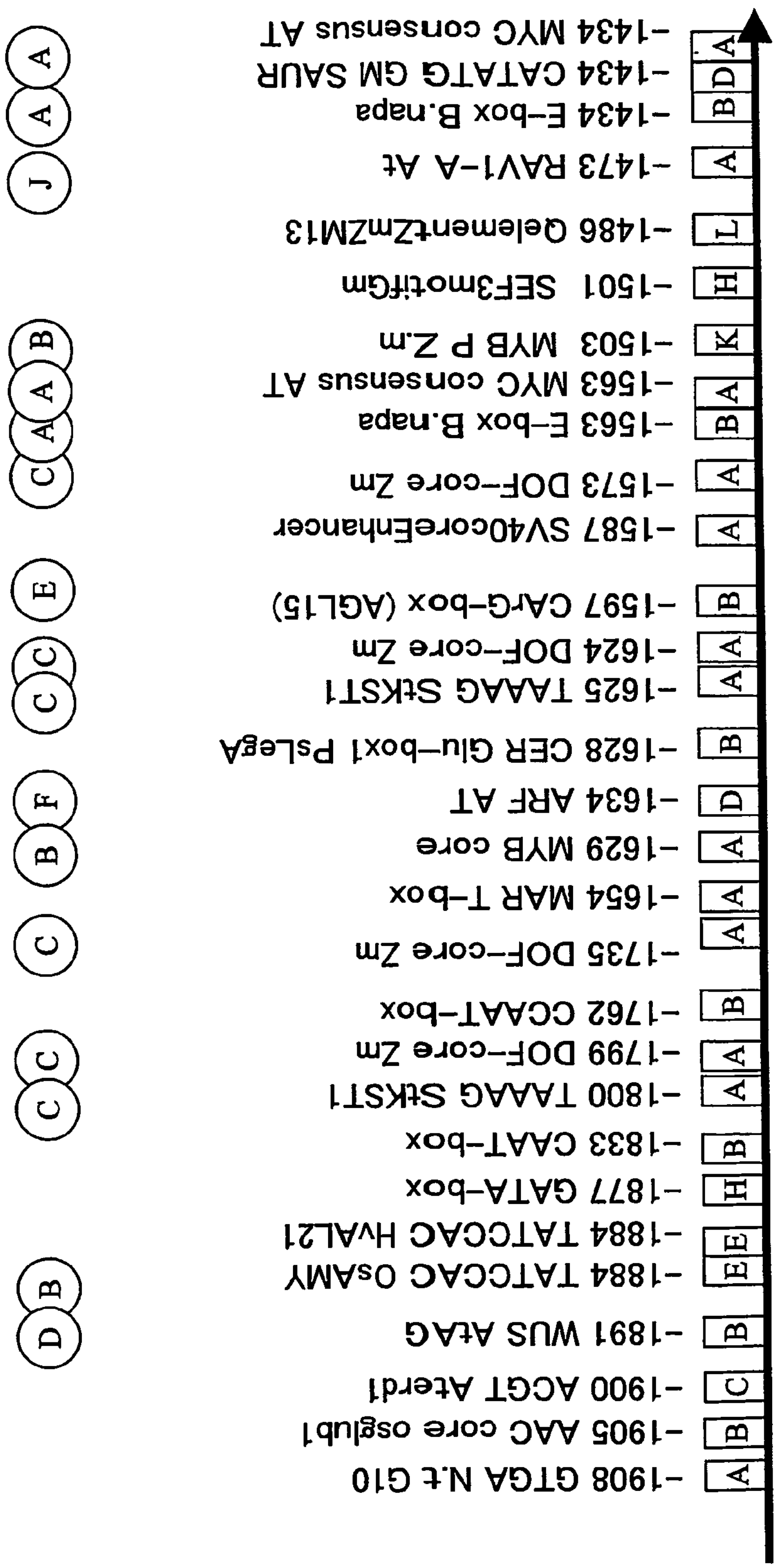
Figure 9E:
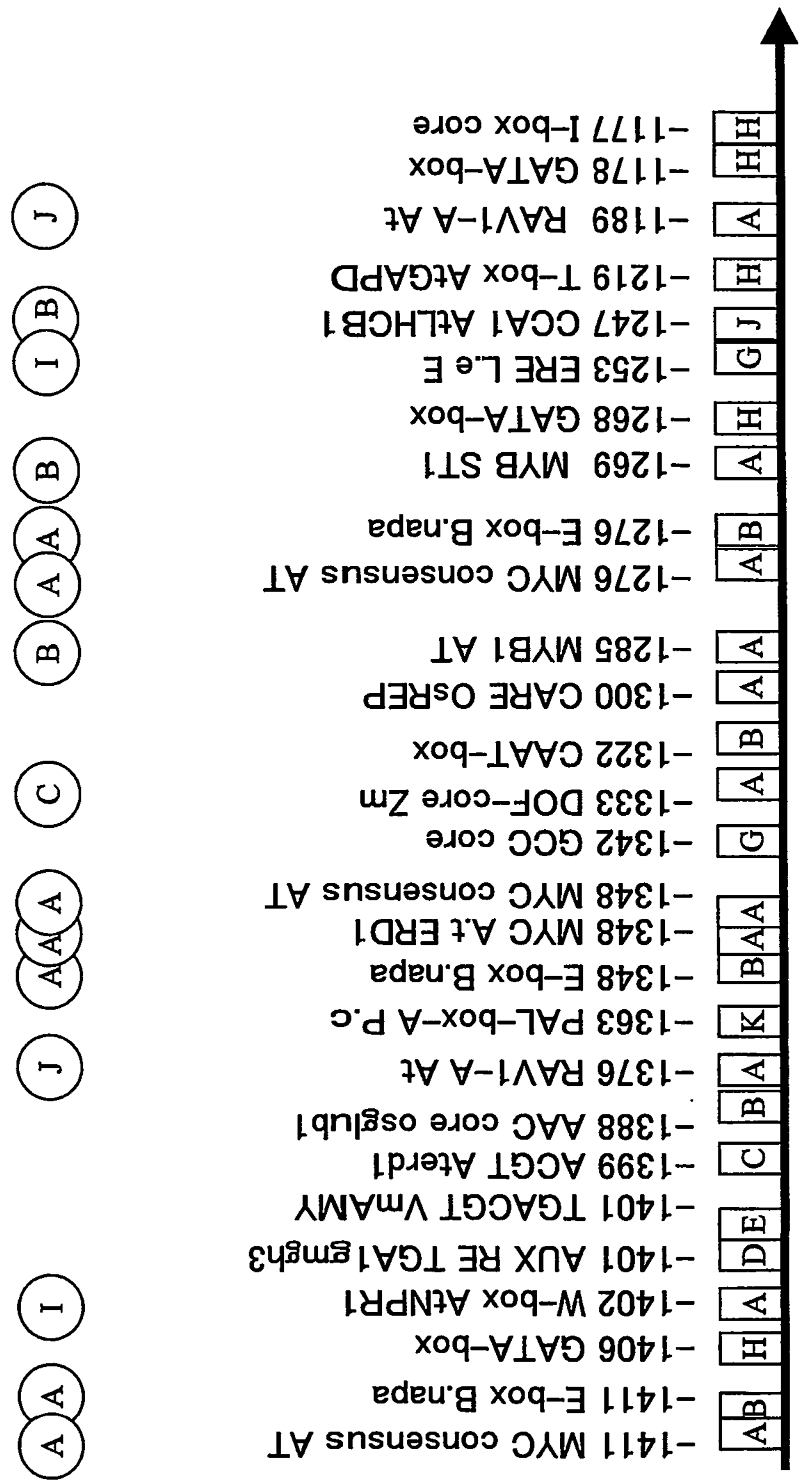
Figure 9F:
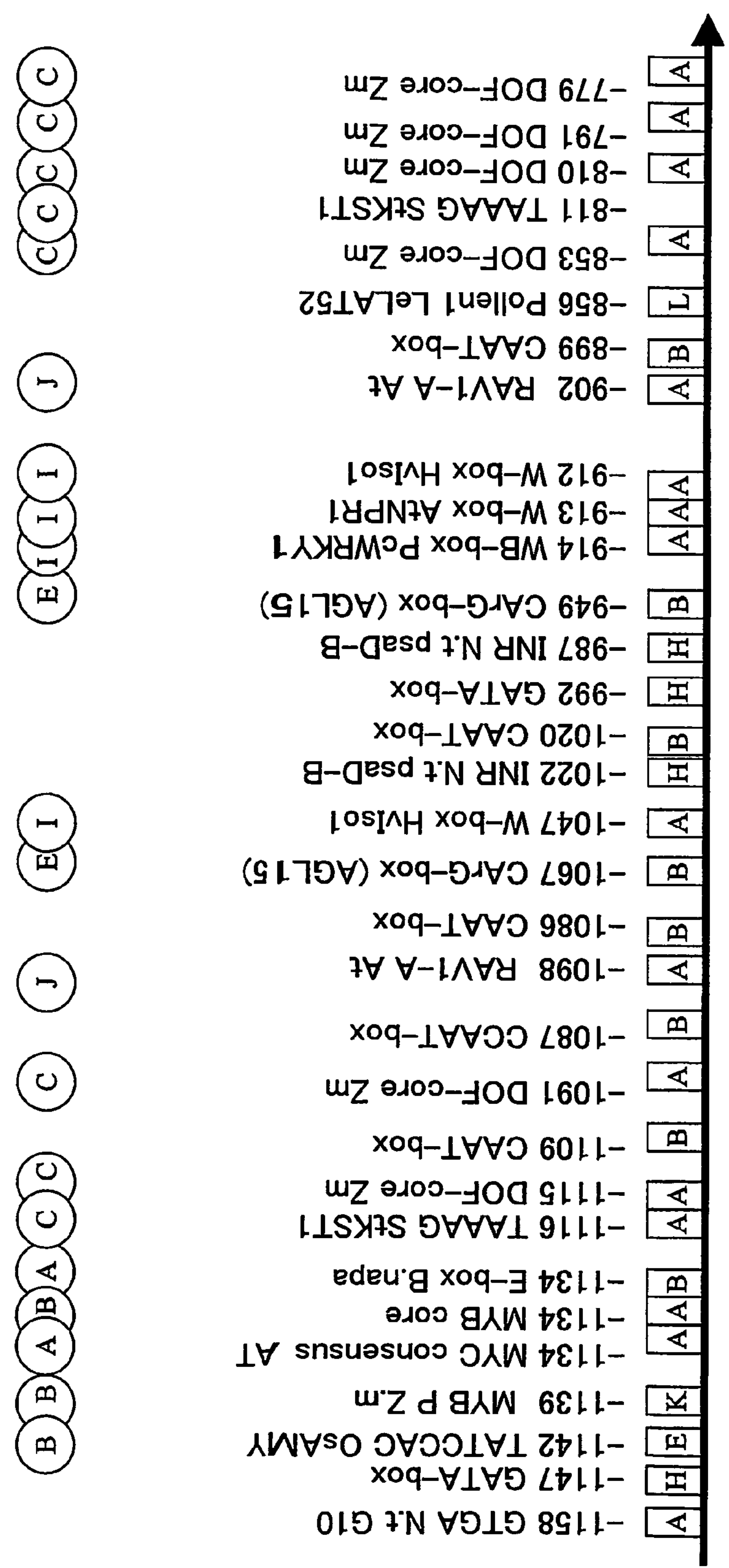
Figure 9G:
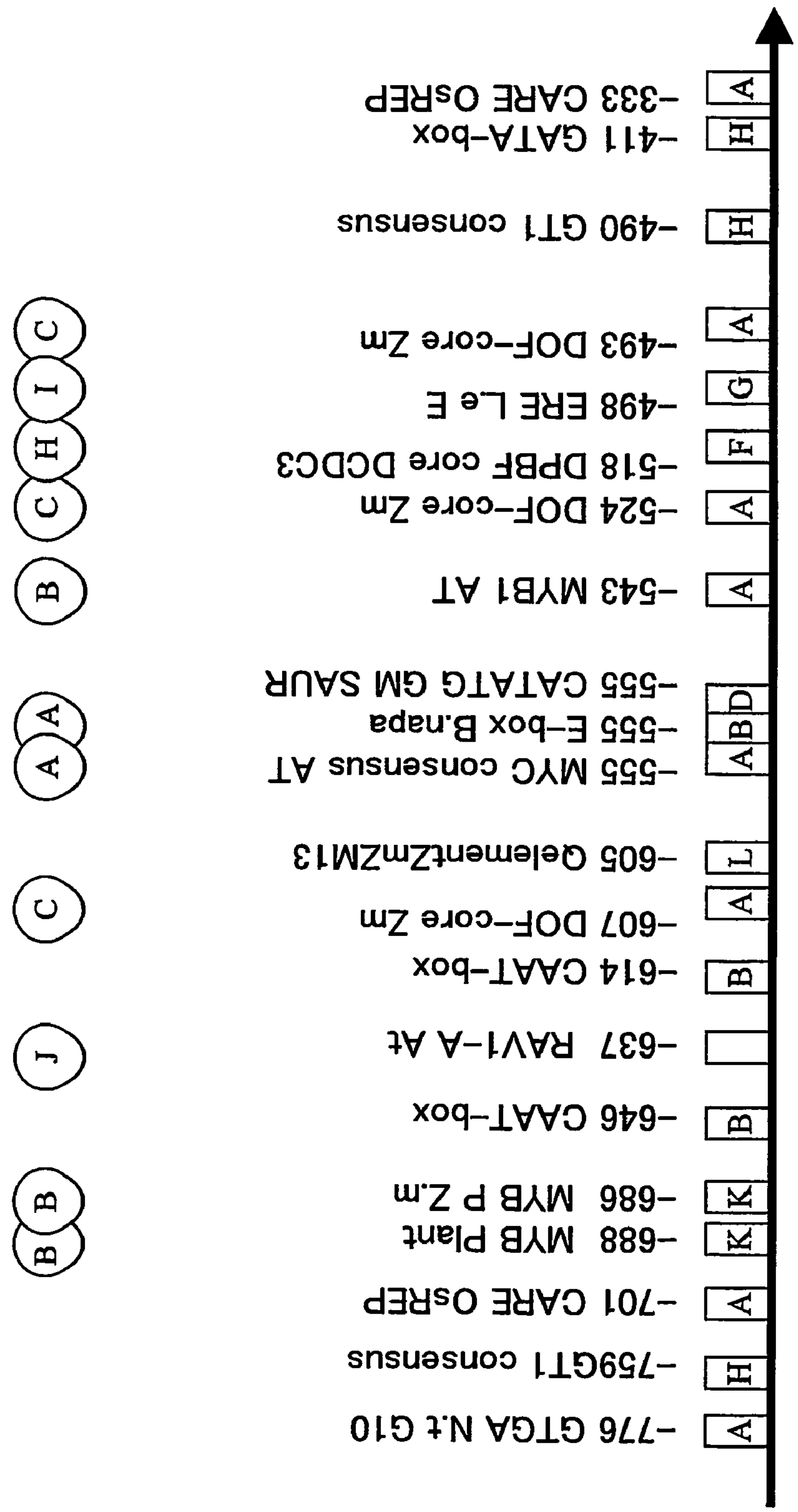
Figure 9H:
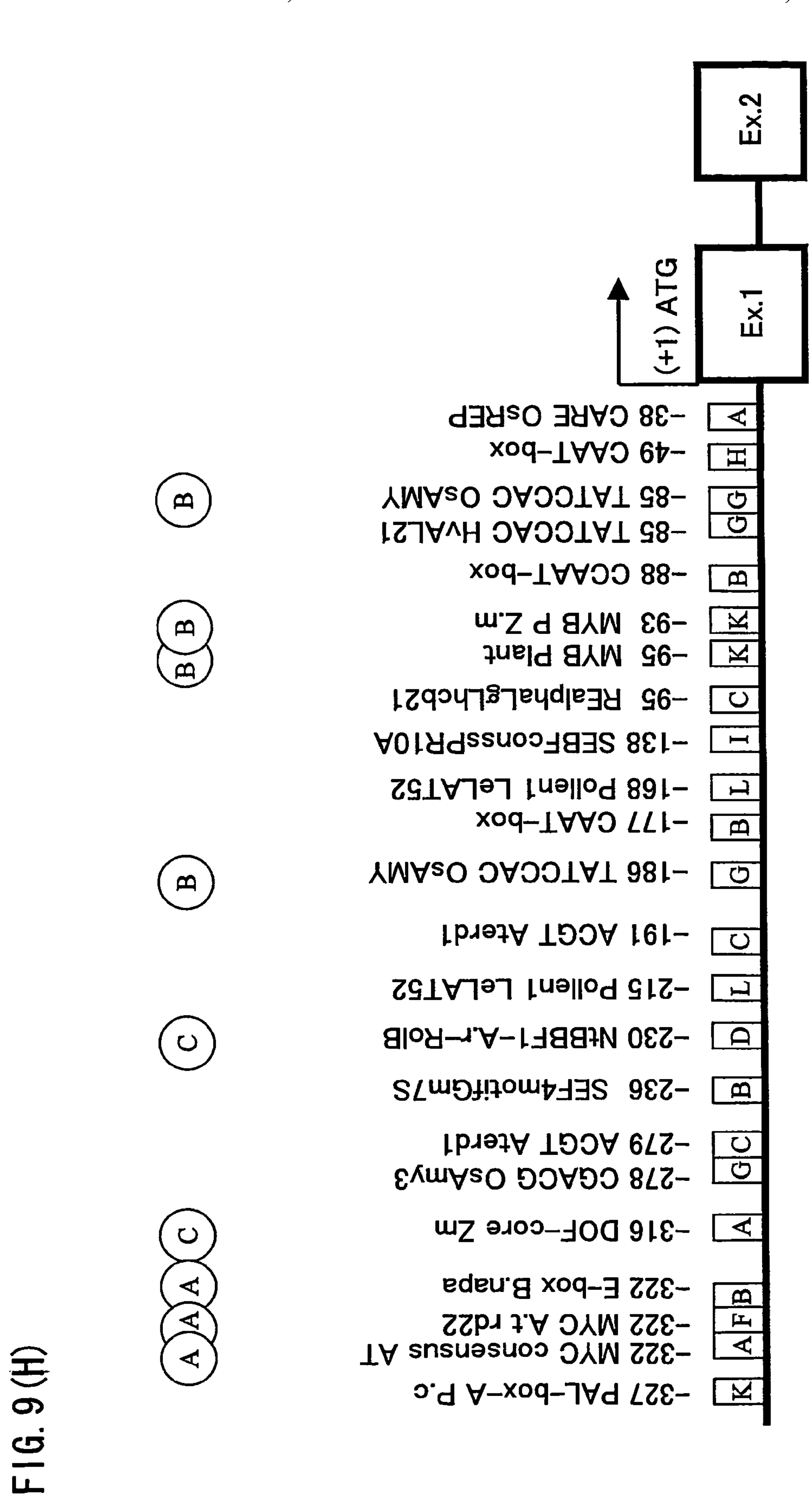

From the leaves of thirteen lines of the transformants, cDNA was prepared according to the method of Example 2. Then, RT-PCR was carried out according to the method of Example 4, using primers of SEQ ID NOs: 49 and 50. A ubiquitin gene of tabaco (NtUBQ accession No: U66264) was amplified as an internal control gene, using primers consisting of the nucleotide sequences of SEQ ID NOs: 66 and 67 (NtUBQ-FW, NtUBQ-RW, respectively). The result confirmed the presence of highly-expressed SiP189 gene in lines 6, 7, and 12 (FIG. 7).

The following procedure was carried out on ice or at 4° C. About 15 g of each sample of transformant leaves (lines 6, 7, and 12) and non-transformant leaves was crushed with a pestle in liquid nitrogen, and was dissolved in 30 ml of homogenize buffer (0.1 M potassium phosphate buffer (pH 7.0), 0.5 M mannitol, 5 mM EDTA, 42 mM mercaptoethanol, 50 mM sodium ascorbate, 0.1% BSA, 1 mM PMSF, and 1% PVPP).

The mixture was centrifuged at 10000×g for 20 minutes, and the supernatant was filtered with a Miracloth. The filtrate was ultracentrifuged at 100000×g for 90 minutes to obtain a crudely extracted microsome fraction. The microsome fraction (240 μl) was subjected to the enzymatic reaction with piperitol according to the method of Example 4, and the resulting product was analyzed by HPLC.

The result of HPLC showed that the tabaco-derived microsome expressing SiP189 in excess had a peak which was not observed in the non-transformant, and was dependent on the presence of NADPH in the reaction mixture of enzyme. The peak coincided with the retention time of a sesamin standard, indicating the function of the SiP189 as a protein with the catalytic activity for the biosynthesis of sesamin in the plant cell (FIG. 8).

Example 11

Identification of Expression Regulatory Region in SiP189 Gene

To get the insight of the transcriptional regulation of SiP189 gene, a 5' non-coding region of the SiP189 gene was isolated, sequenced and analyzed. From the genomic DNA of sesame (*S. indicum*), a genome library was constructed using the λBlueSTAR™ Vector system (NOVAGEN).

200 μg of sesame genomic DNA was partially digested with the restriction enzyme Sau3AI to obtain fragments of about 20 kb. The DNA fragments were subjected to a sucrose density gradient centrifugation (10% to 40%) at 25000 rpm, at 10° C. for 24 hours (SW28 rotor, Beckman). The centrifuged samples were fractionated (1 ml each) using the AUTOMATIC LIQUID CHARGER (Advantec), and the Micro Tube Pump (EYELA). For each fraction, the size of fragments was confirmed by pulse-field gel electrophoresis. The pulse-field gel electrophoresis used a gel with 1% Agarose NA (Amersham biosceience) and 0.5×TBE, and was carried out in a 0.5×TBE buffer for 120°/1 sec. to 1 sec. at 6V/cm (CHEF MAPPER, Invitrogen). With the fractions containing fragments with an average fragment size of about 20 kb, a genome library was constructed according to the method recommended by the manufacturer. The library had a titer $1.5\times10^6$ pfu/500 μl. The genome library (500000 clones) was screened with a probe, for which about 850 bp ORF region of the SiP189 gene amplified with primers consisting of base sequences of SEQ ID NOs: 68 and 69 (SiP189-bam-FW and SiP189-nco-RV, respectively) was used.

The probed was labeled and detected with the AlkaPhos Direct Labeling and Detection system (Amersham bioscience) according to the method recommended by the manufacturer. Hybridization was carried out under the following conditions:

| | |
|---|---|
| Probe: | 5 ng/ml hybridization buffer |
| Prehybridization: | 55° C. for 1 hour |
| Hybridization: | 55° C. overnight |
| Washing: | twice at 55° C. for 30 minutes |

After the third screening, nine kinds of positive clones were isolated, and a gSiP189-#6 with an insert size of about 12 kb was obtained therefrom.

Then, PCR was carried out using primers of nucleotide sequences of SEQ ID NOs: 68 and 69, and phage arm primers STAR-LF1 (SEQ ID NO: 70) and STAR-LR1 (SEQ ID NO: 71), so as to determine the direction and position of the probe inserted in the gSiP189-#6.

The PCR analysis indicated gSiP189-#6 contains 5' non-coding region of SiP189 gene, no shorter than 5 kb. Based of this result, the entire nucleotide sequence of the gSiP189-#6 was determined.

The inserts were amplified by LA-PCR, using the gSiP189-#6 as a template. The reaction mixture of LA-PCR contained 1 μl of positive clone SM buffer suspension liquid, 1×LA buffer (TaKaRa), primers (1 pmol/μl each), 0.4 mM dNTP, 2 mM $MgCl_2$, and 2.5 U LA-Taq polymerase. The LA-PCR was carried out at 96° C. for 5 minutes, and then in 30 cycles at 98° C. for 10 seconds, at 55° C. for 10 seconds, and at 68° C. for 10 minutes. Finally, the product was maintained at 72° C. for 15 minutes.

The resulting fragments were physically cut, and DNA fragments of about 1 to 2 kb were fractionated. The fragments were end-blunted and inserted in the HincII site of the pUC118 (TaKaRa) to construct a shot gun library. The library had a titer $2.8 \times 10^6$ cfu/μl.

With the shot gun library derived from gSiP189-#6, *E. coli* DH10B strain (Invitrogen) was transformed by an electroporation method. From randomly picked 192 colonies, DNA was prepared using the TempliPhi DNA Sequencing Template Amplification kit (Amersham bioscience). The DNA so prepared was amplified using M13-47(F) primer (SEQ ID NO: 72) and RV-M(R) primer (SEQ ID NO: 73).

The product of amplification was purified with the Clean SEQ (Agecourt), and sequenced using the MegaBASE4000 (Amersham Bioscience). The sequence data was assembled by PHRAP (CAP4), and a CONTIG sequence, including a 5'-sequence of about 13 kb starting from the start methionine site of the SiP189 gene, was obtained.

In order to identify regulatory cis-elements at the 5'-region of the SiP189 gene, a 5'-sequence of about 3 kb starting from the start methionine site of the SiP189 gene (SEQ ID NO: 74) was analyzed by PLACE (Database of Plant Cis-acting Regulatory DNA Elements. The PLACE analysis identified a large number of binding sites for a specific transcription factor family, along with a large number of regulatory cis-elements that responded to a specific signal. This indicates their involvement in the expression of the SiP189 gene (FIG. 9 and FIG. 10).

Thereafter, a regulatory non-coding region of the SrSiP189 gene encoding the *S. radiatum*-derived enzyme that catalyzes the synthesis of piperitol and sesamin was isolated. Using the genomic DNA of *S. radiatum* as a template, PCR was carried out with primers SEQ ID NOs: 75 and 76 (gSST-FW1 and gSST-RV2, respectively). The primers were designed based on the genomic sequence of SiP189 set forth in SEQ ID NO: 74.

Figure 11:
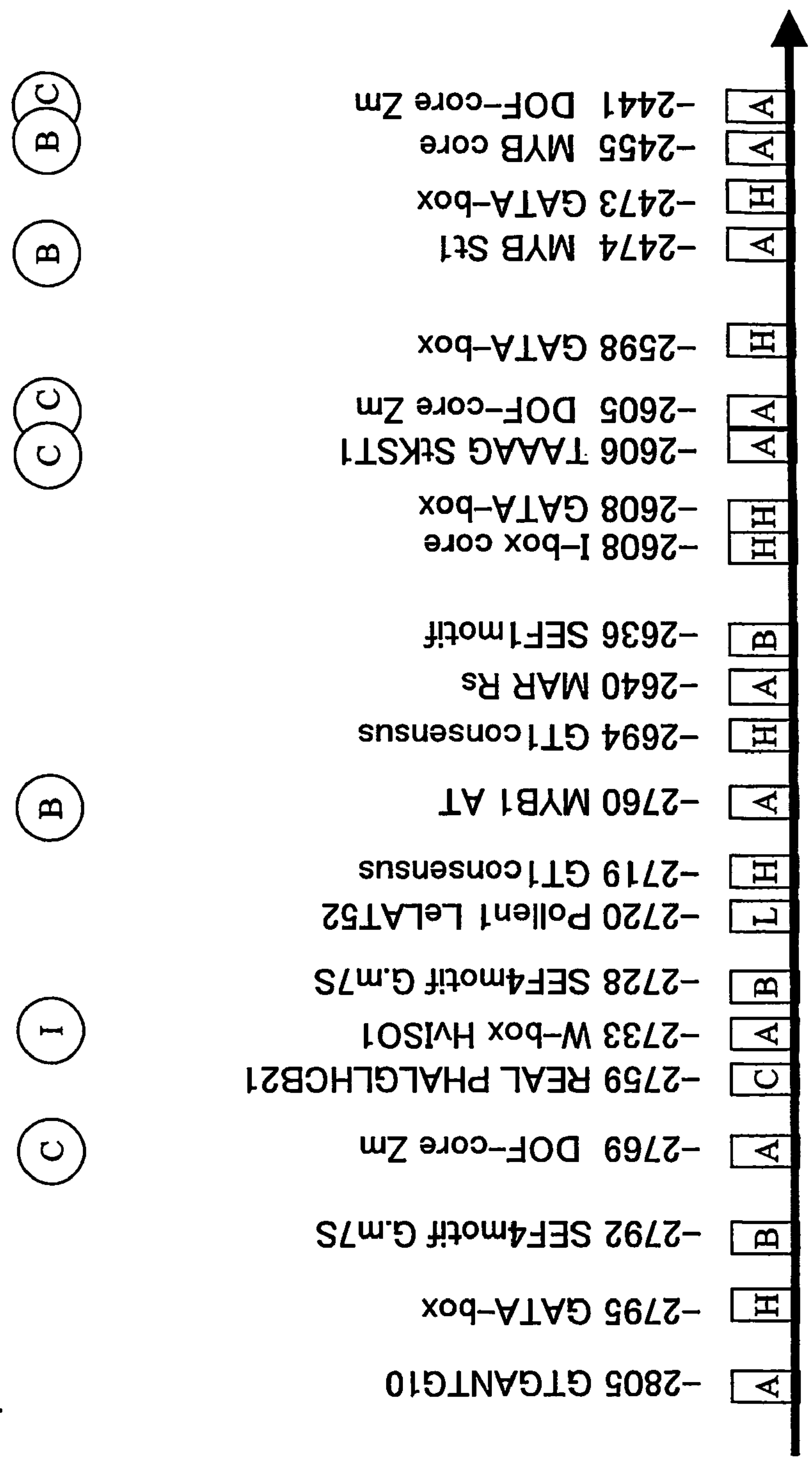
FIG. 11A through FIG. 11H are diagrams showing a result of analysis on a promoter region of SrSiP189 gene in search for an expression regulatory element.
Figure 11:
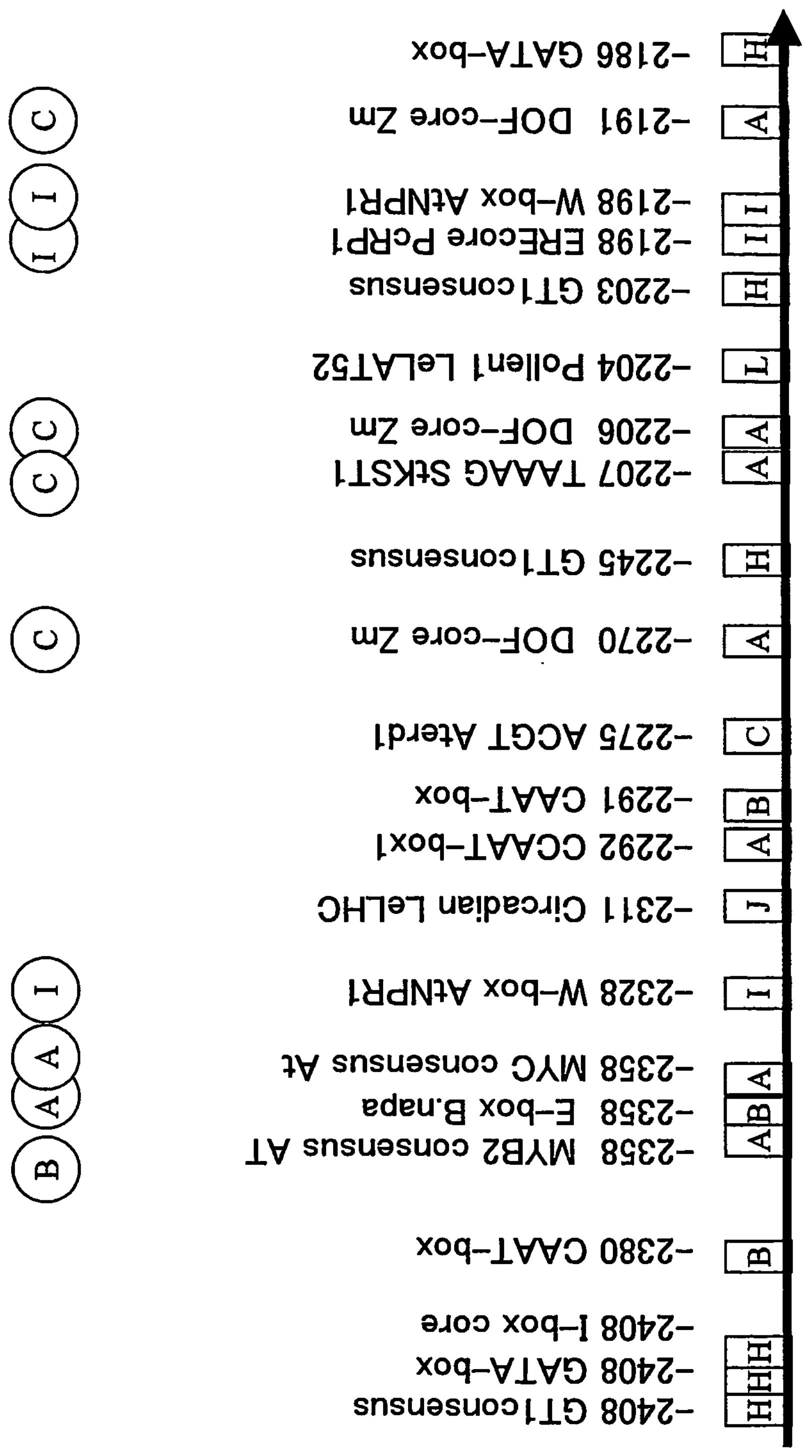
Figure 11:
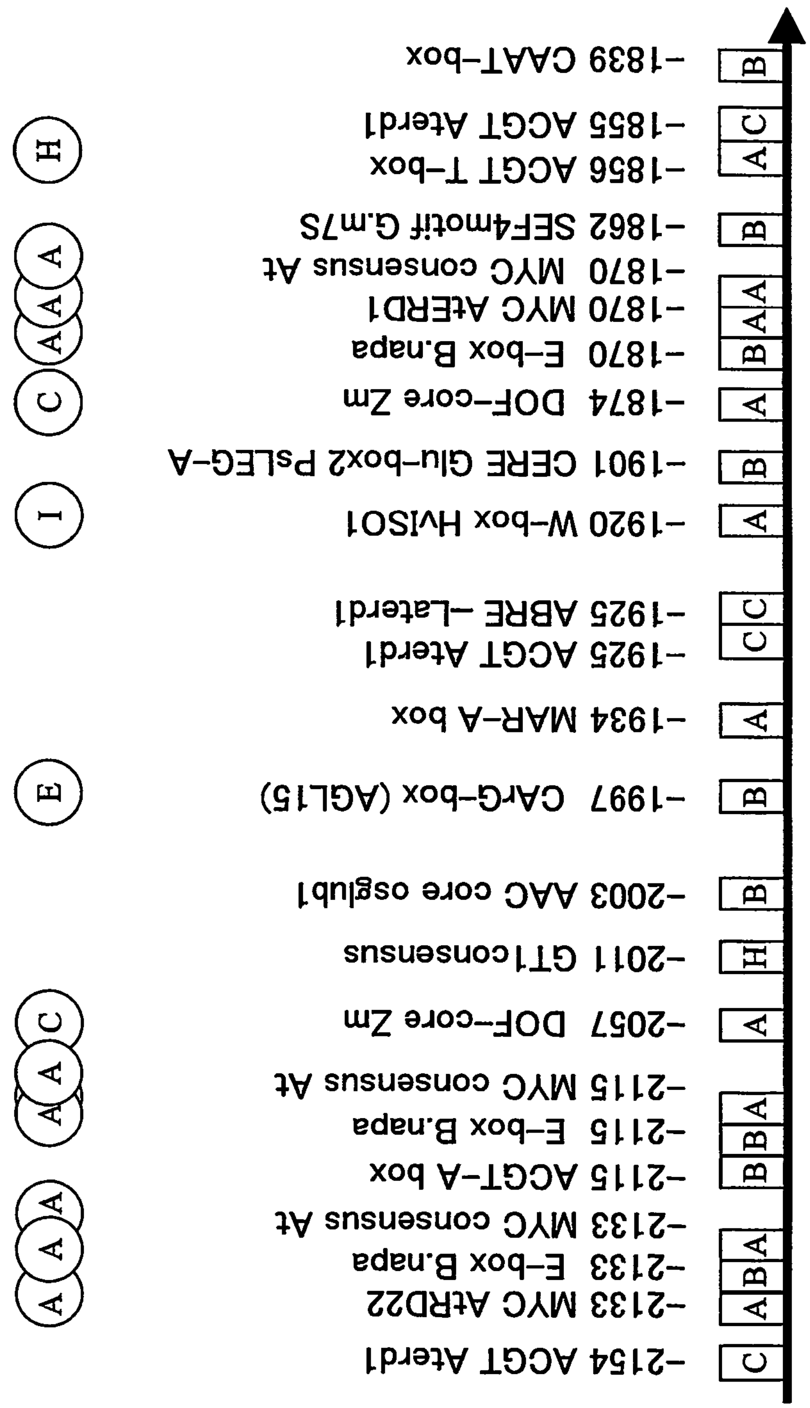
Figure 11:
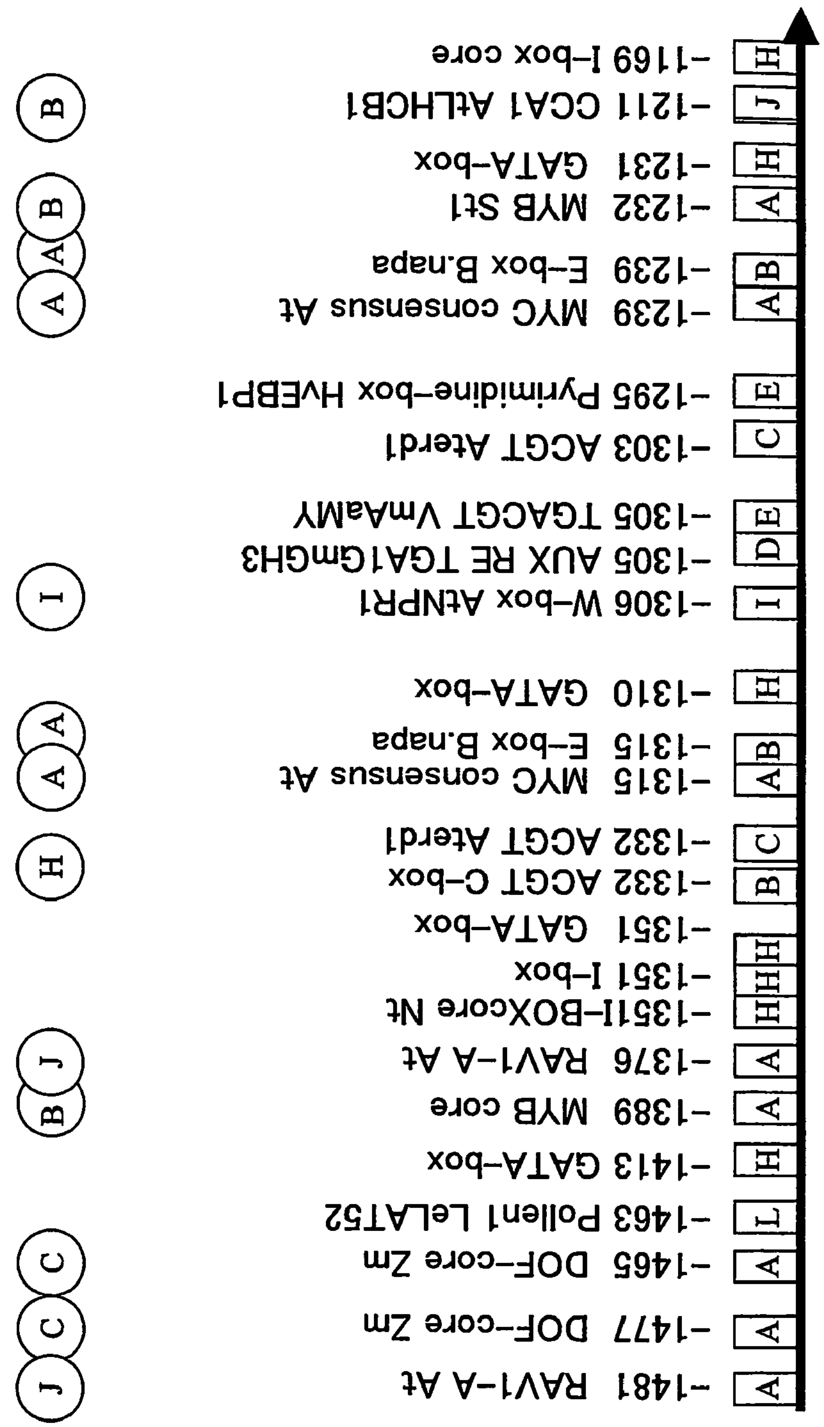
Figure 11:
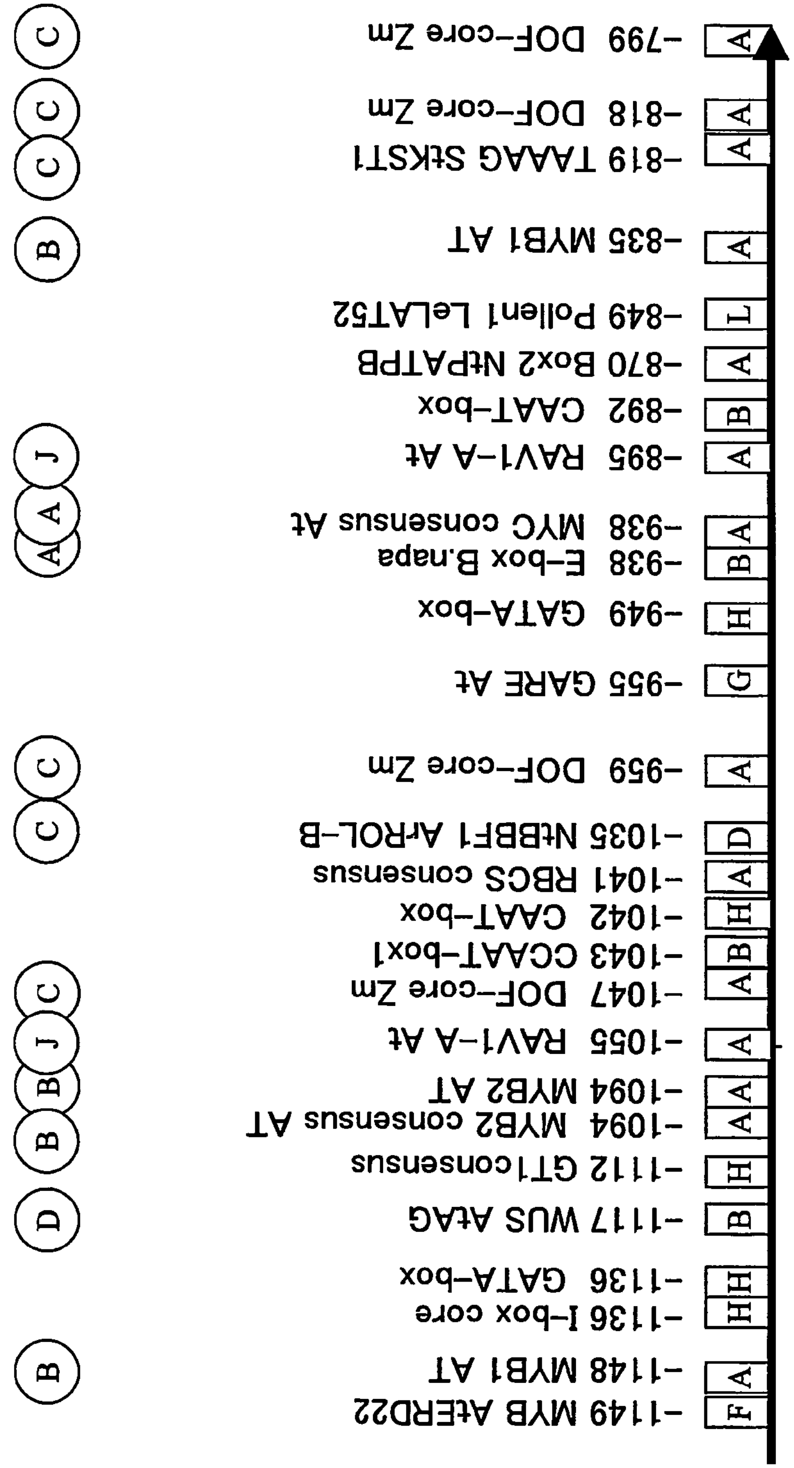
Figure 11:
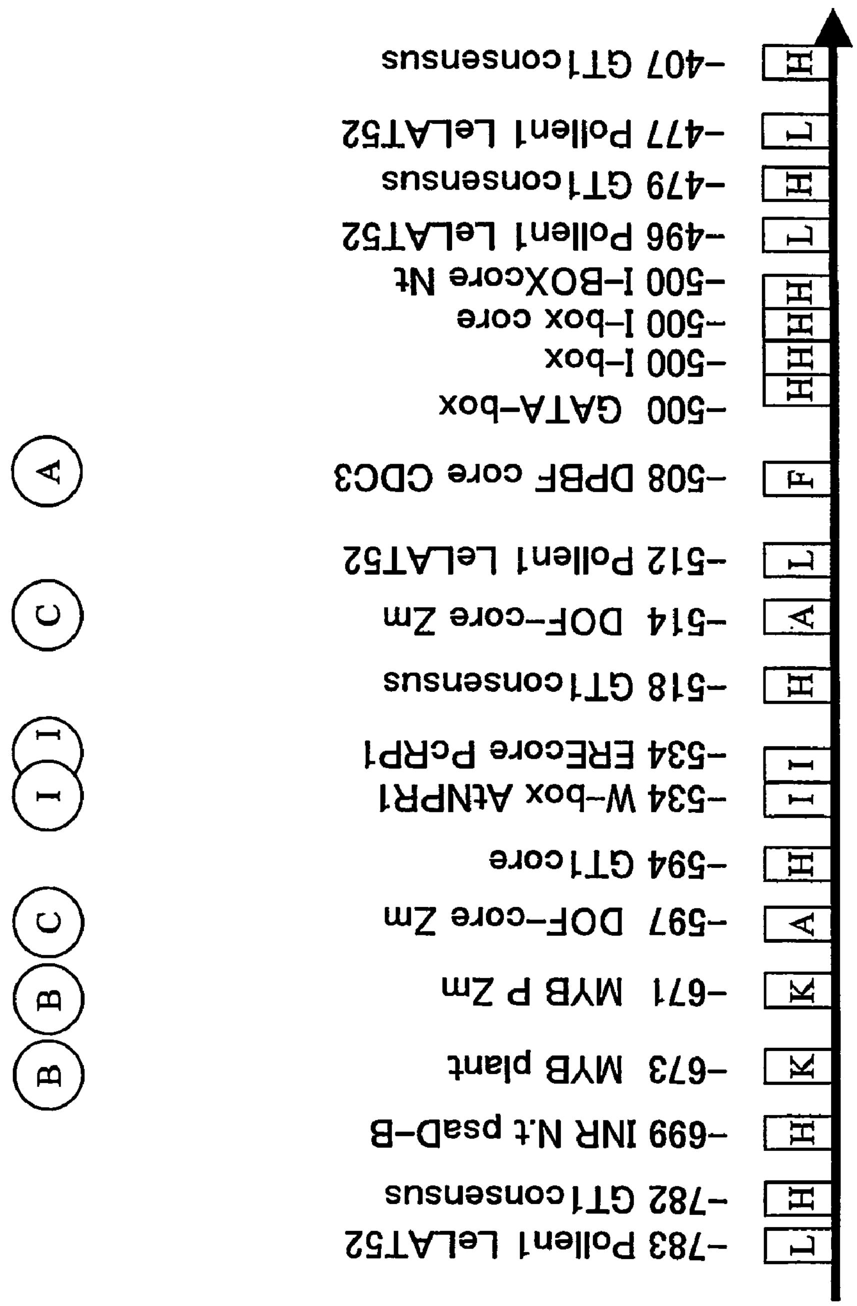
Figure 11:
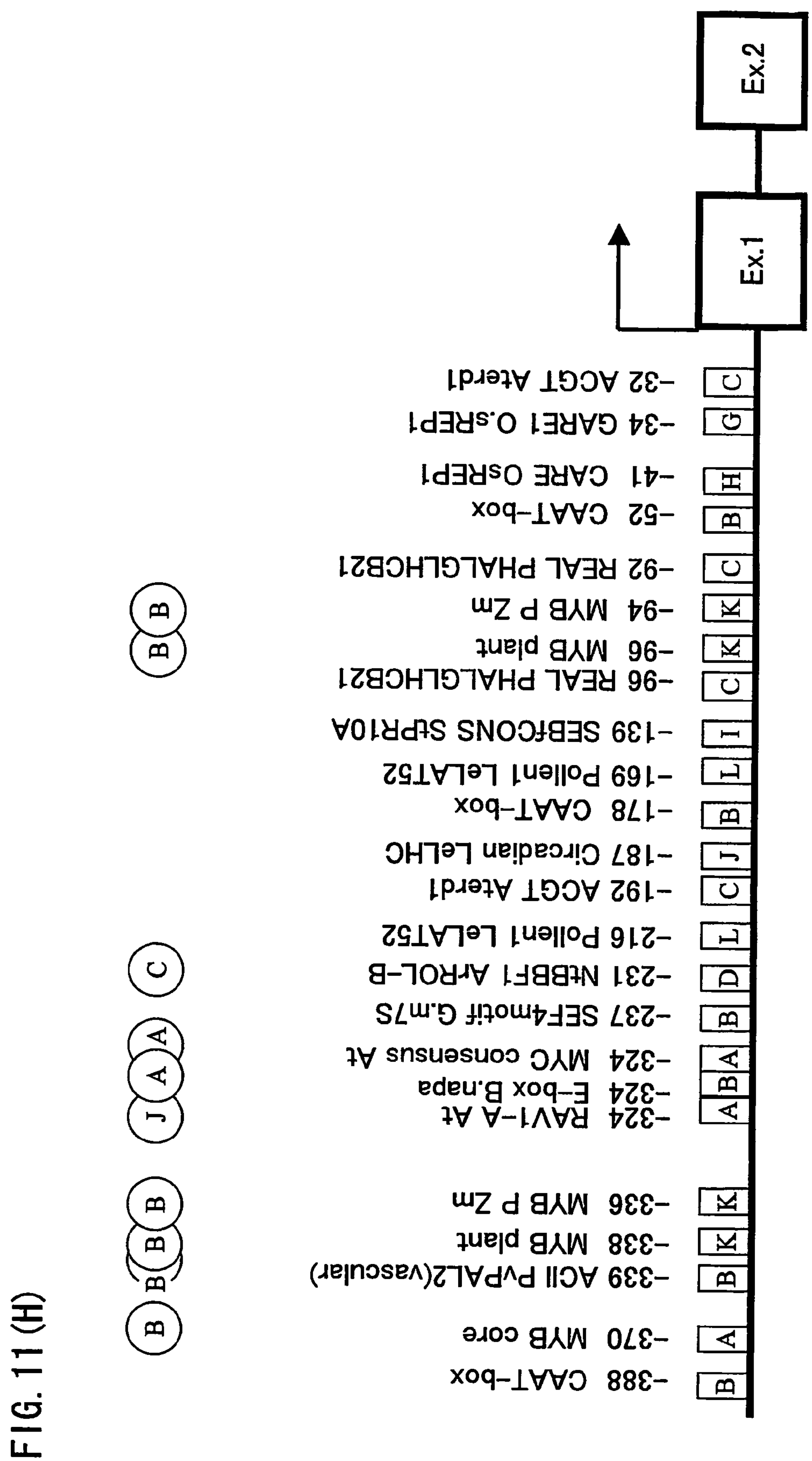

The reaction mixture contained 1 μl of genomic DNA (50 ng), 1×Ex-Taq buffer (TaKaRa), 0.2 mM dNTPs, primers (0.2 pmol/μl each), and 1.25 U Ex-Taq polymerase. The PCR was carried out at 94° C. for 5 minutes, and then in 30 cycles at 94° C. for 1 minutes, at 55° C. for 1 minute, and at 72° C. for 4 minutes. Finally, the product was maintained at 72° C. for 4 minutes. The resulting fragments were subjected to electrophoresis, and a fragment of about 3 kb was obtained. The fragment was inserted in the multiple cloning site of the pCR-TOPO-XL vector (Invitrogen) according to the method recommended by the manufacturer. As a result, pSPB2664 was obtained. The entire nucleotide sequence of the fragment inserted in the pSPB2664 was sequenced by a primer walking method. As a result, a fragment of about 2.8 kb at the 5'-region of the SrSiP189 gene (SEQ ID NO: 77), a probable sequence including the regulatory cis-elements of SrSiP189 gene, was obtained. The same PLACE analysis was performed as for the genomic SiP189 gene. The result identified a large number of binding sites for a specific transcription factor family, along with a large number of elements that responded to a specific signal (FIG. 11).

The SiP189 gene derived from cultivated sesame (*S. indicum*) and the SrSiP189 gene derived from *S. radiatum* were tested for their sequence identity on the DNA level according to the Clustal-W analysis (MacVector ver. 7.2.2, Symantech). These genes only had 78% sequence identity in the 5'-non-coding region of about 3 kb, but had a notably high sequence identity (96%) in the ORF region of the genes (FIG. 12). These results support our findings that SiP189 and SrSiP189 are highly conserved in terms of protein function but have different expression patterns. In addition to RT-PCR analyses, these cis-element analyses support that the two lignan biosynthetic genes, SiP189 from *S. indicum* and SrSiP189 from *S. radiatum* are not under an identical transcriptional regulation.

Example 12

*S. alatum* is an African wild sesame species that greatly differs (also in morphology) from cultivated *S. indicum* (Namiki et al., Science of sesame, Asakura Shoten). The number of chromosomes of *S. alatum* is the same as *S. indicum*, 2n=26, and the geographical distribution of *S. alatum* is in Nigeria, Sudan, and Mozambique in Africa.

With the same method of isolating the SrSiP189 gene from the African sesame *S. radiatum* in Example 8, a counterpart gene (SaSiP189) of SiP189 was isolated from *S. alatum*.

cDNA of Stage 4 of *S. alatum* was used as a template for PCR. A fragment of about 1.5 kb, that had been amplified with primers of SEQ ID No: 61 (Bam-SST-FW2) and SEQ ID NO: 63 (GR-SST-RV1), was subcloned to the pCR-blunt II TOPO (Invitrogen). The nucleotide sequence of the inserted fragment was determined by a primer walking method. SEQ ID NO: 78 shows the amino acid sequence of SaSiP189, and SEQ ID NO: 79 shows the nucleotide sequence of SaSiP189.

The resultant SaSiP189 showed 90% sequence identity on the DNA level, and 86% sequence homology on the amino acid level, as compared with SiP189. These results show that the gene SiP189 of lignan biosynthetic enzyme is a highly conserved gene, even in the presence of geographical isolation or morphological/cytogenetic difference.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

Previous research on sesamin has found various physiological activities of the compound, and sesamin is now known to possess a wide variety of recuperating effects. The present invention identified a gene that encodes an enzyme for catalyzing the biosynthesis of piperitol from pinoresinol, or of sesamin from piperitol. The sesame-derived cytochrome P450 gene (SiP gene) allows for production of sesamin and piperitol using a recombinant organism, and therefore increases sesamin yield and reduces production cost.

As described above, the sesame-derived SiP189 gene and SrSiP189 gene of the present invention encode cytochrome P450 that catalyzes the biosynthesis of piperitol from pinoresinol, and of sesamin from piperitol. Being an important food source since ancient times, sesame, including its seeds, seed oil, and seed extract, continues to hold its title as one of the healthiest foods available. Among many benefits offered by sesame, its physiological activities have caught the attention of many researchers. The SiP189 gene and SrSiP189 gene identified by the present invention can be used in the production of sesamin, which conventionally relied solely on sesame seeds. The present invention therefore holds great promise in increasing sesamin yield.

With these and other advantages of the present invention, the invention is useful in agriculture, food industry, pharmaceutical industry, and all other industries related to these fields.

The invention claimed is:

1. An isolated gene encoding a protein that catalyzes the biosynthesis of piperitol from pinoresinol and the biosynthesis of sesamin from piperitol, the protein comprising:

(a) the amino acid sequence of SEQ ID NO:1, 64, or 78: or (b) an amino acid sequence that has been modified by at least one of the substitution of one to 10 amino acids of, the deletion of one to 10 amino acids of, insertion of one to 10 amino acids to, and the addition of one to 10 amino acids to the amino acid sequence of SEQ ID NO:1, 64, or 78.

2. An isolated gene comprising the nucleotide sequence of SEQ ID NO:2, 65 or 79 as an open reading frame region.

3. The gene according to claim 1, wherein the gene is derived from sesame.

4. A recombinant expression vector comprising the gene according to claim 1.

5. A non-human transformant comprising a recombinant expression vector comprising the gene according to claim 1.

6. A producing method of a protein, comprising:

producing the transformant according to claim 5; and recovering a protein from the transformant that catalyzes the biosynthesis of piperitol from pinoresinol and the biosynthesis of sesamin from the piperitol.

7. The transformant according to claim 5, wherein the transformant comprises a plant, its offspring and portions thereof.

8. A method of producing at least one of piperitol and sesamin, comprising a step of introducing the gene according to claim 1 into a host cell.

9. A method of producing a non-human transformant containing an enhanced amount of lignan, comprising a step of introducing the gene according to claim 1 into a host cell.

10. A method of producing a plant containing an enhanced amount of at least one of piperitol and sesamin, comprising a step of introducing the gene according to claim 1 into a host cell.

11. A method of producing a non-human transformant containing a reduced amount of lignan, comprising a step of introducing the gene according to claim 1 into a host cell.

12. A method of producing a plant containing a reduced amount of at least one of piperitol and sesamin, comprising a step of introducing the gene according to claim 1 into a host cell.

13. A method of cultivating sesame, comprising a step of introducing the gene according to claim 1 into a host cell.

* * * * *